US012077582B2

(12) United States Patent
Jefferies et al.

(10) Patent No.: US 12,077,582 B2
(45) Date of Patent: Sep. 3, 2024

(54) ANTIBODIES TO L-TYPE VOLTAGE GATED CHANNELS AND RELATED METHODS

(71) Applicant: The University of British Columbia, Vancouver (CA)

(72) Inventors: Wilfred Arthur Jefferies, Surrey (CA); Kyung Bok Choi, Surrey (CA); Shawna Rose Stanwood, Burnaby (CA); Franz Fenninger, Vancouver (CA); Brett Alexander Eyford, Vancouver (CA); Lonna Munro, Vancouver (CA); Cheryl Gurine Pfeifer, Vancouver (CA); Reinhard Gabathuler, Quebec (CA)

(73) Assignee: The University of British Columbia, Vancouver (CA)

( * ) Notice: Subject to any disclaimer, the term of this patent is extended or adjusted under 35 U.S.C. 154(b) by 5 days.

(21) Appl. No.: 17/946,921

(22) Filed: Sep. 16, 2022

(65) Prior Publication Data
US 2023/0203154 A1    Jun. 29, 2023

Related U.S. Application Data

(63) Continuation of application No. 16/751,951, filed on Jan. 24, 2020, now Pat. No. 11,492,400, which is a continuation of application No. 15/549,912, filed as application No. PCT/US2016/018114 on Feb. 16, 2016, now abandoned.

(60) Provisional application No. 62/280,557, filed on Jan. 19, 2016, provisional application No. 62/115,823, filed on Feb. 13, 2015.

(51) Int. Cl.
*C07K 16/28* (2006.01)
*C07K 14/705* (2006.01)
*C07K 16/30* (2006.01)

(52) U.S. Cl.
CPC ............ *C07K 16/28* (2013.01); *C07K 14/705* (2013.01); *C07K 16/30* (2013.01); *C07K 2317/33* (2013.01); *C07K 2317/34* (2013.01); *C07K 2317/56* (2013.01); *C07K 2317/565* (2013.01); *C07K 2317/73* (2013.01); *C07K 2317/76* (2013.01)

(58) Field of Classification Search
None
See application file for complete search history.

(56) References Cited

U.S. PATENT DOCUMENTS

| 11,492,400 | B2 | 11/2022 | Jeffries et al. |
| 2002/0165353 | A1 | 11/2002 | Malouf et al. |
| 2005/0074850 | A1 | 4/2005 | Nadler et al. |
| 2016/0194393 | A1 | 7/2016 | Jefferies et al. |

FOREIGN PATENT DOCUMENTS

| WO | 2002/063000 A2 | 8/2002 |
| WO | 2005/033139 A2 | 4/2005 |
| WO | 2005/060479 A2 | 7/2005 |
| WO | 2013/020235 A1 | 2/2013 |
| WO | 2013/130808 A1 | 9/2013 |
| WO | 2016/131058 A1 | 8/2016 |
| WO | 2017/004435 A1 | 1/2017 |

OTHER PUBLICATIONS

"Cystic fibrosis", www.nhlbi.nih.gov/health/health-topics/topics/cf/; accessed Feb. 3, 2017, 2 paqes.
"Rheumatoid Arthritis", www.ncbi.nlm.nih.gov/pubmedhealth/PMH0050554/#consra2.s6; Nov. 20, 2012, 11 paqes.
"Human Immunodeficiency Virus (HIV)", "cystic fibrosis", www.nhlbi.nih.gov/health/health-topics/topics/cf/; accessed Feb. 3, 2017, 3 pages.
Badou, A. et al, "Critical role for the beta regulatory subunits of Cav channels in T lymphocyte function," PNAS USA (2006); 103(42):15529-15534.
Burgess, D. L. et al., "Mutation of the Ca2+ Channel ? Subunit Gene Cchb4 Is Associated with Ataxia and Seizures in the Letharqic (Ih) Mouse," Cell, 88:385-392 (1997).
Caterall, et al., "Voltage-gated ion channels and gating modifier toxins." Toxicon (2007); 49(2): 124-141.
Davenport, Bennett, et al. "Signature channels of excitability no more: L-type channels in immune cells." Frontiers in Immunology (2015); 6: 1-13.
Davies and Padlan, "Antibody-antigen complexes." Annu Rev Biochem. (1990); 59: 439-473.
Devereux, J., et al., "A comprehensive set of sequence analysis programs for the VAX." Nucleic Acids Research (1984); 12(1 Part 1): 387-395.
Elgert, K. Immunology: Understanding the immune system. New York: Wiley-Liss, 1996, p. 323, 3 paqes.
Fenninger et al. "P.A.02.02: Receptor editing leading to B lymphocyte tolerance is governed by the L-type calcium channel Cav1 .4," Abstracts of the 4th European Congress of Immunology, Sep. 7, 2015 (Sep. 7, 2015), p. 47. Retrieved from the Internet: <www.eci-vienna2015.org/images/docs/ECI2015_Abstract-Book-v2.pdf> on Sep. 13, 2016 (Sep. 13, 2016). entire document.
Goodwin, Leslie 0., et al. "Alternative splicing of exons in the alpha1 subunit of the rat testis L-type voltage-dependent calcium channel generates germ line-specific dihydropyridine binding sites." Molecular Human Reproduction (1998); 4.3: 215-226.
Grafton, G. et al., "A non-voltage-gated calcium channel with L-type characteristics activated by B cell receptor liqation," Biochem. Pharmacol., 66:2001-2009 (2003).

(Continued)

*Primary Examiner* — Christine J Saoud
*Assistant Examiner* — Jon M Lockard
(74) *Attorney, Agent, or Firm* — Snell & Wilmer L.L.P.

(57) ABSTRACT

Provided are antibodies, and antigen-binding fragments thereof, which specifically bind to an extracellular poor loop of an alpha 1a subunit of L-type voltage gated calcium channel, and related compositions, kits, and methods of use thereof, for instance, administration to a subject in need thereof to modify an immune response, for example, in the treatment of cancer.

1 Claim, 17 Drawing Sheets

Specification includes a Sequence Listing.

(56) References Cited

OTHER PUBLICATIONS

Grafton, G. et al., "Calcium channels in lymphocytes," Immunoloqy, 104(2): 119-126 (2001).
Healy, et al., "Different Nuclear Signals Are Activated by the B Cell Receptor during Positive Versus Negative Signaling." Immunity (1997); 6(4): 419-428.
Heng et al., "The Immunological Genome Project: networks of gene expression in immune cells." Nat Immunol (2008); 9: 1091-1094.
Hoek, Kristen L., et al. "Transitional B cell fate is associated with developmental stage-specific regulation of diacylglycerol and calcium signaling upon B cell receptor engagement." The Journal of Immunology (2006); 177.8: 5405-5413.
International Preliminary Report on Patentability for International Application No. PCT/CA2012/050542, dated Feb. 11, 2014, 9 pages.
International Search Report and Written Opinion for International Application No. PCT/CA2012/050542, mailed Dec. 3, 2012, 13 pages.
International Search Report and Written Opinion for International Application No. PCT/US2016/018114, mailed May 17, 2016, 10 paqes.
International Search Report and Written Opinion for International Application No. PCT/US2016/040517, mailed Oct. 11, 2016, 9 pages.
International Preliminary Report on Patentability for International Application No. PCT/US2016/018114, dated Aug. 15, 2017, 6 pages.
Jha, M. K. et al., "Defective survival of nalive CD8(+) T lymphocytes in the absence of the beta3 regulatory subunit of voltage-gated calcium channels," Nature Immunology, 10( 12): 1275-1282 (2009).
Kotturi, M. F. et al, "Identification and Functional Characterization of Voltage-dependent Calcium Channels in T Lymphocytes," J. Biol. Chem., 278(47):46949-46960 (2003).
Kotturi, M. F. et al, "Roles of CRAC and CaV-like channels in T cells: more than one gatekeeper?," Trends Pharmacol. Sci., 27(7):360-367 (2006).
Kotturi, M. F. et al., "Molecular characterization of L-type calcium channel splice variants expressed in human T lymphocytes," Molecular Immunoloqy, 42(12):1461-1474 (2005).
Lipscombe, D. et al., "L-type calcium channels: the low down," J. Neurophysiol. 92(5):2633-2641 (2004).
McRory, J.E. et al., "The CACNA1 F gene encodes an L-type calcium channel with unique biophysical properties and tissue distribution," J. Neuroscience, 24(7): 1707-1718 (2004).
Mansergh, et al. "Mutation of the calcium channel gene Cacna1f disrupts calcium signaling, synaptic transmission and cellular organization in mouse retina." Human Mol Genet (2005); 14(20): 3035-3046.
Matsumoto, Masanori, et al. "The calcium sensors STIM1 and STIM2 control B cell regulatory function through interleukin-10 production." Immunity (2011 ); 34.5: 703-714.
Oh-Hora, M., "Calcium signaling in the development and function of T-lineage cells," Immunol. Rev., 231(1):210-224 (2009).
Omilusik, K. et al., "The Cav1 .4 calcium channel is a critical regulator of T cell receptor signaling and naive T cell homeostasis," Immunity, 35(3):349-360 (2011).
Omilusik, K.D., et al., "Weft, warp, and weave: the intricate tapestry of calcium channels regulatingT lymphocyte function." Frontiers in Immunology (2013); 4: 164, 12 pages.
Park, C. Y. et al., "The CRAC channel activator STIM1 binds and inhibits L-type voltage-gated calcium channels," Science, 330:101-105 (2010).
Priatel, J. J. et al., "RasGRP1 transduces low-grade TCR signals which are critical for T cell development, homeostasis, and differentiation," Immunity, 17(5):617-627 (2002).
Priatel, J. J. et al., "RasGRPl transmits prodifferentiation TCR signaling that is crucial for CD4 T cell development," The Journal of Immunoloqy 177:1470-1480 (2006).
Priatel, J. Jet al., "Chronic immunodeficiency in mice lacking RasGRP1 results in CD4 T cell immune activation and exhaustion," The Journal of Immunology, 179(4):2143-2152 (2007).
Revy, P. et al., "Functional antigen-independent synapses formed between T cells and dendritic cells," Nat. Immunol., 2(10):925-931 (2001).
Stokes, L. et al., "Non-voltage-gated L-type Ca2+ channels in human T cells: pharmacology and molecular characterization of the major alpha pore-forming and auxiliary beta-subunits," J. Biol. Chem., 279(19): 19566-19573 (2004).
Supplementary European Search Report for European Application No. 12821707.2, mailed Feb. 3, 2015, 10 pages.
Suzuki, Y. et al., "L-type Ca2+ channels: A new player in the regulation of Ca2+ signaling, cell activation and cell survival in immune cells," Mol. Immunol., 47:640-648 (2010).
Tyson, J. R. et al., "Molecular nature of voltage-gated calcium channels: Structure and species comparison," WIREs Membr. Transp. Siqnal, 2(5):181-206 (2013).
Wang, Y. et al., "The calcium store sensor, STIMI, reciprocally controls Orai and CaV1 .2 channels," Science, 330:105-109 (2010).
Wyatt, C. N. et al., "Voltage-dependent binding and calcium channel current inhibition by an anti-a1 D subunit antibody in rat dorsal root ganglion neurons and guinea-pig myocytes," J. Physiol., 502(Pt. 2):307-319 (1997).
Zhang, Zhao, et al. "Functional roles of Cav1. 3 (a1 D) calcium channels in atria insights gained from qene-targeted null mutant mice." Circulation (2005); 112.13: 1936-1944.
MacCallum et al. "Antibody-antigen interactions: contact analysis and binding site topography," (1996). J. Mol. Biol. 262:732-745.
De Pascalis et al. ""Abbreviated" Complementarity-Determining Regions Containing Specificity-Determining Residues Essential for Ligand Contact to Engineer a Less Immunogenic Humanized Monoclonal Antibody" (2002). Journal of Immunology. 169:3076-3084.
Gasset et al. (2003). Biochemical and Biophysical Research Communications. 307: 198-205.
Chen, et al. "Selection and analysis of an optimized anti-VEGF antibody: crystal structure of an affinity-matured Fab in complex with antigen." Journal of Molecular Biology, 1999. 293:865-881.
Wu, et al. "Humanization of a murine monoclonal antibody by simultaneous optimization of framework and CDR residues," Journal of Molecular Biology, 1999. 294:151-162.
Rudikoff et al. "Single amino acid substitution altering antigen-binding specificity," Proceedings of the National Academy of Sciences Mar. 1982, 79 (6) 1979-1983.
USPTO; Non-Final Office Action dated Jul. 29, 2019 in U.S. Appl. No. 15/549,912.
Nakai et al. "Critical roles of the S3 segment and S3-S4 linker of repeat I in activation of L-type calcium channels." Proceedings of the National Academy of Sciences Feb. 1994, 91 (3) 1014-1018.
Adachi-Akahane. "Molecular and pharmacological bases for the gating regulation of I-type voltage-dependent Ca2+ channels." Folia Pharm. Jpn. vol. 123, Issue 3, pp. 197-209 (2004).
Non-Final Office Action dated Jan. 6, 2022 in U.S. Appl. No. 16/751,951.
Notice of Allowance dated Jul. 12, 2022 in U.S. Appl. No. 16/751,951.

| Name | Peptide | Number of Mice | Number of lymphocytes harvested | Number of lymphocytes fused | Number of lymphocytes frozen in LN2 |
|---|---|---|---|---|---|
| Cav1.1 | PMQIELRHREWVH | 2 | 6.6 x 10E7 | 0.5 x 10E8 | 1.6 x 10E7 |
| Cav1.2 | ATKADGANALGGKGA | 2 | 5.9 x 10E7 | 0.5 x 10E8 | 0.9 x 10E7 |
| Cav1.3 | LTKETEGGNHSSGKSG | 2 | 9.15 x 10E7 | 0.5 x 10E8 | 4.6 x 10E7 |
| Cav1.4 | GPGRPGDAPHTG | 2 | 1 x 10E8 | 0.5 x 10E8 | 5.0 x 10E7 |
| | | | Total lymphocytes fused: | 2 x 10E8 | |
| | | | % of fusion: | 200% | |
| | | | % of fused cells plated out: | 100% | |
| | | | % of fused cells frozen in LN2: | 100% | |

FIG. 2

|  | 1A3 | 1B9 | 1B10 | 1B11 | 1C8 | 1C10 | 1D2 | 1E7 | 1F4 | 1F7 | 2B3 | 2D4 |
|---|---|---|---|---|---|---|---|---|---|---|---|---|
| All Cav1s | + | + |  | + | + | + | + | + | + | + | + |  |
| Cav1.1 |  |  |  |  |  |  |  | + | + |  |  |  |
| Cav1.2 | + | + |  |  | + |  | + |  |  | + |  |  |
| Cav1.3 |  | + | + | + | + |  | + |  |  |  |  | + |
| Cav1.4 | + |  |  |  |  | + | + |  |  |  | + |  |

FIG. 3

| Specificity | #thymus | #spleen | Total Hybridomas |
|---|---|---|---|
| $Ca_V1.1$ | 2 | 3 | 3 |
| $Ca_V1.2$ | 9 | 5 | 11 |
| $Ca_V1.3$ | 9 | 15 | 18 |
| $Ca_V1.4$ | 2 | 2 | 4 |

FIG. 8

| Target | Gene Symbol | % identity w mouse | Unigene http://www.ncbi.nlm.nih.gov/unigene | biogps.org http://biogps.org/#goto=welcome | Protein Atlas http://www.proteinatlas.org | Zenbu http://fantom.gsc.riken.jp/zenbu/ | cbioportal.org http://www.cbioportal.org | EMBL EBI expression atlas http://www.ebi.ac.uk/gxa/home;jsessionid=542F83A6983303FBB | Broad Institute cancer cell lines http://www.broadinstitute.org/ccle/home |
|---|---|---|---|---|---|---|---|---|---|
| Cav1.1 | CACNA1S | 92.50% | 31 cDNA sequences, muscle, larynx, thyroid, prostate; adult; some leukemia | skeletal muscle is highest expression (by far) | skeletal muscle (RNA and protein) | bronchial epithelial cells, smooth muscle cell, other epithelial | mutations and amplifications in many solid tumors... | skeletal muscle | Burkett lymphoma, medulloblastoma, endometrium. High expression in NCI-H2342 lung carcinoma |
| Cav1.2 | CACNA1C | 98.10% | 181 sequences, more widely expressed, in development, cancer; spleen, thymus, mammary gland, uterus, etc. | widely expressed blood, brain... | both protein and RNA in many tissues, smooth muscle...etc | GM progenitor, heart, smooth muscle...etc. | Often amplified and mutations in many tumors... | brain, colon, heart, smooth muscle, uterus | chondrosarcoma, lymphoma, leukemia, neuroblastoma. High expression in SUP-HD1, Hodgkin lymphoma |
| Cav1.3 | CACNA1D | 97.90% | 105 sequences, more widely expressed, bone, brain, lung, intestine, pituitary, etc, colorectal and prostate cancer etc but mostly adult | some expression in many tissues, most in pancreas, pituitary | some RNA in many tissues, highest adrenal; protein in many tissues, highest in adrenal, kidney, testis | good expression in many cells and cell lines, including bronchial epithelial, GM progenitor, heart. | Abundant mutations (25%) in DESM, others | intestine, lung, adrenal, lung, pituitary | lung small cell, breast... High expression in ZR-75-30 breast carcinoma |
| Cav1.4 | CACNA1F | 92.30% | 50 sequences, Selectively expressed in eye (different transcript), lung, muscle, thymus, all adult, no embryonic or juvenile expression. | Some pineal gland expression. | Very small amount in lung and small intestine, no antibodies to look at protein level. | leukocyte cell lines. | Expressed in many cancers and abundant mutated. | Retina and pineal gland; also some in intestine, spleen, lung, lymph node | leukemia, lymphoma, meningioma..High expression in NCI-H524 lung carcinoma |

FIG. 10

ANTIBODIES TO L-TYPE VOLTAGE GATED CHANNELS AND RELATED METHODS

CROSS-REFERENCE TO RELATED APPLICATIONS

This application is a continuation of U.S. application Ser. No. 16/751,951, filed on Jan. 24, 2020, which is a continuation of U.S. application Ser. No. 15/549,912, filed on Aug. 9, 2017, which is a national stage entry of PCT/US2016/018114, filed on Feb. 16, 2016, which claims priority under 35 U.S.C. § 119(e) to U.S. Application No. 62/115,823, filed Feb. 13, 2015; and U.S. Application No. 62/280,557, filed Jan. 19, 2016; each of which is incorporated by reference in its entirety.

STATEMENT REGARDING THE SEQUENCE LISTING

The Sequence Listing associated with this application is provided in text format in lieu of a paper copy, and is hereby incorporated by reference into the specification. The name of the text file containing the Sequence Listing is 7199700936.xml. The xml file is about 134,792 bytes, was created on Feb. 22, 2023, and is being submitted electronically via EFS-Web.

BACKGROUND

Technical Field

Embodiments of the present invention include antibodies, and antigen-binding fragments thereof, which specifically bind to one or more of the L-type voltage calcium channels Cav1.4, Cav1.3, Cav1.2, and Cav1.1, and related compositions and methods of use thereof.

Description of the Related Art

Immune cells, including T and B lymphocytes, are key mediators of immune responses against pathogens. Elevation of intracellular calcium ion ($Ca^{2+}$) levels is a vital event that regulates cell activation, proliferation, differentiation, and cell death in immune cells. Dysregulated Calcium responses in immune cells have been associated with several immunodeficiency and autoimmune diseases, such as X-linked agammaglobulinemia and systemic lupus erythematosus. While calcium signaling is known to play a role in immune function, the means by which calcium signals are generated in immune cells are not fully characterized. One mechanism of calcium entry into immune cells is through calcium release activated calcium (CRAC) channels. Other candidate plasma membrane calcium channels operating in immune cells include P2X receptors, transient receptor potential (TRP) channels, and voltage-gated calcium channels.

The voltage-gated calcium channels are multi-subunit proteins composed of a pore forming alpha 1 subunit and as well as at least an alpha 2 subunit, delta subunit, and beta subunit, and optionally, a gamma subunit. At least four subtypes of L-type voltage-gated calcium channels (also known as Cav1 channels or Cav1s) have been described: Cav1.1, Cav1.2, Cav1.3, and Cav1.4. These subtypes are categorized by the alpha 1 subunits they contain. These channels open in response to depolarization in the plasma membrane and thereby mediate $Ca^{2+}$ influx into excitable cells, such as neurons, muscle, and endocrine cells. Voltage gated calcium channels are also present in many cells not traditionally considered excitable, including various hematopoietic cells. Notably, expression of L-type voltage gated calcium channels has been observed in mouse and human lymphocytes (Kotturi et al., J.Biol. Chem. 278:46949-46960 (2003); Kotturi and Jefferies, Mol. Immunol. 42:1461-1474 (2005)).

Dysregulation of calcium signaling in immune cells contributes to inflammatory and autoimmune diseases. What are needed in the art are new agents that can bind and modify activity of targets in immune cells that regulate calcium signaling. While inhibitors to L-type voltage-gated calcium channels are presently available, these inhibitors are broadly targeted and produce undesirable side effects. The present invention addresses these needs by providing antibodies and antigen-binding fragments thereof that specifically target L-type voltage-gated calcium channels subtypes.

BRIEF DESCRIPTION OF THE FIGURES

FIG. 2 shows a table summarizing the results of hybridoma generation.

FIG. 3 shows a table displaying representative results of Eliza experiments performed with antibodies. Monoclonal antibodies produced by hybridomas were tested for binding to peptides with amino acid sequences taken from extracellular loops of L-type voltage-gated calcium channels. Wells were coated with BSA and peptides from all subtypes (All Cav1s), or with peptides from Cav1.1, Cav1.2, Cav1.3, or Cav1.4.

FIG. 8 shows a table summarizing characteristics of monoclonal antibodies produced by 31 selected clones with respect to channel specificity and their ability to bind to thymocytes and/or splenocytes.

FIG. 10 illustrates the mutations in CaV1 channels that can be found in cancer.

BRIEF SUMMARY OF THE INVENTION

Figure 1:
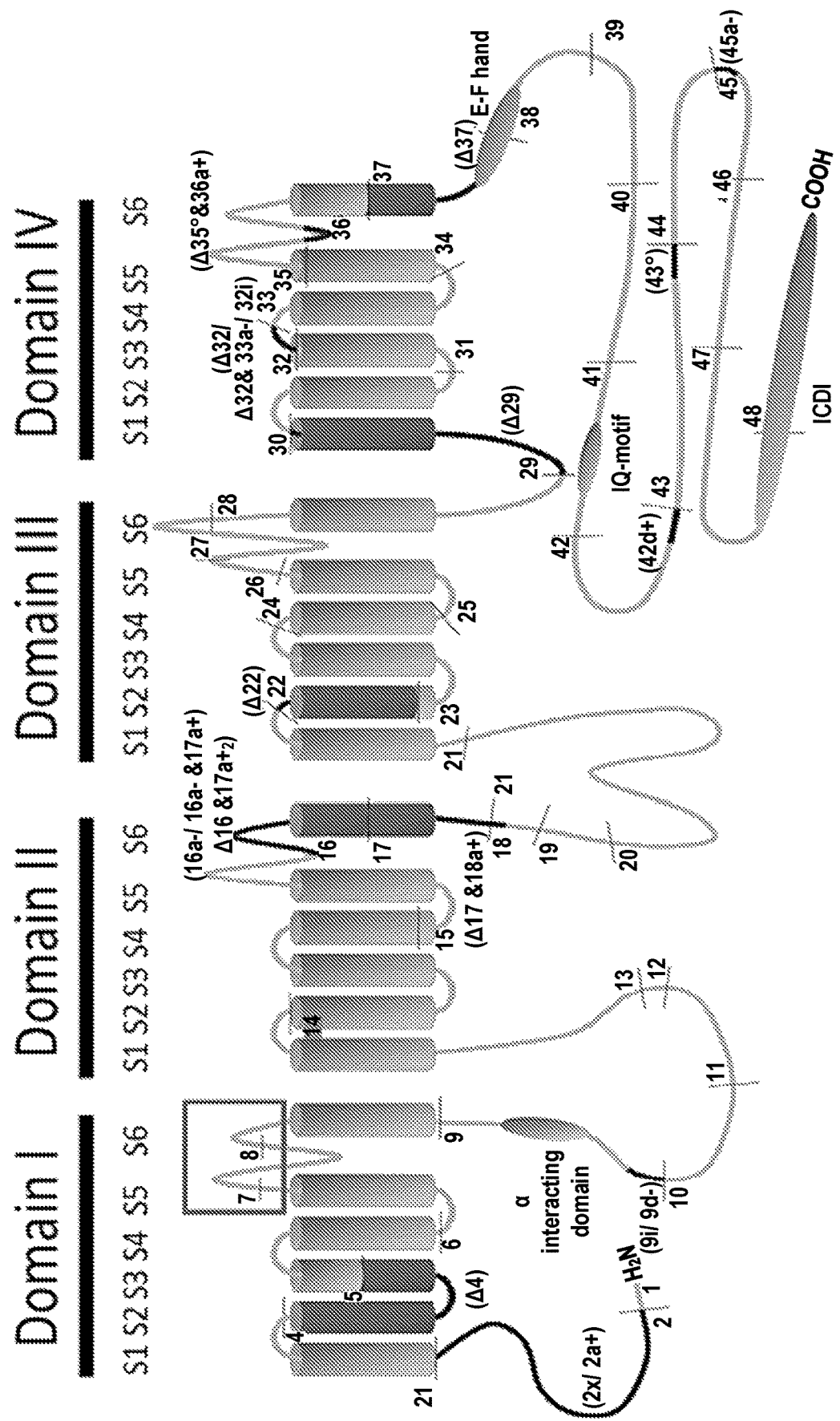
FIG. 1 shows a schematic of an alpha 1 subunit polypeptide of an L-type voltage-gated calcium channel. Transmembrane domains are represented by cylinders. Cytosolic domains are depicted below the transmembrane domains and extracellular domains are depicted above the transmembrane domains. The N-terminal is depicted at the bottom left and the C-terminal is depicted at the bottom right of the figure. Lines bisecting the polypeptide represent the borders of regions encoded by different exons of the messenger RNA. The Box indicates the extracellular domain of a pore loop between transmembrane segments S5 and S6 of domain I of the alpha 1 subunit.

Embodiments of the present disclosure include isolated antibodies, or antigen-binding fragments thereof, which specifically bind to an alpha 1 subunit of an L-type voltage-gated calcium channel, wherein the antibodies or antigen binding fragments thereof, (a) specifically bind to an amino acid sequence of an extracellular domain of a pore loop between transmembrane segments S5 and S6 of motif I of the alpha 1 subunit, or (b) competitively inhibits the binding of (a) to the alpha 1 subunit.

In certain embodiments, the L-type voltage-gated calcium channel is from human or mouse. In certain embodiments, the binding of the antibody or antigen binding fragment thereof to the alpha 1 subunit alters activity of the L-type voltage-gated calcium channel.

In certain embodiments, the L-type voltage-gated calcium channel is Cav1.4. In some embodiments, the amino acid sequence of the extracellular domain is GPGRPGDAPHTG [SEQ ID NO: 1], or is at least 90% identical to GPGRPGDAPHTG [SEQ ID NO: 1].

In certain embodiments, the L-type voltage-gated calcium channel is Cav1.3. In particular embodiments, the amino acid sequence of the extracellular domain is LTKETEGGNHSSGKSG [SEQ ID NO 2] or is at least 90% identical to LTKETEGGNHSSGKSG [SEQ ID NO 2].

In some embodiments, the L-type voltage-gated calcium channel is Cav1.2. In certain embodiments, the amino acid sequence of the extracellular domain is ATKADGANALGGKGA [SEQ ID NO: 3] at least 90% identical to ATKADGANALGGKGA [SEQ ID NO: 3].

In certain embodiments, the L-type voltage-gated calcium channel is Cav1.1. In certain embodiments, the amino acid sequence of the extracellular domain is PMQIELRHREWV$_H$ [SEQ ID NO 4] or is at least 90% identical to PMQIELRHREWV$_H$ [SEQ ID NO 4].

In some embodiments, the antibody or antigen-binding fragment binds to any of Cav1.4, Cav1.3, Cav1.2, or Cav1.1. In certain embodiments, the antibody or antigen-binding fragment thereof binds to any three of Cav1.4, Cav1.3, Cav1.2, or Cav1.1. In certain embodiments, the antibody or antigen-binding fragment thereof binds to any of Cav1.4, Cav1.3, or Cav1.2. In some embodiments, the antibody or antigen-binding fragment thereof binds to any of Cav1.4, Cav1.3, or Cav1.1. In certain embodiments, the antibody or antigen-binding fragment thereof binds to any of Cav1.4, Cav1.2, or Cav1.1. In certain embodiments, the antibody or antigen-binding fragment thereof binds to any of Cav1.3, Cav1.2, or Cav1.1. In certain embodiments, the antibody or antigen-binding fragment thereof binds to any two of Cav1.4, Cav1.3, Cav1.2, or Cav1.1. In certain embodiments, the antibody or antigen-binding fragment thereof binds Cav1.4 or Cav1.3. In certain embodiments, the antibody or antigen-binding fragment thereof binds Cav1.4 or Cav1.2. In some embodiments, the antibody or antigen-binding fragment thereof binds Cav1.4 or Cav1.1. In some embodiments, the antibody or antigen-binding fragment thereof binds Cav1.3 or Cav1.2. In particular embodiments, the antibody or antigen-binding fragment thereof binds Cav1.3 or Cav1.1. In specific embodiments, the antibody or antigen-binding fragment thereof binds Cav1.2 or Cav1.1. In certain embodiments, the antibody or antigen-binding fragment thereof binds only Cav1.4, that is, it does not significantly bind to Cav1.1, Cav1.2, or Cav1.3. In certain embodiments, the antibody or antigen-binding fragment thereof binds only Cav1.3, that is, it does not significantly bind to Cav1.1, Cav1.2, or Cav1.4. In certain embodiments, the antibody or antigen-binding fragment thereof binds only Cav1.2, that is, it does not significantly bind to Cav1.1, Cav1.3, or Cav1.4. In certain embodiments, the antibody or antigen-binding fragment thereof binds only Cav1.1, that is, it does not significantly bind to Cav1.2, Cav1.3, or Cav1.4.

In some embodiments, the isolated antibody, or antigen-binding fragment thereof, comprises a heavy chain variable region ($V_H$) that comprises $V_H$CDR1, $V_H$CDR2 and $V_H$CDR3 amino acid sequences; and/or a light chain variable region ($L_H$) that comprises $V_L$CDR1, $V_L$CDR2 and $V_L$CDR3 amino acid sequences, which are selected from:

(A) (i) $V_H$CDR1, $V_H$CDR2 and $V_H$CDR3 comprise, respectively, the amino acid sequences of SEQ ID NOS:14-16; and (ii) $V_L$CDR1, $V_L$CDR2 and $V_L$CDR3 comprise, respectively, the amino acid sequences of (i) SEQ ID NOS: 18-20; including variants thereof where at least one of said $V_H$CDR or $V_L$CDR amino acid sequences is modified by about 1, 2, or 3 amino acid substitutions, additions, or deletions;

(B) (i) $V_H$CDR1, $V_H$CDR2 and $V_H$CDR3 comprise, respectively, the amino acid sequences of SEQ ID NOS: 22-24; and (ii) $V_L$CDR1, $V_L$CDR2 and $V_L$CDR3 comprise, respectively, the amino acid sequences of (i) SEQ ID NOS: 26-28; including variants thereof where at least one of said $V_H$CDR or $V_L$CDR amino acid sequences is modified by about 1, 2, or 3 amino acid substitutions, additions, or deletions;

(C) (i) $V_H$CDR1, $V_H$CDR2 and $V_H$CDR3 comprise, respectively, the amino acid sequences of SEQ ID NOS:30-32; and (ii) $V_L$CDR1, $V_L$CDR2 and $V_L$CDR3 comprise, respectively, the amino acid sequences of (i) SEQ ID NOS: 34-36; including variants thereof where at least one of said $V_H$CDR or $V_L$CDR amino acid sequences is modified by about 1, 2, or 3 amino acid substitutions, additions, or deletions;

(D) (i) $V_H$CDR1 and $V_H$CDR2 comprise, respectively, the amino acid sequences of SEQ ID NOS:38-39; and (ii) $V_L$CDR1, $V_L$CDR2 and $V_L$CDR3 comprise, respectively, the amino acid sequences of (i) SEQ ID NOS: 42-44; including variants thereof where at least one of said $V_H$CDR or $V_L$CDR amino acid sequences is modified by about 1, 2, or 3 amino acid substitutions, additions, or deletions;

(E) (i) $V_H$CDR1, $V_H$CDR2 and $V_H$CDR3 comprise, respectively, the amino acid sequences of SEQ ID NOS: 46-48; and (ii) $V_L$CDR1, $V_L$CDR2 and $V_L$CDR3 comprise, respectively, the amino acid sequences of (i) SEQ ID NOS:50-52; including variants thereof where at least one of said $V_H$CDR or $V_L$CDR amino acid sequences is modified by about 1, 2, or 3 amino acid substitutions, additions, or deletions;

(F) (i) $V_H$CDR1 and $V_H$CDR2 comprise, respectively, the amino acid sequences of SEQ ID NOS:54-55; and (ii) $V_L$CDR1, $V_L$CDR2 and $V_L$CDR3 comprise, respectively, the amino acid sequences of (i) SEQ ID NOS: 58-60; including variants thereof where at least one of said $V_H$CDR or $V_L$CDR amino acid sequences is modified by about 1, 2, or 3 amino acid substitutions, additions, or deletions;

(G) (i) $V_H$CDR1, $V_H$CDR2 and $V_H$CDR3 comprise, respectively, the amino acid sequences of SEQ ID NOS: 62-64; including variants thereof where at least one of said $V_H$CDR or $V_L$CDR amino acid sequences is modified by about 1, 2, or 3 amino acid substitutions, additions, or deletions;

(H) (i) $V_H$CDR1, $V_H$CDR2 and $V_H$CDR3 comprise, respectively, the amino acid sequences of SEQ ID NOS: 70-72; and (ii) $V_L$CDR1, $V_L$CDR2 and $V_L$CDR3 comprise, respectively, the amino acid sequences of (i) SEQ ID NOS: 74-76; including variants thereof where at least one of said $V_H$CDR or $V_L$CDR amino acid sequences is modified by about 1, 2, or 3 amino acid substitutions, additions, or deletions;

(I) (i) $V_H$CDR1, $V_H$CDR2 and $V_H$CDR3 comprise, respectively, the amino acid sequences of SEQ ID NOS:78-80; and (ii) $V_L$CDR1, $V_L$CDR2 and $V_L$CDR3 comprise, respectively, the amino acid sequences of (i) SEQ ID NOS:82-84; including variants thereof where at least one of said $V_H$CDR or $V_L$CDR amino acid sequences is modified by about 1, 2, or 3 amino acid substitutions, additions, or deletions;

(J) (i) $V_H$CDR1, $V_H$CDR2 and $V_H$CDR3 comprise, respectively, the amino acid sequences of SEQ ID NOS: 86-88; and (ii) $V_L$CDR1, $V_L$CDR2 and $V_L$CDR3 comprise, respectively, the amino acid sequences of (i) SEQ ID NOS:90-92; including variants thereof where at least one of said $V_H$CDR or $V_L$CDR amino acid sequences is modified by about 1, 2, or 3 amino acid substitutions, additions, or deletions;

(K) (i) $V_L$CDR1, $V_L$CDR2 and $V_L$CDR3 comprise, respectively, the amino acid sequences of (i) SEQ ID NOS: 98-100; including variants thereof where at least one of said $V_H$CDR or $V_L$CDR amino acid sequences is modified by about 1, 2, or 3 amino acid substitutions, additions, or deletions; and (L) (i) $V_L$CDR1, $V_L$CDR2 and $V_L$CDR3 comprise, respectively, the amino acid sequences of (i) SEQ ID NOS: 106-108; including variants thereof where at least one of said $V_H$CDR or $V_L$CDR amino acid sequences is modified by about 1, 2, or 3 amino acid substitutions, additions, or deletions.

In certain embodiments, the antibody, or antigen-binding fragment thereof, comprises a $V_H$ sequence that is at least 90% identical to SEQ ID NO:13, 21, 29, 37, 45, 53, 61, 69, 77, or 85.

In certain embodiments, antibody, or antigen-binding fragment thereof, comprises a $V_L$ sequence that is at least 90% identical to SEQ ID NO:17, 25, 33, 41, 49, 57, 73, 81, 89, 97, or 105.

In some embodiments, the antibody, or antigen-binding fragment thereof, comprises a $V_H$ sequence that is at least 90% identical to SEQ ID NO: 13, 21, 29, 37, 45, 53, 61, 69, 77, or 85, and a $V_L$ sequence that is at least 90% identical to SEQ ID NO: 17, 25, 33, 41, 49, 57, 73, 81, 89, 97, or 105.

In particular embodiments, the antibody, or antigen-binding fragment thereof, comprises a $V_H$ sequence and a $V_L$ sequence selected from:
(A) the $V_H$ sequence of SEQ ID NO: 13 and the $V_L$ sequence of SEQ ID NO:17;
(B) the $V_H$ sequence of SEQ ID NO: 21 and the $V_L$ sequence of SEQ ID NO:25;
(C) the $V_H$ sequence of SEQ ID NO:29 and the $V_L$ sequence of SEQ ID NO:33;
(D) the $V_H$ sequence of SEQ ID NO:37 and the $V_L$ sequence of SEQ ID NO:41;
(E) the $V_H$ sequence of SEQ ID NO:45 and the $V_L$ sequence of SEQ ID NO:49;
(F) the $V_H$ sequence of SEQ ID NO:53 and the $V_L$ sequence of SEQ ID NO:57;
(G) the $V_H$ sequence of SEQ ID NO:69 and the $V_L$ sequence of SEQ ID NO:73;
(H) the $V_H$ sequence of SEQ ID NO: 77 and the $V_L$ sequence of SEQ ID NO:81;
(I) the $V_H$ sequence of SEQ ID NO:85 and the $V_L$ sequence of SEQ ID NO:89; and
(J) a variant $V_H$ sequence and a variant VI sequence that is at least 90% identical to any of (A)-(I).

Also included are polynucleotides that encode the antibodies, or antigen-binding fragments thereof, described herein, vectors that comprise such polynucleotides, and host cells that comprise and optionally express the polynucleotides and/or vectors.

Also included are methods for modulating a function of a cell expressing an L-type voltage-gated calcium channel comprising contacting the cell with an antibody, or antigen-binding fragment thereof, which specifically binds to (a) an amino acid sequence of an extracellular domain of a pore loop between transmembrane segments S5 and S6 of domain 1 of an alpha 1 subunit of the L-type voltage-gated calcium channel, or (b) competitively inhibits the binding of (a) to the alpha 1 subunit, wherein binding of the agent to the alpha I subunit modulates the activity of the L-type voltage-gated calcium channel.

In certain embodiments, the antibody or binding fragment thereof is an antibody or binding fragment described herein. In certain embodiments, the cell is a hematopoietic cell. In certain embodiments, the antibody or antigen binding-fragment thereof inhibits the activity of the L-type voltage-gated calcium channel. In certain embodiments, the antibody or antigen binding-fragment thereof increases the activity of the L-type voltage-gated calcium channel. In certain embodiments, the cell is a hematopoietic cell of the lymphoid lineage.

In certain embodiments, the cell is a T cell. In certain embodiments, the function of the cell comprises T cell maturation. In certain embodiments, the function of the cell comprises antigen binding.

In certain embodiments, the cell is a B cell. In certain embodiments, the function of the cell comprises B cell maturation. In certain embodiments, the function of the cell comprises B cell receptor-induced activation.

In certain embodiments, the L-type voltage-gated calcium channel is Cav1.4. In certain embodiments, the L-type voltage-gated calcium channel is Cav1.3. In certain embodiments, the L-type voltage-gated calcium channel is Cav1.2. In certain embodiments, the L-type voltage-gated calcium channel is Cav1.1.

Some embodiments relate to methods of modulating an immune response in a subject comprising administering to the subject an effective amount of an antibody, or antigen-binding fragment thereof, which specifically binds to (a) an amino acid sequence of an extracellular domain of a pore loop between transmembrane segments S5 and S6 of domain 1 of an alpha 1 subunit of the L-type voltage-gated calcium channel, or (b) competitively inhibits the binding of (a) to the alpha 1 subunit, wherein the L-type voltage-gated calcium channel is expressed in a hematopoietic cell.

In certain embodiments, the antibody or binding fragment thereof is an antibody or binding fragment thereof described herein. In certain embodiments, the hematopoietic cell is of the lymphoid lineage. In certain embodiments, the hematopoietic cell is a T cell or a B cell.

In certain embodiments, the L-type voltage-gated calcium channel is Cav1.4. In certain embodiments, the L-type voltage-gated calcium channel is Cav1.3. In certain embodiments, the L-type voltage-gated calcium channel is Cav1.2. In certain embodiments, the L-type voltage-gated calcium channel is Cav1.1.

Also included are methods of inhibiting an immune response in a subject comprising administering to the subject an effective amount of an antibody, or antigen-binding fragment thereof, which specifically binds to (a) an amino acid sequence of an extracellular domain of a pore loop between transmembrane segments S5 and S6 of domain 1 of an alpha 1 subunit of the L-type voltage-gated calcium channel, or (b) competitively inhibits the binding of (a) to the alpha 1 subunit, wherein the L-type voltage-gated calcium channel is expressed in a hematopoietic cell.

In certain embodiments, the antibody or binding fragment thereof is an antibody or binding fragment thereof described herein. In certain embodiments, the hematopoietic cell is of the lymphoid lineage. In certain embodiments, the hematopoietic cell is a T cell. In certain embodiments, administering the effective amount of the antibody or antigen-binding fragment thereof decreases T cell receptor-induced $Ca^{2+}$ fluxes. In certain embodiments, administering the effective amount of the antibody or antigen-binding fragment thereof reduces naïve T cell survival.

In certain embodiments, administering the effective amount of the antibody or antigen-binding fragment reduces CD3/CD28 induced T cell proliferation. In certain embodiments, the hematopoietic cell is a B cell.

In certain embodiments, administering the effective amount of the antibody or antigen-binding fragment inhibits B cell receptor-induced activation.

In certain embodiments, the L-type voltage-gated calcium channel is Cav1.4. In certain embodiments, the L-type voltage-gated calcium channel is Cav1.3. In certain embodiments, the L-type voltage-gated calcium channel is Cav1.2. In certain embodiments, the L-type voltage-gated calcium channel is Cav1.1.

Also included are methods of treating a disease in a subject comprising administering to the subject an effective amount of an antibody, or antigen-binding fragment thereof, which specifically binds to (a) an amino acid sequence of an extracellular domain of a pore loop between transmembrane segments S5 and S6 of domain 1 of an alpha 1 subunit of the L-type voltage-gated calcium channel, or (b) competitively inhibits the binding of (a) to the alpha 1 subunit.

In certain embodiments, the antibody or binding fragment thereof is an antibody or binding fragment thereof described herein.

In some embodiments, the disease is an inflammatory disease. In particular embodiments, the inflammatory disease is X-linked agammaglobulinemia, systemic lupus erythematosus, inflammatory (rheumatoid) arthritis, Hashimoto's thyroiditis, pernicious anemia, inflammatory bowel disease (Crohn's disease and ulcerative colitis), psoriasis, renal fibroses, pulmonary fibroses, hepatic fibroses, Addison's disease, Type I diabetes, systemic lupus erythematosus (SLE), dermatomyositis, Sjogren's syndrome, multiple sclerosis, myasthenia gravis, Reiter's syndrome, asthma, or Grave's disease.

In some embodiments, the disease is a cancer. In certain embodiments, the cancer is a hematopoietic cancer. In some embodiments, hematopoietic cancer is a lymphoma, leukemia, or multiple myeloma.

In specific embodiments, the lymphoma is a T-cell lymphoma, B-cell lymphoma, small lymphocytic lymphoma, mangle cell lymphoma, anaplastic large cell lymphoma (ALCL), follicular lymphoma, Hodgkin's lymphoma, or non-Hodgkin's lymphoma. In some embodiments, the leukemia is chronic lymphocytic leukemia (CLL), hairy cell leukemia, acute lymphoblastic leukemia, myelocytic leukemia, acute myeloid or myelogenous leukemia, or chronic myelogenous leukemia.

In some embodiments, the cancer is selected from one or more of breast cancer, cervical cancer, prostate cancer, gastrointestinal cancer, lung cancer, ovarian cancer, testicular cancer, head and neck cancer, bladder cancer, kidney cancer (e.g., renal cell carcinoma), soft tissue sarcoma, squamous cell carcinoma, CNS or brain cancer, melanoma, non-melanoma cancer, thyroid cancer, endometrial cancer, an epithelial tumor, and bone cancer.

In some embodiments, the cancer (cell) expresses or overexpresses Cav1.1, Cav1.2, Cav1.3, Cav1.4, or any combination thereof. In particular embodiments, the cancer expresses or overexpresses Cav1.1 and the antibody, or antigen-binding fragment thereof, specifically binds to Cav1.1. In certain embodiments, the cancer expresses or overexpresses Cav1.2 and the antibody, or antigen-binding fragment thereof, specifically binds to Cav1.2. In some embodiments, the cancer expresses or overexpresses Cav1.3 and the antibody, or antigen-binding fragment thereof, specifically binds to Cav1.3. In particular embodiments, the cancer expresses or overexpresses Cav1.4 and the antibody, or antigen-binding fragment thereof, specifically binds to Cav1.4.

DETAILED DESCRIPTION

Unless defined otherwise, all technical and scientific terms used herein have the same meaning as commonly understood by those of ordinary skill in the art to which the invention belongs. Although any methods and materials similar or equivalent to those described herein can be used in the practice or testing of the present invention, preferred methods and materials are described. For the purposes of the present invention, the following terms are defined below. All of the patent and non-patent literature references listed herein are incorporated by reference in their entireties.

The articles "a" and "an" are used herein to refer to one or to more than one (i.e., to at least one) of the grammatical object of the article. By way of example, "an element" means one element or more than one element.

By "about" is meant a quantity, level, value, number, frequency, percentage, dimension, size, amount, weight or length that varies by as much as 30, 25, 20, 15, 10, 9, 8, 7, 6, 5, 4, 3, 2 or 1% to a reference quantity, level, value, number, frequency, percentage, dimension, size, amount, weight or length.

As used herein, the term "amino acid" is intended to mean both naturally occurring and non-naturally occurring amino acids as well as amino acid analogs and mimetics. Naturally occurring amino acids include the 20 (L)-amino acids utilized during protein biosynthesis as well as others such as 4-hydroxyproline, hydroxylysine, desmosine, isodesmosine, homocysteine, citrulline and ornithine, for example. Non-naturally occurring amino acids include, for example, (D)-amino acids, norleucine, norvaline, p-fluorophenylalanine, ethionine and the like, which are known to a person skilled in the art. Amino acid analogs include modified forms of naturally and non-naturally occurring amino acids. Such modifications can include, for example, substitution or replacement of chemical groups and moieties on the amino acid or by derivatization of the amino acid. Amino acid mimetics include, for example, organic structures which exhibit functionally similar properties such as charge and charge spacing characteristic of the reference amino acid. For example, an organic structure which mimics Arginine (Arg or R) would have a positive charge moiety located in similar molecular space and having the same degree of mobility as the ε-amino group of the side chain of the naturally occurring Arg amino acid. Mimetics also include constrained structures so as to maintain optimal spacing and charge interactions of the amino acid or of the amino acid functional groups. Those skilled in the art know or can determine what structures constitute functionally equivalent amino acid analogs and amino acid mimetics.

Throughout this specification, unless the context requires otherwise, the words "comprise," "comprises," and "comprising" will be understood to imply the inclusion of a stated step or element or group of steps or elements but not the exclusion of any other step or element or group of steps or elements. By "consisting of" is meant including, and limited to, whatever follows the phrase "consisting of." Thus, the phrase "consisting of" indicates that the listed elements are required or mandatory, and that no other elements may be present. By "consisting essentially of" is meant including any elements listed after the phrase, and limited to other elements that do not interfere with or contribute to the activity or action specified in the disclosure for the listed elements. Thus, the phrase "consisting essentially of" indicates that the listed elements are required or mandatory, but that other elements are optional and may or may not be present depending upon whether or not they materially affect the activity or action of the listed elements.

The term "biological sample" includes a biological material that can be collected from a subject and used in connection with diagnosis or monitoring of biological states. Biological samples can include clinical samples, including body fluid samples, such as body cavity fluids, urinary fluids, cerebrospinal fluids, blood, and other liquid samples of biological origin; and tissue samples, such as biopsy samples, tumor or suspected tumor samples, and other solid samples of biological origin. Biological samples can also include those that are manipulated in some way after their collection, such as by treatment with reagents, culturing, solubilization, enrichment for certain biological constituents, cultures or cells derived therefrom, and the progeny thereof.

The term "conjugate" includes an entity formed as a result of covalent or non-covalent attachment or linkage of an agent or other molecule, e.g., a detectable entity, a biologically active molecule, PEG or other polymer, to an antibody described herein.

A "control" such as a "control subject" or "control tissue" includes a healthy subject or a healthy tissue sample, for example, which is not pathological or diseased. In certain embodiments, a control includes a non-diseased tissue from a different, healthy subject or the same subject being tested or diagnosed. A control can also include a reference standard, for example, a standard value generated from one or more healthy subjects or tissues.

As used herein, the terms "function" and "functional" and the like refer to a biological, enzymatic, or therapeutic function.

An "effective amount" is an amount sufficient to effect beneficial or desired results. For example, a therapeutic amount is one that achieves the desired therapeutic effect. This amount can be the same or different from a prophylactically effective amount, which is an amount necessary to prevent onset of disease or disease symptoms. An effective amount can be administered in one or more administrations, applications or dosages. A therapeutically effective amount of a composition depends on the composition selected. The compositions can be administered one from one or more times per day to one or more times per week; including once every other day. The skilled artisan will appreciate that certain factors may influence the dosage and timing required to effectively treat a subject, including but not limited to the severity of the disease or disorder, previous treatments, the general health and/or age of the subject, and other diseases present. Moreover, treatment of a subject with a therapeutically effective amount of the compositions of the invention can include a single treatment or a series of treatments.

"Homology" refers to the percentage number of amino acids that are identical or constitute conservative substitutions. Homology may be determined using sequence comparison programs such as GAP (Deveraux et al., Nucleic Acids Research. 12, 387-395, 1984), which is incorporated herein by reference. In this way sequences of a similar or substantially different length to those cited herein could be compared by insertion of gaps into the alignment, such gaps being determined, for example, by the comparison algorithm used by GAP.

By "isolated" is meant material that is substantially or essentially free from components that normally accompany it in its native state. For example, an "isolated peptide" or an "isolated polypeptide" and the like, as used herein, includes the in vitro isolation and/or purification of a peptide or polypeptide molecule from its natural cellular environment, and from association with other components of the cell; i.e., it is not significantly associated with in vivo substances. In particular embodiments, the isolated polypeptide is an antibody.

A "decreased" or "reduced" amount is typically a "statistically significant" amount, and may include, for example, a 5%, 6%, 7%, 8%, 9%, 10%, 11%, 12%, 13%, 14%, 15%, 16%, 17%, 18%, 19%, 20%, 25%, 30%, 35%, 40%, 45%, 50%, 55%, 60%, 65%, 70%, 75%, 80%, 85%, 90%, 95%, or 100% decrease (including all integers and ranges in between) relative to a control. Other examples of comparisons and "statistically significant" amounts are described herein. "Decrease," as used herein, can refer to "inhibit," "reduce," "curb," "abate," "diminish," "lessen," "lower," or "weaken."

A "increased" or "enhanced" amount is typically a "statistically significant" amount, and may include, for example, a 5%, 6%, 7%, 8%, 9%, 10%, 11%, 12%, 13%, 14%, 15%, 16%, 17%, 18%, 19%, 20%, 25%, 30%, 35%, 40%, 45%, 50%, 55%, 60%, 65%, 70%, 75%, 80%, 85%, 90%, 95%, or 100% increase. An increased or enhanced amount may also include a 2-fold, 3, fold, 4 fold, 5 fold, 6 fold, 7 fold, 8-fold, 9-fold, 10 fold, 20-fold, 30 fold, 40 fold, 50 fold, 60 fold 70 fold, 80-fold, 90-fold, 100-fold, 200-fold, 300-fold, 400-fold, 500-fold, 1,000-fold, 10,000-fold, or greater than 10,000-fold increase (including all integers and ranges in between) relative to a control. Other examples of comparisons and "statistically significant" amounts are described herein. "Increase," as used herein, can refer to "agonize," "enhance," "inflate," "escalate," expand," "augment," "enlarge," or "raise."

In certain embodiments, the "purity" of any given agent (e.g., an antibody) in a composition may be specifically defined. For instance, certain compositions may comprise an agent that is at least 80%, 85%, 90%, 91%, 92%, 93%, 94%, 95%, 96%, 97%, 98%, 99%, or 100% pure, including all decimals in between, as measured, for example, and by no means limiting, by high performance liquid chromatography (HPLC), a well-known form of column chromatography used frequently in biochemistry and analytical chemistry to separate, identify, and quantify compounds.

The terms "polypeptide" and "protein" are used interchangeably herein to refer to a polymer of amino acid residues and to variants and synthetic analogues of the same. Thus, these terms apply to amino acid polymers in which one or more amino acid residues are synthetic non-naturally occurring amino acids, such as a chemical analogue of a corresponding naturally occurring amino acid, as well as to naturally-occurring amino acid polymers. The polypeptides described herein are not limited to a specific length of the product; thus, peptides, oligopeptides, and proteins are included within the definition of polypeptide, and such terms may be used interchangeably herein unless specifically indicated otherwise. The polypeptides described herein may also comprise post-expression modifications, such as glycosylations, acetylations, phosphorylations and the like, as well as other modifications known in the art, both naturally occurring and non-naturally occurring. A polypeptide may be an entire protein, or a subsequence, fragment, variant, or derivative thereof.

The term "reference sequence" refers generally to a nucleic acid coding sequence, or amino acid sequence, to which another sequence is being compared. All polypeptide and polynucleotide sequences described herein are included as references sequences, including those described by name and those described in the Tables and the Sequence Listing.

The terms "sequence identity" or, for example, comprising a "sequence 50% identical to," as used herein, refer to the extent that sequences are identical on a nucleotide-by-nucleotide basis or an amino acid-by-amino acid basis over a window of comparison. Thus, a "percentage of sequence identity" may be calculated by comparing two optimally aligned sequences over the window of comparison, determining the number of positions at which the identical nucleic acid base (e.g., A, T, C, G, I) or the identical amino acid residue (e.g., Ala, Pro, Ser, Thr, Gly, Val, Leu, Ile, Phe, Tyr, Trp, Lys, Arg, His, Asp, Glu, Asn, Gln, Cys and Met) occurs in both sequences to yield the number of matched positions, dividing the number of matched positions by the total number of positions in the window of comparison (i.e., the window size), and multiplying the result by 100 to yield the percentage of sequence identity. Included are nucleotides and polypeptides having at least about 50%, 55%, 60%, 65%, 70%, 75%, 80%, 85%, 90%, 95%, 97%, 98%, 99% or 100% sequence identity to any of the reference sequences described herein (see, e.g., Sequence Listing), typically where the polypeptide variant maintains at least one biological activity of the reference polypeptide.

Terms used to describe sequence relationships between two or more polynucleotides or polypeptides include "reference sequence," "comparison window," "sequence identity," "percentage of sequence identity," and "substantial identity." A "reference sequence" is at least 12 but frequently 15 to 18 and often at least 25 monomer units, inclusive of nucleotides and amino acid residues, in length. Because two polynucleotides may each comprise (1) a sequence (i.e., only a portion of the complete polynucleotide sequence) that is similar between the two polynucleotides, and (2) a sequence that is divergent between the two polynucleotides, sequence comparisons between two (or more) polynucleotides are typically performed by comparing sequences of the two polynucleotides over a "comparison window" to identify and compare local regions of sequence similarity. A "comparison window" refers to a conceptual segment of at least 6 contiguous positions, usually about 50 to about 100, more usually about 100 to about 150 in which a sequence is compared to a reference sequence of the same number of contiguous positions after the two sequences are optimally aligned. The comparison window may comprise additions or deletions (i.e., gaps) of about 20% or less as compared to the reference sequence (which does not comprise additions or deletions) for optimal alignment of the two sequences. Optimal alignment of sequences for aligning a comparison window may be conducted by computerized implementations of algorithms (GAP, BESTFIT, FASTA, and TFASTA in the Wisconsin Genetics Software Package Release 7.0, Genetics Computer Group, 575 Science Drive Madison, WI, USA) or by inspection and the best alignment (i.e., resulting in the highest percentage homology over the comparison window) generated by any of the various methods selected. Reference also may be made to the BLAST family of programs as for example, disclosed by Altschul et al., Nucl. Acids Res. 25:3389, 1997. A detailed discussion of sequence analysis can be found in Unit 19.3 of Ausubel et al., "Current Protocols in Molecular Biology," John Wiley & Sons Inc, 1994-1998, Chapter 15.

By "significant" or "statistically significant," it is meant that the result was unlikely to have occurred by chance. Statistical significance can be determined by any method known in the art. Commonly used measures of significance include the p-value, which is the frequency or probability with which the observed event would occur, if the null hypothesis were true. If the obtained p-value is smaller than the significance level, then the null hypothesis is rejected. In simple cases, the significance level is defined at a p-value of 0.05 or less.

The term "solubility" refers to the property of an antibody described herein to dissolve in a liquid solvent and form a homogeneous solution. Solubility is typically expressed as a concentration, either by mass of solute per unit volume of solvent (g of solute per kg of solvent, g per dL (100 mL), mg/mL, etc.), molarity, molality, mole fraction or other similar descriptions of concentration. The maximum equilibrium amount of solute that can dissolve per amount of solvent is the solubility of that solute in that solvent under the specified conditions, including temperature, pressure, pH, and the nature of the solvent. In certain embodiments, solubility is measured at physiological pH, or other pH, for example, at pH 5.0, pH 6.0, pH 7.0, or pH 7.4. In certain embodiments, solubility is measured in water or a physiological buffer such as PBS or NaCl (with or without NaP). In specific embodiments, solubility is measured at relatively lower pH (e.g., pH 6.0) and relatively higher salt (e.g., 500 mM NaCl and 10 mM NaP). In certain embodiments, solubility is measured in a biological fluid (solvent) such as blood or serum. In certain embodiments, the temperature can be about room temperature (e.g., about 20, 21, 22, 23, 24, 25° C.) or about body temperature (~37° C.). In certain embodiments, an antibody has a solubility of at least about 0.1, 0.2, 0.3, 0.4, 0.5, 0.6, 0.7, 0.8, 0.9, 1, 2, 3, 4, 5, 6, 7, 8, 9, 10, 11, 12, 13, 14, 15, 16, 17, 18, 19, 20, 25, or 30 mg/ml at room temperature or at about 37° C.

A "subject," as used herein, includes any animal that exhibits a symptom or condition, or is at risk for or suspected of exhibiting a symptom or condition, which can be diagnosed with an antibody described herein. Suitable subjects (patients) include laboratory animals (such as mouse, rat, rabbit, or guinea pig), farm animals, and domestic animals or pets (such as a cat or dog). Nonhuman primates and, preferably, human patients, are included.

A "subject subpopulation" or "patient subpopulation," as used herein, includes a subject or patient subset characterized as having one or more distinctive measurable and/or identifiable characteristics that distinguishes the subject or patient subset from others in the broader disease category (e.g., cancer) to which it belongs. Such characteristics include disease subcategories, gender, lifestyle, health history, organs/tissues involved, treatment history, etc. In some embodiments, a patient or subject subpopulation is characterized by the (e.g., reduced) amount or levels of an L-type voltage-gated calcium channel alpha 1 subunit polypeptide in a biological sample, for example, a tumor sample.

"Substantially" or "essentially" means nearly totally or completely, for instance, 95%, 96%, 97%, 98%, 99% or greater of some given quantity.

"Substantially free" refers to the nearly complete or complete absence of a given quantity for instance, less than about 10%, 5%, 4%, 3%, 2%, 1%, 0.5% or less of some given quantity. For example, certain compositions may be "substantially free" of cell proteins, membranes, nucleic acids, endotoxins, or other contaminants.

"Treatment" or "treating," as used herein, includes any desirable effect on the symptoms or pathology of a disease or condition, and may include even minimal changes or improvements in one or more measurable markers of the disease or condition being treated. "Treatment" or "treating" does not necessarily indicate complete eradication or cure of the disease or condition, or associated symptoms thereof. The subject receiving this treatment is any subject in need thereof. Exemplary markers of clinical improvement will be apparent to persons skilled in the art.

The term "wild-type" refers to a gene or gene product that has the characteristics of that gene or gene product when isolated from a naturally-occurring source. A wild-type gene or gene product (e.g., a polypeptide) is that which is most frequently observed in a population and is thus arbitrarily designed the "normal" or "wild-type" form of the gene.

L-Type Voltage-Gated Calcium Channels

Voltage-gated calcium channels mediate calcium influx in response to membrane depolarization and regulate intracellular processes such as contraction, secretion, neurotransmission, and gene expression in many different cell types. Voltage-gated calcium channels couple electrical events that alter membrane potential at the cell surface to physiological processes in the cells. Voltage-gated calcium channels are members of a gene superfamily of transmembrane ion channel proteins that includes voltage-gated potassium and sodium channels.

Calcium currents recorded in different cell types have diverse physiological and pharmacological properties, and so voltage-gated calcium channels are grouped based on the properties of their respective currents. In general, L-type voltage-gated calcium channels open in response to a strong depolarization and produce long-lasting calcium current. L-type voltage-gated calcium channels are blocked by organic L-type calcium channel antagonists, including dihydropyridines, phenylalkylamines, and benzothiazepines. L-type voltage-gated calcium channels generate the main calcium currents recorded in muscle and endocrine cells, where they initiate contraction and secretion. L-type currents activating at lower voltages also exist predominantly in neurons and cardiac pacemaker cells. L-type voltage-gated calcium channels are also expressed in cells that are not considered excitable, including in hematopoietic cells such as T cells and B cells.

The L-type voltage-gated calcium channels are complex proteins composed of four or five distinct subunits that are encoded by multiple genes. The α1 subunit of 190 to 250 kDa is the largest subunit, and it incorporates the conduction pore, the voltage sensor and gating apparatus, and most of the known sites of channel regulation by secondary messengers, drugs, and toxins. A particular L-type voltage-gated channel will take its name (i.e. Cav1.4) from the alpha 1 subunit it contains. Like the alpha subunits of sodium channels, the alpha 1 subunit of voltage gated calcium channels is organized in four homologous domains (I-IV), also called motifs, with six transmembrane segments (S1-S6) in each. The transmembrane segments of each domain are numbered in the order they are arranged from the N-terminal to the C-terminal.

The alpha 1 subunit forms the channel structure of the voltage-gated calcium channel protein. The pore of the calcium channel is formed at the center of a pseudo-symmetric arrangement of the four domains, and the pore loops between S5 and S6 of each domain form the narrow, extracellular end of the channel. These pore loops determine ion conductance and selectivity, and changes of only three specific amino acids in the pore loops in domains I, III, and IV will convert a channel's selectivity from calcium ions to sodium ions. The S4 segments of each domain serve as the channel's voltage sensor. An intracellular beta subunit and a transmembrane, disulfide-linked alpha2 beta subunit complex are components of most types of calcium channels. A gamma subunit has also been found in skeletal muscle calcium channels, and related subunits are expressed in heart and brain. Although these auxiliary subunits modulate the properties of the channel complex, the pharmacological and electrophysiological diversity of calcium channels arises primarily from the α1 subunits.

The opening and closing of the voltage-gated calcium channels are primarily gated by changes in membrane potential, which cause movement of charges across the membrane and drive conformational changes that open and close the pore. The positively charged S4 segments are thought to undergo outward and rotational movement through the protein structure during the gating process, as proposed in the 'sliding helix' and 'helical screw' models of gating (Reviewed in Catterall et al, (2007) Toxicol. 49(2), pp 124-141). This structure suggests that the pore is closed at its intracellular end and discriminates ions at the narrow ion selectivity filter at its extracellular end.

L-type voltage-gated calcium channels are found in populations of cells considered to be excitable. Excitable cells are cells where specific stimulations can trigger changes in the membrane potential globally throughout the cell or locally in a region of the cell. Calcium channels can function to regulate the changes in membrane potential. Additionally, calcium ions that enter the cytosol when calcium channels are open can act as a secondary messenger that can continue to regulate cellular processes after the depolarization event. Expression of L-type voltage calcium channels are also found in cells not considered to be excitable.

At least four subtypes of L-type voltage-gated calcium channels have been described. These subtypes are categorized by the alpha 1 subunits they contain, which are each encoded by separate genes. The gene encoding Cav1.4 is CACNA1F. High levels of Cav1.4 are found in retina, spleen, thymus, and bone marrow. Cav1.3 is encoded by CACNA1D, and is found in brain, pancreas, kidney, ovary, and cochlea. Cav1.2 is encoded by CACNA1C, and shows high expression in heart, smooth muscle, brain, pituitary and adrenal glands. Cav1.1 is encoded by CACNA1S, and has high levels of expression in skeletal muscle.

Data from mouse and human studies demonstrate that each L-type voltage gated calcium channel subtype is found in immune cells (Reviewed in Omilusik et al (2013) Frontiers in Immunology, vol 4:164). Cav1.4 expression has been observed in the human Jurkat T cell line, as well as in human and rat spleen and thymus, and human and mouse T cells. Cav1.3 expression has been observed in the human Jurkat T cell line, and in mouse T cells. Cav1.2 expression has been observed in human peripheral blood T cells, as well as in the human Jurkat, MOLT-4, and CEM T cell lines. Cav1.2 has also been reported in mouse T cells. Cav1.1 has been observed in mouse T cells. The expression profile of these subtypes suggests that L-type voltage-gated calcium channels participate in regulation of calcium signaling in immune cells.

Antibodies

Certain embodiments relate to isolated antibodies which specifically bind to a human or mouse alpha 1 subunit of one or more L-type voltage-gated calcium channels, including those that specifically bind to one or more contiguous or non-contiguous fragments or epitopes thereof. In some embodiments, the antibodies or antigen-binding fragments thereof specifically bind to an extracellular domain of an L-type voltage-gated calcium channel alpha 1 subunit. In particular embodiments, the antibodies or antigen-binding fragments thereof specifically bind to an amino acid sequence of an alpha 1 subunit that resides in an extracellular domain of a pore loop between segments S5 and S6 of a domain in an alpha 1 subunit of an L-type voltage-gated calcium channel. In some embodiments, the pore loop is located in domain I of the alpha 1 subunit. This region is encoded by exons 7 and 8 of the messenger RNA encoding the alpha 1 subunit. In some embodiments, the antibody or antigen-binding fragment thereof prevents the binding of a second antibody to the extracellular pore loop between S5 and S6 of domain I of the alpha 1 subunit of the voltage-gated calcium-channel. In some embodiments, the alpha 1 subunit can be of human or mouse origin. In certain embodiments, the antibody is monoclonal.

In some embodiments, the antibody or antigen-binding fragment thereof described herein modulates the activity of the L-type gated voltage calcium channel. "Modulate," as used herein, can refer to "alter," "modify," "change," "shift," "transform," or "adjust." The alterations may be in the form of an increase or a decrease of channel activity, or a combination of both. An example of altering activity that comprises a combination of increasing and decreasing activity is an antibody that functions as an inverse agonist, where upon the binding of the antibody to the voltage-gated calcium channel would result in an initial brief increase in channel activity, followed by a sustained decrease in channel activity.

"Activity," as used herein, of the L-type voltage-gated calcium channel refers to the calcium conductance of the channel. The L-type voltage-gated calcium channel is considered to be in a closed conformation at resting membrane conditions. "Closed" refers to a conformation of the channel where there is little or no calcium conductance. When the plasma membrane becomes depolarized, the channel adopts an open conformation which allows for calcium conductance. Following the membrane depolarization, the channel remains open for a time before reverting back to a closed conformation. "Open" refers to a conformation where calcium ions are permitted to pass through the channel. An L-type voltage-gated calcium channel can have one or more open and closed conformations. In some embodiments, an antibody or antigen binding fragment thereof specifically binds to the alpha 1 subunit of the voltage gated calcium channel and alters its activity. This effect may be achieved by, for example but not limited to, changing the probability that the channel will be in an open or closed conformation, changing the conditions, such as the degree of membrane depolarization, that changes the conformation of the channel, changing the duration of time that the calcium channel remains in an open or closed state, changing the calcium conductance of the channel when it is in an open or closed state, or any combination thereof. In some embodiments, inhibiting activity of an L-type voltage-gated calcium channel is achieved by reducing the probability that the channel will adopt an open conformation in response to membrane depolarization, increasing the degree of membrane depolarization required to shift the channel into an open conformation, decreasing the duration of time the channel remains in an open conformation following depolarization of the plasma membrane, reducing the calcium conductance of the channel when it is in an open conformation, or any combination thereof.

In some embodiments, the antibody or antigen-binding fragment thereof as described herein specifically binds to an alpha subunit of a specific subtype of an L-type voltage gated channel. The subtypes of the L-type voltage gated calcium channels include Cav1.4, Cav1.3, Cav1.2, and Cav1.1. In particular embodiments, the antibody or antigen-binding fragment thereof specifically binds to an extracellular region of the alpha 1 subunit of Cav1.4, Cav1.3, Cav1.2, or Cav1.1. In some embodiments, the antibody or antigen-binding fragment thereof specifically binds to an amino acid sequence located on the extracellular pore loop between S5 and S6 of domain I of the Cav1.4, Cav 1.3, Cav1.2, or Cav1.1 alpha 1 subunit. In particular embodiments, the amino acid sequence is GPGRPGDAPHTG [SEQ ID NO: 1] of Cav1.4, or is at least 90% identical to GPGRPGDAPHTG [SEQ ID NO: 1]. In some embodiments, the amino acid sequence is LTKETEGGNHSSGKSG [SEQ ID NO 2] of Cav1.3, or is at least 90% identical to LTKETEGGNHSSGKSG [SEQ ID NO 2]. In some embodiments, the amino acid sequence is ATKADGANALGGKGA [SEQ ID NO: 3] of Cav1.2, or is at least 90% identical to ATKADGANALGGKGA [SEQ ID NO: 3] of Cav1.2. In particular embodiments, the amino acid sequence is PMQIELRHREWV$_H$ [SEQ ID NO 4] of Cav1.1, or is at least 90% identical to PMQIELRHREWV$_H$ [SEQ ID NO 4].

Each L-type voltage-gated calcium channel subtype has several splice variants. Alternative splicing is a regulated process during gene expression that results in a single gene coding for multiple isoforms of the protein. In this process, particular exons of a gene may be included within or excluded from the final, processed messenger RNA (mRNA) produced from that gene. Consequently the proteins translated from alternatively spliced mRNAs will contain differences in their amino acid sequence. Alternative splicing occurs as a normal phenomenon in eukaryotes, and has been described in the genes encoding L-type voltage-gated subunits. As used herein, the term "L-type voltage-gated calcium channel," unless otherwise specified, includes Cav1.1, Cav1.2, Cav1.3, and Cav1.4, and all isoforms of the alpha 1 subunit that result from alternative splicing of mRNA encoding Cav1.1, Cav1.2, Cav1.3, and Cav1.4.

L-type voltage-gated calcium channel subtypes are expressed in different cell types and tissue types throughout the body, and can be expressed as different variants, including variants that result from alternate splicing of message RNA, or different post translational modifications, such as glycosylation or phosphorylation. Different variants of the subtype can be expressed in different tissue or cell types, or alternatively, different variants of the subtype can be expressed in the same tissue or cell type, including in the same cell. In particular embodiments, the antibody or antigen binding fragment thereof specifically binds to all variants of the subtype. In some embodiments, the antibody or antigen binding fragment thereof specifically binds to a subset of the variants of the subtype. In particular embodiments, the antibody or binding fragment thereof specifically binds to the subtype expressed in any cell or tissue. In some embodiments, the antibody or binding fragment thereof specifically binds to the subtype in a subset of cells or tissues of which the subtype is expressed.

In a particular embodiment, the antibody or antigen-binding fragment thereof described herein specifically binds to any one or more of Cav1.4, Cav1.3, Cav1.2, and Cav1.1. In some embodiments, the antibody or antigen-binding fragment thereof specifically binds to any three of Cav1.4, Cav1.3, Cav1.2, and Cav1.1. Such an antibody or antigen-binding fragment thereof may specifically bind to any of Cav1.4, Cav1.3, and Cav1.2; Cav1.4, Cav1.3, and Cav1.1; Cav1.4, Cav1.2, and Cav1.1; or Cav1.3, Cav1.2, and Cav1.1. In some embodiments, the antibody or antigen-binding fragment thereof specifically binds to any two of Cav1.4, Cav1.3, Cav1.2, and Cav1.1. Such an antibody or antigen-binding fragment thereof specifically binds to any of Cav1.4 and Cav1.3; Cav1.4 and Cav1.2; Cav1.4 and Cav1.1; Cav1.3 and Cav1.2; Cav1.3 and Cav1.1; or Cav1.2 and Cav1.1. In some embodiments, the antibody or binding fragment thereof specifically binds to only one subtype of an L-type voltage-gated calcium channel. Such an antibody will only bind to Cav1.4, Cav1.3, Cav1.2, or Cav1.1, relative to the other Cav1 subtypes.

In certain embodiments, an antibody or antigen-binding fragment thereof described herein specifically binds to cells expressing an L-type voltage-gated calcium channel. In some embodiments, the antibody or antigen-binding fragment will bind to any cell expressing the L-type voltage-gated calcium channel. In some embodiments, the antibody or antigen-binding fragment will bind to a subset of cells expressing the L-type voltage-gated calcium channel. In particular embodiments, the antibody or antigen-binding fragment will specifically bind to a subset of cells expressing the L-type voltage-gated calcium channel, but not bind to another subset of cells expressing the L-type voltage-gated calcium channel. In some embodiments, the antibody or antigen-binding fragment will specifically bind any cells expressing one or more of Cav1.4, Cav1.3, Cav1.2, and Cav1.1. In certain embodiments, an antibody or antigen-binding fragment described herein will specifically bind to a subset of cells expressing one or more of Cav1.4, Cav1.3, Cav1.2, and Cav1.1. In particular embodiments, the antibody or antigen-binding fragment will specifically bind to some cell types expressing a particular subtype of an L-type voltage-gated calcium channel, but not to other cell types expressing the same subtype of the L-type voltage-gated calcium channel. In particular embodiments, the antibody or antigen-binding fragment thereof specifically binds to some cell types that express a variant of the channel subtype, but not to other cell types that express the same variant of the channel subtype. In certain embodiments, the antibody or antigen-binding fragments thereof specifically binds to cells expressing one or more variants of the channel subtype, but not to cells expressing different variants of the channel subtype.

In some embodiments, the antibodies are defined by the light chain variable region sequences and/or heavy chain variable regions described herein, and/or the complementary determining region (CDR) sequences or antigen-binding regions (ABRs) contained therein, including variants and combinations of these sequences that specifically bind to amino acid sequence on an extracellular pore loop between S5 and S6 of domain I of an alpha one subunit of an L-type voltage-gated calcium channel. Also included are antibodies that competitively inhibit the binding of such antibodies to an extracellular pore loop between S5 and S6 of domain I of an alpha one subunit of an L-type voltage-gated calcium channel.

The term "antigen-binding fragment" as used herein refers to a polypeptide fragment that contains at least one CDR of an immunoglobulin heavy and/or light chains that specifically bind to the antigen of interest. In this regard, an antigen-binding fragment of the herein described antibodies may comprise 1, 2, 3, 4, 5, or all 6 CDRs of a $V_H$ and $V_L$ sequence from antibodies that specifically bind to a therapeutic or diagnostic target such as an extracellular pore loop between S5 and S6 of domain I of an alpha one subunit of an L-type voltage-gated calcium channel, including fragments thereof.

The term "antigen" refers to a molecule or a portion of a molecule capable of being bound by a selective antibody, or an antigen-binding fragment thereof, and additionally capable of being used in an animal to produce antibodies capable of binding to an epitope of that antigen. An antigen may have one or more epitopes.

The term "epitope" includes any determinant, preferably a polypeptide determinant, capable of specific binding to an immunoglobulin or T-cell receptor. An epitope is a region of an antigen that is bound by an antibody. In certain embodiments, epitope determinants include chemically active surface groupings of molecules such as amino acids, sugar side chains, phosphoryl or sulfonyl, and may in certain embodiments have specific three-dimensional structural characteristics, and/or specific charge characteristics. Epitopes can be contiguous or non-contiguous in relation to the primary structure of the antigen.

An antibody or antigen-binding fragment thereof, is said to exhibit "specific binding" or "preferential binding" if it reacts or associates more frequently, more rapidly, with greater duration and/or with greater affinity with a particular cell or substance than it does with alternative cells or substances. An antibody "specifically binds" or "preferentially binds" to a target if it binds with greater affinity, avidity, more readily, and/or with greater duration than it binds to other substances. For example, an antibody that specifically or preferentially binds to a specific epitope is an antibody that binds that specific epitope with greater affinity, avidity, more readily, and/or with greater duration than it binds to other epitopes. It is also understood by reading this definition that, for example, an antibody (or moiety or epitope) that specifically or preferentially binds to a first target may or may not specifically or preferentially bind to a second target. As such, "specific binding" or "preferential binding" does not necessarily require (although it can include) exclusive binding. Generally, but not necessarily, reference to binding means preferential binding.

Immunological binding generally refers to the non-covalent interactions of the type which occur between an immunoglobulin molecule and an antigen for which the immunoglobulin is specific, for example, by way of illustration and not limitation, as a result of electrostatic, ionic, hydrophilic and/or hydrophobic attractions or repulsion, steric forces, hydrogen bonding, van der Waals forces, and other interactions. The strength, or affinity of immunological binding interactions can be expressed in terms of the dissociation constant ($K_d$) of the interaction, wherein a smaller $K_d$ represents a greater affinity. Immunological binding properties of selected polypeptides can be quantified using methods well known in the art. One such method entails measuring the rates of antigen-binding site/antigen complex formation and dissociation, wherein those rates depend on the concentrations of the complex partners, the affinity of the interaction, and on geometric parameters that equally influence the rate in both directions. Thus, both the "on rate constant" ($k_{on}$) and the "off rate constant" ($k_{off}$) can be determined by calculation of the concentrations and the actual rates of association and dissociation. The ratio of $k_{off}/k_{on}$ enables cancellation of all parameters not related to affinity, and is thus equal to the dissociation constant $K_d$.

Immunological binding properties of antibodies, and antigen-binding fragments thereof, can be quantified using methods well known in the art (see Davies et al., Annual Rev. Biochem. 59:439-473, 1990). In some embodiments, an antibody is said to specifically bind an antigen or epitope thereof when the equilibrium dissociation constant is about $\leq 10^7$ or $10^8$M. In some embodiments, the equilibrium dissociation constant of a protein may be about $\leq 10^{-9}$ M or $\leq 10^{-10}$ M. In certain illustrative embodiments, a protein has an affinity ($K_d$) for an antigen or target described herein (to which it specifically binds) of about, at least about, or no more than about 0.01, 0.05, 0.1, 0.2, 0.3, 0.4, 0.5, 0.6, 0.7, 0.8, 0.9, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 40, or 50 nM.

As used herein, the terms "L-type Voltage-Gated Calcium Channel" and "CaV1" channels are used interchangeably, and are meant to include Cav1.1, Cav1.2, Cav1.3, and Cav1.4 unless otherwise specified. "L-type Voltage-Gated Calcium Channel" and "CaV1" channels also comprise Cav1.1, Cav1.2, Cav1.3, and Cav1.4 channels that may undergo variations in post-expression modifications, such as glycosylations, acetylations, phosphorylations and the like, and include the entire Cav1.1, Cav1.2, Cav1.3, and Cav1.4 proteins, as well as subsequences, fragments, variants (including but not limited to variants resulting from alterative splicing), or derivatives thereof.

The primary amino acid sequence of human and mouse L-type voltage gated calcium channel alpha 1 subunits are shown in Table 1 below. Of note, mRNAs encoding alpha 1 subunits of L-type voltage-gated calcium channels have splice variants that can result in different isoforms of the polypeptide. Therefore, the amino acid sequences listed in Table 1 are exemplary.

TABLE 1

L-Type Voltage Gated Calcium Channels (CaV1)Alpha Subunits

| Name | Gene Symbol | Amino Acid Sequence | SEQ ID NO: |
|---|---|---|---|
| Human CaV1.4 | CACNA1F | mseseggkdttpepspangagpgpewglcpgppavegessgasglgtpk rrnqhskhktvavasaqrspralfcltlanplrrscisivewkpfdili lltifancvalgvyipfpeddsntanhnleqveyvflviftvetvlkiv ayglvlhpsayirngwnlldfiivvvglfsvlleqgpgrpgdaphtggk pggfdvkalrafrvlrplrlvsgvpslhivlnsimkalvpllhiallvl fviiiyaiiglelfigrmhktcyflgsdmeaeedpspcassgsgractl nqtecrgrwpgpnggitnfdnfffamitvfqcvtmegwtdvlywmqdam gyelpwvyfvslvifgsffvlnlvlgvlsgefskerekakargdfqkqr ekqqmeedlrgyldwitqaeeldmedpsaddnlgsmaeegraghrpqla eltnrrrgrlrwfshstrsthstsshaslpasdtgsmtetqgdedeeeg alasctrclnkimktrvcrrlrranrvlrarerravksnacywavlllv fintitiasehhgqpvwltqiqeyankvllelftvemllklyglgpsay vssffnrfdcfvvcggilettlvevgamqplgisvlrcvrllrifkvtr hwaslsnivaslllnsmksiasllllllfifiiifsllgmqlfggkfnfdq thtkrstfdtfpqalltvfqiltgedwnvvmydgimayggpffpgmlvc iyfiilficgnyillnvflaiavdnlasgdagtakdkggeksnekdlpq enegivpgvekeeeegarregadmeeeeeeeeeeeeeeegaggvell qevvpkekvvpipegsaffcisqtnplrkgchtlihhhvftnlilvfii issvslaaedpirahsfrnhilgyfdyaftsiftveillkmtvfgafih rgsfcrswfnmldllvvsvslisfgihssaisvvkilrvlrvlrplrai nrakglkhvvqcvfvairtignimivttllqfmfacigvqlfkgkfytc tdeakhtpqeckgsfivypdgdvsrplvrerlwvnsdfnfdnvlsamma iftvstfegwpallykaidayaedhgpiynyrveisvffivyiiiiaff mmnifvgfviitfraqgeqeyqneeldknqrqcveyalkaqplrryipk nphqyrvwatvnsaafeyimfllillntvalamqhyeqtapfnyamdil nmvftglftiemvlkiiafkpkhyftdawntfdalivvgsivdiavtev nngghlgessedssrisitffrifrvmrlvkllskgegirtllwtfiks fqalpyvalliamiffiyavigmqmfgkvalqdgtqinrnnnfqtfpqa vlllfrcatgeawqeimlaslpgnrcdpesdfgpgeeftegsnfaiayf isffmlcafliinlfvavimdnfdyltrdwsilgphhldefkriwseyd pgakgrikhldvvallrriqpplgfgklcphrvackrlvamnmplnsdg tvtfnatlfalvrtslkiktegnleqanqelrivikkiwkrmkqkllde vipppdeeevtvgkfyatfliqdyfrkfrrrkekgllgndaapstssal qaglrslqdlgpemrqaltcdteeeeeegqegveeedekdletnkatmv sqpsarrgsgisvslpvgdrlpdslsfgpsdddrgtptssqpsvpqags nthrrgsgaliftipeegnsqpkgtkgqnkqdedeevpdrlsyldeqag tppcsvllpphraqrymdghlvprrrllpptpagrkpsftiqclqrqgs | 5 |

TABLE 1-continued

L-Type Voltage Gated Calcium Channels (CaV1) Alpha Subunits

| Name | Gene Symbol | Amino Acid Sequence | SEQ ID NO: |
|---|---|---|---|
| | | cedlpipgtyhrgrnsgpnraqgswatppqrgrllyaplllveegaage gylgrssgplrtftclhvpgthsdpshgkrgsadslveavliseglglf ardprfvalakqeiadacrltldemdnaasdllaqgtsslysdeesils rfdeedlgdemacvhal | |
| Human CaV1.3 | CACNL1A2 | mmmmmmmkkmqhqrqqqadhaneanyargtrlplsgegptsqpnsskqt vlswqaaidaarqakaaqtmstsapppvgslsqrkrqqyakskkqgnss nsrparalfcisinnpirracistvewkpfdifilialfanevalaiyi pfpeddsnstnhnlekveyafiiiftvetflkiiaygllhpnayvrng wnlldfvivivglfsvileqitketeggnhssgksggfdvkalrafrvl rplrlvsgvpslqvvlnsiikamvpllhiallvlfviiiyaiiglelfi gkmhktcffadsdivaeedpapcafsgngrqctangtecrsgwvgpngg itnfdnfafamltvfqcitmegwtdvlywmndamgfelpwvyfvslvif gsffvlnlvlgvlsgefskerekakargdfqklrekqqleedlkgyldw itqaedidpeneeeggeegkrntsmptsetesvntenvsgegenrgccg slcqaiskskslsrrwrrwnrfnrrrcraavksvtfywlvivlvfintit issehynqpdwltqiqdiankvllalftcemlvkmyslglqayfvsifn rfdcfvvcggitetilveleimsplgisvfrcvrllrifkvtrhwtsls nlvasllnsmksiaslllllfifiiifsllgmqlfggkfnfdetqtkrs tfdnfpqalltvfqiltgedwnavmydgimayggpsssgmivciyfiil ficgnyillnvflaiavdnladaeslntaqkeeaeekerkkiarkesle nkknnkpevnqiansdnkvtiddyreededkdpyppcdvpvgeeeeeee edepevpagprprriselnmkekiapipegsaffilsktnpirvgchkl inhhiftnlilvfimlssaalaaedpirshsfrntilgyfdyaftaift veillkmttfgaflhkgafernyfnlldmlvvgvslvsfgiqssaisvv kilrvlrvlrplrainrakglkhvvqcvfvairtignimivttllqfmf acigvqlfkgkfyretdeaksnpeecrglfilykdgdvdspvvreriwq nsdfnfdnvisammalftvstfegwpallykaidsngenigpiynhrve isiffiiyiiiavaffmmnifvgfvivtfqeqgekeykneeldknqrqcv eyalkarplrryipknpyqykfwyvvnsspfeymmfvlimlntlclamq hyeqskmfndamdilnmvftgvftvemvlkviafkpkgyfsdawntfds livigsiidvalseadptesenvpvptatpgnseesnrisitffrifrv mrlvkllsrgegirtllwtfiksfqalpyvalliamiffiyavigmqmf gkvamrdnnqinrnnnfqtfpqavlllfrcatgeawqeimlaclpgklc dpesdynpgeeytegsnfaivyfisfymleafliinlfvavimdnfdyl trdwsilgphhldefkriwseydpeakgrikhldvvtllrriqpplgfg klcphrvackrlvamnmplnsdgtvmfnatlfalvrtalkiktegnleq aneelravikkiwkktsmklldqvvppagddevtvgkfyatfliqdyfr kfkkrkeqglvgkypaknttialqaglrtlhdigpeirraiscdlqdde peetkreeeddvfkrngallgnhvnhvnsdrrdslqqtntthrplhvqr psippasdtekplfppagnsvchnhhnhnsigkqvptstnanlnnanms kaahgkrpsignlehvsenghhsshkhdrepqrrssvkrtryyetyirs dsgdeqlpticredpeihgyfrdphclgeqeyfsseecyeddssptwsr qnygyysrypgrnidserprgyhhpqgfledddspvcydsrrsprrrll pptpashrrssfnfeclrrqssqeevpsspifphrtalplhlmqqqima vagidsskaqkyspshstrswatppatppyrdwtpcytpliqveqseal dqvngslpslhrsswytdepdisyrtftpasltvpssfrnknsdkqrsa dslveavliseglgryardpkfvsatkheiadacdltidemesaastil ngnvrprangdvgplshrqdyelqdfgpgysdeepdpgrdeedlademi cittl | 6 |
| Human CaV1.2 | CACNL1A1 | mvnentrmyipeenhqgsnygsprpahanmmnanaaaglapehiptpgaa lswqaaidaarqaklmgsagnatistvsstqrkrqqygkpkkqgsttat rpprallcltlknpirracisivewkpfeiiilltifancvalaiypf peddsnatnsnlrerveylfliiftveaflkviaygllfhpnaylrngwn lldfiivvvglfsaileqatkadganalggkgagfdvkalrafrvlrpl rlvsgvpslqvvlnsiikamvpllhiallvlfviiiyaiiglelfmgkm hktcynqegiadvpaeddpspcaletghgrqcqngtvckpgwdgpkhgi tnfdnfafamitvfqcitmegwtdvlywvndavgrdwpwiyfvtliiig sffvlnlvlgvlsgefskerekakargdfqklrekqqleedlkgyldwi tqaedidpenedegmdeekprnmsmptsetesvntenvaggdiegencg arlahrisskfsrywrrwnrfcrrkcraavksnvfywivifivfinti tiasehynqpnwltevqdtankallalftaemllkmyslglqayfvslf nrfdcfvveggiletilvetkimsplgisvlrcvrllrifkitrywnsl snlvasllnsvrsiasllllflfiiifsllgmqlfggkfnfdemqtrr stfdnfpqslltvfqiltgedwnsvmydgimayggpsfpgmlvciyfii ificgnyillnvflaiavdnladaesltsaqkeeeeekerkklartasp ekkqelvekpavgeskeekielksitadgesppatkinmddlqpnened kspypnpettgeedeeepempvgprprplselhlkekavpmpeasaffi fssnnrfrlqchrivndtiftnlilffillssislaaaedpvqhtsfrnh ilfyfdivfttiftieialkilgnadyvftsiftleiilkmtaygaflh kgsfcrnyfnildllvvsvslisfgiqssainvvkilrvlrvlrplrai nrakglkhvvqcvfvairtigniviivttllqfmfacigvqlfkgklytc sdsskqteaeckgnyitykdgevdhpiiqprswenskfdfdnvlaamma iftvstfegwpellyrsidshtedkgpiynyrveisiffiiyiiiiaff | 7 |

TABLE 1-continued

L-Type Voltage Gated Calcium Channels (CaV1)Alpha Subunits

| Name | Gene Symbol | Amino Acid Sequence | SEQ ID NO: |
|---|---|---|---|
| | | mmnifvgfvivtfqeqgeqeykncefdknqrqcveyalkarplrryipk nqhqykvwyvvnstyfeylmfvlillnticlamqhygqselfkiamnil nmlftglftvemilkliafkpkgyfsdpwnvfdflivigsiidvilset nhyfcdawntfdalivvgsivdiaitevnpaehtqcspsmnaeensris itffrlfrvmrlvkllsrgegirtllwtfiksfqalpyvallivmlffi yavigmqvfgkialndtteinrnnnfqtfpqavlllfrcatgeawqdim lacmpgkkcapesepsnstegetpcgssfavfyfisfymleafliinlf vavimdnfdyltrdwsilgphhldefkriwaeydpeakgrikhldvvtl irriqpplgfgklephrvackrlvsmnmplnsdgtvmfnatlfalvrta lriktegnleqaneelraiikkiwkrtsmklldqvvppagddevtvgkf yatfliqeyfrkfkkrkeqglvgkpsqrnalslqaglrtlhdigpeirr aisgdltaeeeldkamkeavsaaseddifrragglfgnhvsyyqsdgrs afpqtfttqrplhinkagssqgdtespsheklvdstftpssysstgsna ninnanntalgrlprpagypstvstveghgpplspairvqevawklssn rerhvpmcedlelrrdsgsagtqahcllllrranpsrchsresqaamagq eetsqdetyevkmnhdteacsepsllstemlsyqddenrqltlpeedkr dirqspkrgflrsaslgrrasfhlecklrqkdrggdisqktvlplhlvh hqalavaglspllqrshspasfprpfatppatpgsrgwppqpvptlrle gvessekinssfpsihcgswaettpggggssaarrvrpvslmvpsqaga pgrqfhgsasslveavliseglgqfaqdpkfievttqeladacdmtiee mesaadnilsggapqspngallpfvncrdagqdraggeedagcvrargr pseeelqdsrvyvssl | |
| Human CaV1.1 | CACNL1A3 | mepsspqdeglrkkqpkkpvpeilprppralfcltlenplrkacisive wkpfetiilltifancvalavylpmpeddnnslnlglekleyfflivfs ieaamkiiaygfifhqdaylrsgwnvldftivfigvftvileqvnviqs htapmsskgagldvkalrafrvlrplrlvsgvpslqvvlnsifkamlpl fhiallvlfmviiyaiiglelfkgkmhktcyfigtdivatveneepspc artgsgrrctingsecrggwpgpnhgithfdnfgfsmltvyqcitmegw tdvlywvndaignewpwiyfvtlillgsffilnlvlgvlsgeftkerek aksrgtfqklrekqqldedlrgymswitqgevmdvedfregklsldegg sdteslyeiaglnkiiqfirhwrqwnrifrwkchdivkskvfywivili valntlsiasehhnqplwltrlqdianrvllslftttemlmkmyglglrq yfmsifnrfdcfvvcsgileillvesgamtplgisvlrcirllrifkit kywtslsnlvaslInsirsiasllllllfIfivifallgmqlfggrydfe dtevrrsnfdnfpqalisvfqvltgedwtsmmyngimayggpsypgmlv ciyfiillfvcgnyillnvflaiavdnlaeaesltsaqkakaeekkrrkm skglpdkseeekstmakkleqkpkgegiptttaklkidefesnvnevkdp ypsadfpgddeedepeiplsprprplaelqlkekavpipeassffifsp tnkirvlchrivnatwftnfillfillssaalaaedpiradsmrnqilk hfdigftsvftveivlkmttygaflhkgsfcrnyfnmlldllvvavslis mglessaisvvkilrvlrvlrplrainrakglkhvvqcmfvaistigni vlvttllqfmfacigvqlfkgkffrctdlskmteeecrgyyyvykdgdp mqielrhrewvhsdfhfdnvlsammslftvstfegwpqllykaidsnae dvgpiynnrvemaiffiiyiiliaffmmnifvgfvivtfqeqgeteykn celdknqrqcvqyalkarplrcyipknpyqyqvwyivtssyfeylmfal imlnticlgmqhynqseqmnhisdilnvaftiiftlemilklmafkarg yfgdpwnvfdflivigsiidvilseidtflassgglyelgggcgnvdpd esarissaffrifrvmrliklIsraegvrtllwtfiksfqalpyvalli vmlffiyavigmqmfgkialvdgtqinrnnnfqtfpqavlllfrcatge awqeillacsygklcdpesdyapgeeytcgtnfayyyfisfymlcaflv inlfvavimdnfdyltrdwsilgphhldefkaiwaeydpeakgrikhld vvtllrriqpplgfgkfcphrvackrlvgmnmplnsdgtvtfnatlfal vrtalkiktegnfeqaneelraiikkiwkrtsmklldqvippigddevt vgkfyatfliqehfrkfmkrqeeyygyrpkkdivqiqaglrtieeeaap eicrtvsgdlaaeeeleramveaameegifrrtgglfgqvdnflertns ippvmanqrplqfaeiemeemespvfledfpqdprtnplarantnnana nvaygnsnhsnshvfssvhyerefpeetetpatrgralgqpcrvlgphs kpcvemlkglltqramprgqappapcqcprvessmpedrksstpgsihe etphsrstrentsrcsapatalliqkalvrgglgtlaadanfimatgqa ladacqmepeeveimatellkgreapegmasslgclnlgssslgsldqhq gsqetlipprl | 8 |
| Mouse CaV1.4 | CACNA1F | msesevgkdttpepspangtgpgpewglcpgpptvgtdtsgasglgtpr rrtqhnkhktvavasaqrspralfcltltnpirrscisivewkpfdili lltifancvalgvyipfpeddsntanhnleqveyvfiviftvetvikiv ayglvlhpsayirngwnlldfiivvvglfsvlleqgpgrpgdaphtggk pggfdvkalrafrvlrplrlvsgvpslhivlnsimkalvpllhiallvl fviiiyaiiglelfigrmhktcyflgsdmeaeedpspcassgsgrsctl nhtecrgrwpgpnggitnfdnffffamitvfqcitmegwtdvlywmqdam gyelpwvyfvslvifgsffvlnlvlgvlsgefskerekakargdfqklr ekqqmeedlrgyldwitqaeeldlhdpsvdgnlaslaeegraghrpqls eltnrrrgrlrwfshstrsthstsshaslpasdtgsmtdtpgdedeeeg tmasctrclnkimktricrhfrranrglrarcrravksnacywavlllv fintitiasehhgqplwitqtqeyankvllelftvemllklyglgpsvy | 9 |

TABLE 1-continued

L-Type Voltage Gated Calcium Channels (CaV1) Alpha Subunits

| Name | Gene Symbol | Amino Acid Sequence | SEQ ID NO: |
|---|---|---|---|
| | | vasffnrfdcfvvcggilettlvevgamqplgisvlrcvrllrifkvtr hwaslsnivasllnsmksiaslllllfifiiifsllgmqlfggkfnfdq thtkrstfdtfpqalltvfqiltgedwnvvmydgimayggpffpgmivc vyfiilficgnyillnvflaiavdnlasgdagtakdkgrekssegnppk enkvlvpggenedakgarsegaapgmeeeeeeeeeeeeeeeeengaghv ellqevvpkekvvpipegsaffclsqtnplrkachtlihhhiftslilv fiilssvslaaedpirahsfrnhilgyfdyaftsiftveillkmtvfga fihrgsfcrswfnlldllvvsvslisfgihssaisvvkilrvlrvlrpl rainrakglkhvvqcvfvairtignimivttllqfmfacigvqlfkgkf ysctdeakhtikeckgsfliypdgdvsrplvrerlwvnsdfnfdnvlsa mmalftvstfegwpallykaidanaedegpiynyhveisvffivyiiii affmmnifvgfviitfraqgeqeyqnceldknqrqcveyalkaqplrry ipknphqyrvwatvnsaafeylmflllllntvalamqhyeqtapfnyam dilnmvftglftiemvlkiiafkpkhyfadawntfdalivvgsvvdiav tevnngghlgessedssrisitffrifrvmrlvkllskgegirtllwtf iksfqalpyvalliamiffiyavigmqmfgkvalqdgtqinrnnnfqtf pqavllllfrcatgeawqeimlaslpgnrcdpesdfgpgeeftcgssfai vyfisffmicafliinlfvavimdnfdyltrdwsilgphhldefkriws eydpgakgrikhldvvallrriqpplgfgklcphrvackrlvamnvpln sdgtvtfnatlfalvrtslkiktegnldqanqelrmvikkiwkrikqkl ideviппpdeeevtvgkfyatfliqdyfrkfrrrkekgllgreaptsts salqaglrslqdlgpeirqaltydteeeeeeeeavgqeaeeeeaennpe pykdsidsqpqsrwnsrisvslpvkeklpdslstgpsdddglapnsrqp sviqagsqphrrssgvfmftipeegsiqlkgtqgqdnqneeqevpdwtp dldeqagtpsnpvllpphwsqqhvnghhvprrrllpptpagrkpsftiq clqrqgscedlpipgtyhrgrtsgpsraqgswaappqkgrllyaplllv eestvgegylgklggplrtftclqvpgahpnpshrkrgsadslveavli seglglfaqdprfvalakqeiadachltldemdsaasdllaqrttslys deesilsrfdeedlgdemacvhal | |
| Mouse CaV1.3 | CACNL1A2 | mnlptfssdliliksvlsqetdarykgrvvsavestedfsqafaeanya rgtrlpisgegptsqpnsskqtvlswqaaidaarqakaaqtmstsappp vgslsqrkrqqyakskkqgnssnsrparalfclslnnpirracisivew kpfdifillaifancvalaiyipfpeddsnstnhnlekveyafliiftv etfikiiaygllhpnayvrngwnlldfvivivglfsvileqltketeg gnhssgksggfdvkalrafrvlrplrlvsgvpslqvvlnsiikamvpll hiallvlfviiiyaiiglelfigkmhktcffadsdivaeedpapcafsg ngrqctangtecrsgwvgpnggitnfdnfafamitvfqcitmegwtdvl ywvndaigwewpwvyfvsliilgsffvlnlvlgvlsgefskerekakar gdfqklrekqqleedlkgyldwitqaedidpeneeeggeegkrntsmpt setesvntenvsgegetqgccgtlcqaiskskslsrrwrrwnrfnrrrcr aavksvtfywlvivlvflntltissehynqpdwltqiqdiankvllalf tcemlvkmyslglqayfvslfnrfdcfvvcggitetilvelelmsplgv svfrcvrllrifkvtrhwtslsnlvaslnsmksiaslllllflfiiif sllgmqlfggkfnfdetqtkrstfdnfpqalltvfqiltgedwnavmyd gimayggpsssgmivciyfiilficgnyillnvflaiavdnlalaesln taqkeeaeeekerkkiarkeslenkknnkpevnqiansdnkvtiddyqed aedkdpyppcdvpvgeeeeeeeedepevpagprprriselnmkekiapi pegsaffilsktnpirvgchklinhhiftnlilvfimlssaalaaedpi rshsfrntilgyfdyaftaiftveillkmttfgaflhkgafernyfnil dmlvvgvslvsfgiqssaisvvkilrvlrvlrplrainrakglkhvvqc vfvairtignimivttllqfmfacigvqlfkgkfyrctdeaksnpeecr glfilykdgdvdspvvreriwqnsdfnfdnvlsammalftvstfegwpa llykaidsngenvgpvynyrveisiffiiyiiivaffmmnifvgfvivt fqeqgekeyknceldknqrqcveyalkarplrryipknpyqykfwyvvn sspfeymmfvlimlntlclamqhyeqskmfndamdilnmvftgvftvem vlkviafkpkgyfsdawntfdslivigsiidvalseadnseesnrisit ffrlfrvmrlvkllsrgegirtllwtfiksfqalpyvalliamiffiya vigmqmfgkvamrdnnqinrnnnfqtfpqavllllfrcatgeawqeimla elpgklcdpdsdynpgeeytcgsnfaivyfisfymlcafliinlfvavi mdnfdyltrdwsilgphhldefkriwseydpeakgrikhldvvtllrri qpplgfgklcphrvackrlvamnmplnsdgtvmfnatlfalvrtalkik tegnleqaneelravikkiwkktsmklldqvvppagddevtvgkfyatf liqdyfrkfkkrkeqglvgkypaknttialqaglrtlhdigpeirrais cdlqddepedskpeeedvfkrngallgnhvnhvnsdrrdslqqtntthr plhvqrpsmppasdtekplfppagnsgchnhhnhnsigkqaptstnanl nnanmskaahgkppsignlehvsenghysckhdrelqrssikrtryye tyirsesgdeqfpticredpeihgyfrdprclgeqeyfsseecceddss ptwsrqnynyynrypgssmdferprgyhhpqgfledddsptgydsrrsp rrrllpptppshrrssfnfeclrrqssqddvlpspalphraalplhlmq qqimavagldsskaqkyspshstrswatppatppyrdwspcytpliqvd rsesmdqvngslpslhrsswytdepdisyrtftpasltvpssfrknsd kqrsadslveavliseglgryardpkfvsatkheiadacdltidemesa astlingsvcprangdmgpishrqdyelqdfgpgysdeepdpgreeedl ademicittl | 10 |

TABLE 1-continued

L-Type Voltage Gated Calcium Channels (CaV1) Alpha Subunits

| Name | Gene Symbol | Amino Acid Sequence | SEQ ID NO: |
|---|---|---|---|
| Mouse CaV1.2 | CACNL1A1 | mvnentrmyvpeenhqgsnygsprpahanmnanaaaglapehiptpgaa lswqaaidaarqaklmgsagnatistvsstqrkrqqygkpkkqggttat rpprallcltlknpirracisivewkpfeiiilltifancvalaiyipf peddsnatnsnlerveylfliiftveaflkviaygllfhpnaylrngwn lldfiivvvglfsaileqatkadganalggkgagfdvkalrafrvlrpl rlvsgvpslqvvlnsiikamvpllhiallvlfviiiyaiiglelfmgkm hktcynqegiidvpaeedpspcaletghgrqcqngtvckpgwdgpkhgi tnfdnfafamitvfqcitmegwtdvlywmqdamgyelpwvyfvslvifg sffvlnlvlgvlsgefskerekakargdfqklrekqqleedlkgyldwi tqaedidpenedegmdedkprnmsmptsetesvntenvaggdiegencg arlahriskskfsrywrrwnrfcrrkcraavksnvfywivifivfinti tiasehynqphwltevqdtankallalftaemllkmyslglqayfvslf nrfdcfivcggiletilvetkimsplgisvlrcvrllrifkitrywnsl snlvaslllnsvrsiasllllflfiiifsllgmqlfggkfnfdemqtrr stfdnfpqslltvfqiltgedwnsvmydgimayggpsfpgmlvciyfii ificgnyillnvflaiavdnladaesltsaqkeeeeekerkklartasp ekkqevmekpaveeskeekielksitadgesppttkinmddlqpsened ksphsnpdtageedeeepempvgprprplselhlkekavpmpeasaffi fspnnrfrlqchrivndtiftnlilffillssislaaedpvqhtsfrnh ilgnadyvftsiftleiilkmtaygafihkgsfernyfnildllvvsvs lisfgiqssainvvkilrvlrvlrplrainrakglkhvvqcvfvairti gnivivttllqfmfacigvqlfkgklytcsdsskqteaeckgnyitykd gevdhpiiqprswenskfdfdnvlaammalftvstfegwpellyrsids htedkgpiynyrveisiffiiyiiiaffmmnifvgfvivtfqeqgeqe yknceldknqrqcveyalkarplrryipknqhqykvwyvvnstyfeylm fvlillnticlamqhygqsclfkiamnilnmlftgltftvemilkliafk pkgyfsdpwnvfdflivigsiidvilsetnpaehtqcspsmsaeensri sitffrlfrvmrlvkllsrgegirtlllwtfiksfqalpyvallivmlff iyavigmqvfgkialndtteinrnnnfqtfpqavlllfrcatgeawqdi mlacmpgkkcapesepsnstegetpegssfavfyfisfymicafliinl fvavimdnfdyltrdwsilgphhldefkriwaeydpeakgrikhldvvt llrriqpplgfgklcphrvackrlvsmnmplnsdgtvmfnatifalvrt alriktegnleqaneelraiikkiwkrtsmklldqvvppagddevtvgk fyatfliqeyfrkfkkrkeqglvgkpsqrnalslqaglrtlhdigpeir raisgdltaeeeldkamkeavsaaseddifrragglfgnhvtyyqsdsr gnfpqtfatqrplhinktgnnqadtespsheklvdstftpssysstgsn aninnanntalgrfphpagysstvstveghgpplspavrvqeaawklss krchsresqgatvnqeifpdetrsvrmseeaeycsepsllstdmfsyqe dehrqltcpeedkreiqpspkrsflrsaslgrrasfhleclkrqkdqgg disqktalplhlvhhqalavaglspllqrshspttfprpcptppvtpgs rgrplrpiptlrlegaesseklnssfpsihesswseettaesgsssmar rarpvsltvpsqagapgrqfhgsassiveavlisegigqfaqdpkfiev ttqeladacdmtieemenaadnilsggaqqspngtllpfvnerdpgqdr avapedescayalgrgrseealadsrsyvsnl | 11 |
| Mouse CaV1.1 | CACNL1A3 | meppspqdeglrkkqpkkpvpeilprppralfcltlqnplrkacisive wkpfetiilltifancvalavylpmpeddnntlnlglekleyfflivfs ieaamkiiaygfifhqdaylrsgwnvldfiivfigvftvileqvniqt ntapmsskgagldvkalrafrvlrplrlvsgvpsiqvvlnsifkamlpl fhiallvlfmviiyaiiglelfkgkmhkteyfigtdivatvenekpspe artgsgrpetingseerggwpgpnhgithfdnfgfsmltvyqcismegw tdvlywvndaignewpwiyfvtlillgsffilnlvlgvlsgeftkerek aksrgtfqklrekqqleedlrgymswitqgevmdvddlregklsldegg sdteslyeieglnkiiqfirhwrqwnrvfrwkchdivkskvfywivili valntlsiasehhnqplwlthlqdvanrvlltlftiemlmkmyglglrq yfmsifnrfdcfvvcsgileillvesgamsplgisvlrcirllrlfkit kywtlslnlvaslnsirsiasllllflfiiifallgmqlfggrydfe dtevrrsnfdnfpqalisvfqvltgedwnsvmyngimayggptypgvlv ciyfiiilfvcgnyillnvflaiavdnlaeaesltsaqkakaeeerrrkm skglpdkseeeratvtkkleqkskgegipttaklkidefesnvnevkdp ypsadfpgddeedepeipvsprprplaelqlkekavpipeassffifsp tnkirvlchrivnatwftnfillfillssaalaaedpiradsmrnqile yfdyvftavftveivlkmttygaflhkgsfcrnyfnildllvvavslis mglessaisvvkilrvlrvlrplrainrakglkhvvqcvfvairtigni vlvttllqfmfacigvqlfkgkfyscndlskmteeecrgyyyiykdgdp tqielrprqwihndfhfdnvlsammslftvstfegwpqllykaidsnee dtgpvynnrvemaiffiiyiiliaffmmnifvgfvivtfqeqgeteykn celdknqrqcvqyalkarplrcyipknpyqyqvwyvvtssyfeylmfal imlnticlgmqhynqseqmnhisdilnvaftiiftlemvlkliafkpra yfgdpwnvfdflivigsiidvilseidtflassgglyelgggcgnvdpd esarissaffrlfrvmrlvkllnraegvrtlllwtfiksfqalpyvalli vmlffiyavigmqmfgkiamvdgtqinrnnnfqtfpqavlllfrcatge awqeillacsygklcdpesdyapgeehtcgtnfayyyfisfymlcafli inlfvavimdnfdyltrdwsilgphhldefkaiwaeydpeakgrikhld | 12 |

TABLE 1-continued

L-Type Voltage Gated Calcium Channels (CaV1) Alpha Subunits

| Name | Gene Symbol | Amino Acid Sequence | SEQ ID NO: |
|---|---|---|---|
| | | vvtllrriqpplgfgkfcphrvackrlvgmnmplnsdgtvtfnatlfal<br>vrtalkiktegnfeqaneelraiikkiwkrtsmklldqvippigddevt<br>vgkfyatfliqehfrkfmkrqeeyygyrpkkdtvqiqaglrtieeeaap<br>eihraisgdptaeeeleramveaameegifrrtgglfgqvdnflertns<br>lppvmanqrplqfaeiemeelespvfledfpqnpgthplarantnnana<br>nvaygnsshrnnpvfssicyerefigeadmpvtregplsqpcsgsgphs<br>rshvdklkrpmtqrgmpegqvppspcqlsqaehpvqkegkgptsrflet<br>pnsrnfeehvprnsahrctapatamliqealvrggldslaadanfvmat<br>gqaladacqmepeevevaatellkqespeagpclgalslrsspgppesd<br>dwgsqttlitprceayte | |

Hence, the antibodies described herein specifically bind to a polypeptide of SEQ ID NOS: 5-12, or a fragment or epitope thereof. In certain embodiments, such antibodies specifically bind to a contiguous fragment of about or at least about 5, 6, 7, 8, 9, 10, 11, 12, 13, 14, 15, 16, 17, 18, 19, 20, 21, 22, 23, 24, 25, 26, 27, 28, 29, 30, 40, or 50 or more amino acids of SEQ ID NOs: 5-12. In particular embodiments, the antibodies or antigen-binding fragments thereof specifically bind to one or more sequences in Table E1 (see Example 1; and SEQ ID NOs:1-4).

In certain embodiments, antibodies and antigen-binding fragments thereof as described herein include a heavy chain and a light chain CDR set, respectively interposed between a heavy chain and a light chain framework region (FR) set which provide support to the CDRs and define the spatial relationship of the CDRs relative to each other. As used herein, the term "CDR set" refers to the three hypervariable regions of a heavy or light chain V region. Proceeding from the N-terminus of a heavy or light chain, these regions are denoted as "CDR1," "CDR2," and "CDR3" respectively. An antigen-binding site, therefore, includes six CDRs, comprising the CDR set from each of a heavy and a light chain V region. A polypeptide comprising a single CDR, (e.g., a CDR1, CDR2 or CDR3) is referred to herein as a "molecular recognition unit." Crystallographic analysis of a number of antigen-antibody complexes has demonstrated that the amino acid residues of CDRs form extensive contact with bound antigen, wherein the most extensive antigen contact is with the heavy chain CDR3. Thus, the molecular recognition units are primarily responsible for the specificity of an antigen-binding site.

Exemplary antibody sequences are provided in Table 2 below.

TABLE 2

Exemplary Polypeptide Sequences

| Description | Sequence | SEQ ID NO: |
|---|---|---|
| Heavy chain variable region (V$_H$) Clone 1C10 | SQXXSITCTVSGFSLTSYGVHWVRQSPGKGLEWLGVIWRGGNTDYSAAFM<br>SRLIITKDNSKSQVFFKMNSLQADDTAIYYCVKKAYYYGSNYYTMDYWGQ<br>GTSVTVSS | 13 |
| V$_H$CDR1 Clone 1C10 | GFSLTSYG | 14 |
| V$_H$CDR2 Clone 1C10 | IWRGGNT | 15 |
| V$_H$CDR3 1C10 | VKKAYYYGSNYYTMDY | 16 |
| Light chain variable region (V$_L$) Clone 1C10 | DVLMTQTPLSLPVSLGDQASISCRSSQSIVHSNGNTYLEWYLQKPGQSPK<br>LLIYKVSNRFSGVPDRFSGSGSGTDFTLKISRVEAEDLGVYYCFQGSHVP<br>FTFGSGTKLEIK | 17 |
| V$_L$CDR1 Clone 1C10 | QSIVHSNGNTY | 18 |
| V$_L$CDR2 Clone 1C10 | KVS | 19 |
| V$_L$CDR3 Clone 1C10 | FQGSHVPFT | 20 |
| Heavy chain variable region (V$_H$) Clone 1E7 | KXSGYTFTEYTMHWVKQSHGKSLEWIGGINRNNGGTYYNQKVRGKATLTV<br>DKSSSTAYMELRSLTSEDSAVYYCAHRFAYWGQGTLVTVSA | 21 |

TABLE 2-continued

Exemplary Polypeptide Sequences

| Description | Sequence | SEQ ID NO: |
|---|---|---|
| $V_H$CDR1 Clone 1E7 | GYTFTEYT | 22 |
| $V_H$CDR2 Clone 1E7 | INRNNGGT | 23 |
| $V_H$CDR3 Clone 1E7 | AHRFAY | 24 |
| Light chain variable region ($V_L$) Clone 1E7 | DIVLTQSPASLAVSLGQRATISCRASESVDSYGNSFMHWYQQKPGQPPKLLIYRASNLESGIPARFSGSGSGTDFTLTINPVEADDVATYYCQQSNEDPFTFGSGTKLEIK | 25 |
| $V_L$CDR1 Clone 1E7 | ESVDSYGNSF | 26 |
| $V_L$CDR2 Clone 1E7 | RAS | 27 |
| $V_L$CDR3 Clone 1E7 | QQSNEDPFT | 28 |
| Heavy chain variable region ($V_H$) Clone 1F4 | GGLVQPGGSRKLSCAASGFTFSSFGMHWVRQAPEKGLEWVAYISSGSSTIYYADTVKGRFTISRDNPKNTLFLQMTSLRSEDTAMYYCARRGVRRPGEAMDYWGQGTSVTVSS | 29 |
| $V_H$CDR1 Clone 1F4 | GFTFSSFG | 30 |
| $V_H$CDR2 Clone 1F4 | ISSGSSTI | 31 |
| $V_H$CDR3 Clone 1F4 | ARRGVRRPGEAMDY | 32 |
| Light chain variable region ($V_L$) Clone 1F4 | DIVLTQSPASLAVSLGQRATISCRASKSVSTSGYSYMHWYQQKPGQPPKLLIYLASNLESGVPARFSGSGSGTDFTLNIHPVEEEDAATYYCQHSRELTXSEGGPSWI*N | 33 |
| $V_L$CDR1 Clone 1F4 | KSVSTSGYSY | 34 |
| $V_L$CDR2 Clone 1F4 | LAS | 35 |
| $V_L$CDR3 Clone 1F4 | QHSRELH | 36 |
| Heavy chain variable region ($V_H$) Clone 2D5 | PGASVKISCKTSGYTFTEYTMHWVKQSHGKSLEWIGGINRNNGGTYYNQKVRGKATLTVDKSSSTAYMELRSLTS*GFCSL | 37 |
| $V_H$CDR1 Clone 2D5 | GYTFTEYT | 38 |
| $V_H$CDR2 Clone 2D5 | INRNNGGT | 39 |
| $V_H$CDR3 | ----- | 40 |
| Light chain variable region (VL) Clone 2D5 | DIVLTQSPASLAVSLGQRATISCRASKSVSTSGYSYMHWYQQKPGQPPKLLIYLASNLESGVPARFSGSGSGTDFTLNIHPVEEEDAATYYCQHIRELTRSEGGPSWK*N | 41 |
| $V_L$CDR1 Clone 2D5 | KSVSTSGYSY | 42 |
| $V_L$CDR2 Clone 2D5 | LAS | 43 |

TABLE 2-continued

Exemplary Polypeptide Sequences

| Description | Sequence | SEQ ID NO: |
|---|---|---|
| $V_L$CDR3 Clone 2D5 | QHIRELT | 44 |
| Heavy chain variable region ($V_H$) Clone 5F4 | LVQPGXXLKLSCKSNEYEFPSHDMSWVRTTPEKRLELVAAINSDGGNTYY PDTMERRFIISRDNTKKTLYLQMSSLRSEDTALYYCARHSMVTPDLLTGA KGLWSLSLQ | 45 |
| $V_H$CDR1 Clone 5F4 | EYEFPSHD | 46 |
| $V_H$CDR2 Clone 5F4 | INSDGGNT | 47 |
| $V_H$CDR3 Clone 5F4 | ARHSMVTPDLL | 48 |
| Light chain variable region ($V_L$) Clone 5F4 | DIVLTQSPASLAVSLGQRATISCRASKSVSTSGYSYMHWYQQKPGQPPKL LIYLASNLESGVPARFSGSGSGTDFTLNIHPVEEEDAATYYCQHIRELTR SEGGPSWK*N | 49 |
| $V_L$CDR1 Clone 5F4 | KSVSTSGYSY | 50 |
| $V_L$CDR2 Clone 5F4 | LAS | 51 |
| $V_L$CDR3 Clone 5F4 | QHIRELTR | 52 |
| Heavy chain variable region ($V_H$) Clone 6C6 | PGASVKISCKGSGYTFTDYTMHWVKQSHAKSLEWIGVISSYSGNTNYNQK FEGKATMTVDKSSSTAYMELARLTSEDSAIYYCARH | 53 |
| $V_H$CDR1 Clone 6C6 | GYTFTDYT | 54 |
| $V_H$CDR2 Clone 6C6 | ISSYSGNT | 55 |
| $V_H$CDR3 Clone 6C6 | ----- | 56 |
| Light chain variable region ($V_L$) Clone 6C6 | DVVMTQTPLTLSVTIGQPASISCKSSQSLLDSDGKTYLNWLLQRPGQSPK RLIYLVSKLDSGVPDRFTGSGSGTDFTLKISRVEAEDLGVYYCWQGTHFP FTFGSGTKLEIK | 57 |
| $V_L$CDR1 Clone 6C6 | QSLLDSDGKTY | 58 |
| $V_L$CDR2 Clone 6C6 | LVS | 59 |
| $V_L$CDR3 Clone 6C6 | WQGTHFPFT | 60 |
| Heavy chain variable region ($V_H$) Clone 6E1 | LVKPGGSLKLSCAASGFTFSSYAMSWVRQTPEKRLEWVASISSGGSTYYP DSVKGRFTISRDNARNILYLQMSSLRSEDTAMYYCARLGDGYYPFAYWGQ GTLVTVSA | 61 |
| $V_H$CDR1 Clone 6E1 | GFTFSSYA | 62 |
| $V_H$CDR2 Clone 6E1 | ISSGGST | 63 |
| $V_H$CDR3 Clone 6E1 | ARLGDGYYPFAY | 64 |

TABLE 2-continued

Exemplary Polypeptide Sequences

| Description | Sequence | SEQ ID NO: |
|---|---|---|
| Light chain variable region (V$_L$) Clone 6E1 | ----- | 65 |
| V$_L$CDR1 Clone 6E1 | ----- | 66 |
| V$_L$CDR2 Clone 6E1 | ----- | 67 |
| V$_L$CDR3 Clone 6E1 | ----- | 68 |
| Heavy chain variable region (V$_H$) Clone 6H7 | KGXGYTFTDYTMHWVKQSHAKSLEWIGVISSYSGNTNYNQKFEGKATMTVDKSSSTAYMELARLTSEDSAIYYCARHYGYDVTFWGQGTLVTVSA | 69 |
| V$_H$CDR1 Clone 6H7 | GYTFTDYT | 70 |
| V$_H$CDR2 Clone 6H7 | ISSYSGNT | 71 |
| V$_H$CDR3 Clone 6H7 | ARHYGYDVTF | 72 |
| Light chain variable region (V$_L$) Clone 6H7 | DIVLTQSPASLAVSLGQRATISCRASKSVSTSGYSYMHWYQQKPGQPPKLLIYLASNLESGVPARFSGSGSGTDFTLNIHPVEEEXYATYYCQHIRXAYTFGGGTKL | 73 |
| V$_L$CDR1 Clone 6H7 | KSVSTSGYSY | 74 |
| V$_L$CDR2 Clone 6H7 | LAS | 75 |
| V$_L$CDR3 Clone 6H7 | QHIRELTR | 76 |
| Heavy chain variable region (V$_H$) Clone 8G1 | LVQPGGSRKLSCAASGFTFSNFGMHWVRQAPEKGLEWVAYISSGSNTIYYADTVKGRFTISRDNGKNTLFLQMTSLRSEDTAIYYCASYGNYAAYWGQGTLVTVSA | 77 |
| V$_H$CDR1 Clone 8G1 | GFTFSNFG | 78 |
| V$_H$CDR2 Clone 8G1 | ISSGSNTI | 79 |
| V$_H$CDR3 Clone 8G1 | ASYGNYAAY | 80 |
| Light chain variable region (V$_L$) Clone 8G1 | DIVLTQSPASLAVSLGQRATISCRASKSVSTSGYSYMHWYQQKPGQPPKLLIYLASNLESGVPARFSGSGSGTDFTLNIHPVEEEXAATYYCQHIRXAYTFGGGTKL | 81 |
| V$_L$CDR1 Clone 8G1 | KSVSTSGYSY | 82 |
| V$_L$CDR2 Clone 8G1 | LAS | 83 |
| V$_L$CDR3 Clone 8G1 | QHIRXAYT | 84 |
| Heavy chain variable region (V$_H$) Clone 9C3 | LSITCTVSGFSLTDYGVSWIRQSPGKGLEWLGIIWGGGSTYYNSVLKSRLSINKDNXKSQVFLKMNSLQTDDTAMYYCAKHRGDWGQGTLVTVSA | 85 |

TABLE 2-continued

Exemplary Polypeptide Sequences

| Description | Sequence | SEQ ID NO: |
|---|---|---|
| V<sub>H</sub>CDR1 Clone 9C3 | GFSLTDYG | 86 |
| V<sub>H</sub>CDR2 Clone 9C3 | IWGGGST | 87 |
| V<sub>H</sub>CDR3 Clone 9C3 | AKHRGD | 88 |
| Light chain variable region (V<sub>L</sub>) Clone 9C3 | DIVLTQSPASLAVSLGQRATISCRASKSVSTSGYSYMHWYQQKPGQPPKL LIYLASNLESGVPARFSGSGSGTDFTLNIHPVEEEXAAXYYCQHIRELTR SEGGPSWK | 89 |
| V<sub>L</sub>CDR1 Clone 9C3 | KSVSTSGYSY | 90 |
| V<sub>L</sub>CDR2 Clone 9C3 | LAS | 91 |
| V<sub>L</sub>CDR3 Clone 9C3 | STLGSLH | 92 |
| Heavy chain variable region (V<sub>H</sub>) Clone 1D2 | ----- | 93 |
| V<sub>H</sub>CDR1 Clone 1D2 | ----- | 94 |
| V<sub>H</sub>CDR2 Clone 1D2 | ----- | 95 |
| V<sub>H</sub>CDR3 Clone 1D2 | ----- | 96 |
| Light chain variable region (V<sub>L</sub>) Clone 1D2 | DIVLTQSPASLAVSLGQRATISCRASKSVSTSGYSYMHWYQQKPGQPPKL LIYLASNLESGVPARFSGSGSGTDFTLNIHPVEEEXAATYYCQHIRELTR SEGGPSWK*N | 97 |
| V<sub>L</sub>CDR1 Clone 1D2 | KSVSTSGYSY | 98 |
| V<sub>L</sub>CDR2 Clone 1D2 | LAS | 99 |
| V<sub>L</sub>CDR3 Clone 1D2 | QHIRELT | 100 |
| Heavy chain variable region (V<sub>H</sub>) Clone 5G10 | ----- | 101 |
| V<sub>H</sub>CDR1 Clone 5G10 | ----- | 102 |
| V<sub>H</sub>CDR2 Clone 5G10 | ----- | 103 |
| V<sub>H</sub>CDR3 Clone 5G10 | ----- | 104 |
| Light chain variable region (V<sub>L</sub>) Clone 5G10 | DIVLTQSPASLAVSLGQRATISCRASKSVSTSGYSYMHWYQQKPGQPPKL LIYLASNLESGVPARFSGSGSGTDFTLNIHPVEEEDAATYYCQHIRELTR SEGGRSWK | 105 |
| V<sub>L</sub>CDR1 Clone 5G10 | KSVSTSGYSY | 106 |

TABLE 2-continued

Exemplary Polypeptide Sequences

| Description | Sequence | SEQ ID NO: |
|---|---|---|
| $V_L$CDR2 Clone 5G10 | LAS | 107 |
| $V_L$CDR3 Clone 5G10 | CQHIRELTR | 108 |

Hence, in certain embodiments, an antibody, or antigen-binding fragment thereof, comprises one or more of the sequences in Table 2 (e.g., SEQ ID NOs:13-108), including combinations and variants thereof. For instance, in particular embodiments, the antibody, or antigen-binding fragment thereof, comprises the $V_H$ sequence set forth SEQ ID NO:13, and/or the $V_L$ sequence set forth in SEQ ID NO:17. In some embodiments, the antibody, or antigen-binding fragment thereof, comprises a heavy chain variable region ($V_H$) that comprises complementary determining region $V_H$CDR1, $V_H$CDR2, and/or $V_H$CDR3 sequences contained in SEQ ID NO: 13 (e.g., SEQ ID NOS: 14-16 respectively), and/or a light chain variable region ($V_L$) that comprises complementary determining region $V_L$CDR1, $V_L$CDR2, and/or $V_L$CDR3 sequence contained in SEQ ID NO:17 (e.g., SEQ ID NOS:18-20, respectively).

In some embodiments, the antibody, or antigen-binding fragment thereof, comprises the $V_H$ sequence set forth SEQ ID NO: 21, and/or the $V_L$ sequence set forth in SEQ ID NO:25. In some embodiments, the antibody, or antigen-binding fragment thereof, comprises a heavy chain variable region ($V_H$) that comprises complementary determining region $V_H$CDR1, $V_H$CDR2, and/or $V_H$CDR3 sequences contained in SEQ ID NO: 21 (e.g., SEQ ID NOS:22-24 respectively), and/or a light chain variable region (VI) that comprises complementary determining region $V_L$CDR1, $V_L$CDR2, and/or $V_L$CDR3 sequence contained in SEQ ID NO:25 (e.g., SEQ ID NOS:26-28, respectively).

In some embodiments, the antibody, or antigen-binding fragment thereof, comprises the $V_H$ sequence set forth SEQ ID NO: 29, and/or the $V_L$ sequence set forth in SEQ ID NO:33. In some embodiments, the antibody, or antigen-binding fragment thereof, comprises a heavy chain variable region (VA) that comprises complementary determining region $V_H$CDR1, $V_H$CDR2, and/or $V_H$CDR3 sequences contained in SEQ ID NO: 29 (e.g., SEQ ID NOS:30-32 respectively), and/or a light chain variable region ($V_L$) that comprises complementary determining region $V_L$CDR1, $V_L$CDR2, and/or $V_L$CDR3 sequence contained in SEQ ID NO:33 (e.g., SEQ ID NOS:34-36, respectively).

In some embodiments, the antibody, or antigen-binding fragment thereof, comprises the $V_H$ sequence set forth SEQ ID NO:37, and/or the $V_L$ sequence set forth in SEQ ID NO:41. In some embodiments, the antibody, or antigen-binding fragment thereof, comprises a heavy chain variable region ($V_H$) that comprises complementary determining region $V_H$CDR1, $V_H$CDR2, and/or $V_H$CDR3 sequences contained in SEQ ID NO: 37 (e.g., SEQ ID NOS:38-40 respectively), and/or a light chain variable region ($V_L$) that comprises complementary determining region $V_L$CDR1, $V_L$CDR2, and/or $V_L$CDR3 sequence contained in SEQ ID NO:41 (e.g., SEQ ID NOS:42-44, respectively).

In some embodiments, the antibody, or antigen-binding fragment thereof, comprises the $V_H$ sequence set forth SEQ ID NO: 45, and/or the $V_L$ sequence set forth in SEQ ID NO:49. In some embodiments, the antibody, or antigen-binding fragment thereof, comprises a heavy chain variable region ($V_H$) that comprises complementary determining region $V_H$CDR1, $V_H$CDR2, and/or $V_H$CDR3 sequences contained in SEQ ID NO: 45 (e.g., SEQ ID NOS: 46-48 respectively), and/or a light chain variable region ($V_L$) that comprises complementary determining region $V_L$CDR1, $V_L$CDR2, and/or $V_L$CDR3 sequence contained in SEQ ID NO:49 (e.g., SEQ ID NOS:50-52, respectively).

In some embodiments, the antibody, or antigen-binding fragment thereof, comprises the $V_H$ sequence set forth SEQ ID NO:53, and/or the $V_L$ sequence set forth in SEQ ID NO:57. In some embodiments, the antibody, or antigen-binding fragment thereof, comprises a heavy chain variable region ($V_H$) that comprises complementary determining region $V_H$CDR1, $V_H$CDR2, and/or $V_H$CDR3 sequences contained in SEQ ID NO: 53 (e.g., SEQ ID NOS:54-56 respectively), and/or a light chain variable region ($V_L$) that comprises complementary determining region $V_L$CDR1, $V_L$CDR2, and/or $V_L$CDR3 sequence contained in SEQ ID NO:57 (e.g., SEQ ID NOS:58-60, respectively).

In some embodiments, the antibody, or antigen-binding fragment thereof, comprises the $V_H$ sequence set forth SEQ ID NO:61, and/or the $V_L$ sequence set forth in SEQ ID NO:65. In some embodiments, the antibody, or antigen-binding fragment thereof, comprises a heavy chain variable region ($V_H$) that comprises complementary determining region $V_H$CDR1, $V_H$CDR2, and/or $V_H$CDR3 sequences contained in SEQ ID NO: 61 (e.g., SEQ ID NOS:62-64 respectively), and/or a light chain variable region ($V_L$) that comprises complementary determining region $V_L$CDR1, $V_L$CDR2, and/or $V_L$CDR3 sequence contained in SEQ ID NO:65 (e.g., SEQ ID NOS:66-68, respectively).

In some embodiments, the antibody, or antigen-binding fragment thereof, comprises the $V_H$ sequence set forth SEQ ID NO: 69, and/or the $V_L$ sequence set forth in SEQ ID NO:73. In some embodiments, the antibody, or antigen-binding fragment thereof, comprises a heavy chain variable region ($V_H$) that comprises complementary determining region $V_H$CDR1, $V_H$CDR2, and/or $V_H$CDR3 sequences contained in SEQ ID NO: 69 (e.g., SEQ ID NOS: 70-72 respectively), and/or a light chain variable region ($V_L$) that comprises complementary determining region $V_L$CDR1, $V_L$CDR2, and/or $V_L$CDR3 sequence contained in SEQ ID NO:73 (e.g., SEQ ID NOS:74-76, respectively).

In some embodiments, the antibody, or antigen-binding fragment thereof, comprises the $V_H$ sequence set forth SEQ ID NO: 77, and/or the $V_L$ sequence set forth in SEQ ID NO:81. In some embodiments, the antibody, or antigen-binding fragment thereof, comprises a heavy chain variable region ($V_H$) that comprises complementary determining region $V_H$CDR1, $V_H$CDR2, and/or $V_H$CDR3 sequences contained in SEQ ID NO: 77 (e.g., SEQ ID NOS: 78-80 respectively), and/or a light chain variable region ($V_L$) that comprises complementary determining region $V_L$CDR1, $V_L$CDR2, and/or $V_L$CDR3 sequence contained in SEQ ID NO:81 (e.g., SEQ ID NOS:82-84, respectively).

In some embodiments, the antibody, or antigen-binding fragment thereof, comprises the $V_H$ sequence set forth SEQ ID NO: 85, and/or the $V_L$ sequence set forth in SEQ ID NO:89. In some embodiments, the antibody, or antigen-binding fragment thereof, comprises a heavy chain variable region ($V_H$) that comprises complementary determining region $V_H$CDR1, $V_H$CDR2, and/or $V_H$CDR3 sequences contained in SEQ ID NO: 85 (e.g., SEQ ID NOS:86-88 respectively), and/or a light chain variable region ($V_L$) that comprises complementary determining region $V_L$CDR1, $V_L$CDR2, and/or $V_L$CDR3 sequence contained in SEQ ID NO:89 (e.g., SEQ ID NOS:90-92, respectively).

In some embodiments, the antibody, or antigen-binding fragment thereof, comprises the $V_H$ sequence set forth SEQ ID NO:93, and/or the $V_L$ sequence set forth in SEQ ID NO:97. In some embodiments, the antibody, or antigen-binding fragment thereof, comprises a heavy chain variable region ($V_H$) that comprises complementary determining region $V_H$CDR1, $V_H$CDR2, and/or $V_H$CDR3 sequences contained in SEQ ID NO: 93 (e.g., SEQ ID NOS: 94-96 respectively), and/or a light chain variable region ($V_L$) that comprises complementary determining region $V_L$CDR1, $V_L$CDR2, and/or $V_L$CDR3 sequence contained in SEQ ID NO:97 (e.g., SEQ ID NOS:98-100, respectively).

In some embodiments, the antibody, or antigen-binding fragment thereof, comprises the $V_H$ sequence set forth SEQ ID NO: 101, and/or the $V_L$ sequence set forth in SEQ ID NO:105. In some embodiments, the antibody, or antigen-binding fragment thereof, comprises a heavy chain variable region ($V_H$) that comprises complementary determining region $V_H$CDR1, $V_H$CDR2, and/or $V_H$CDR3 sequences contained in SEQ ID NO: 101 (e.g., SEQ ID NOS: 102-104 respectively), and/or a light chain variable region ($V_L$) that comprises complementary determining region $V_L$CDR1, $V_L$CDR2, and/or $V_L$CDR3 sequence contained in SEQ ID NO: 105 (e.g., SEQ ID NOS: 106-108, respectively).

In some embodiments, the CDR sequences are defined according to the rules of Kabat, Clothia, or combinations thereof (see also IMGT®, the international ImMunoGeneTics information system®).

As used herein, the term "FR set" refers to the four flanking amino acid sequences which frame the CDRs of a CDR set of a heavy or light chain V region. Some FR residues may contact bound antigen; however, FRs are primarily responsible for folding the V region into the antigen-binding site, particularly the FR residues directly adjacent to the CDRs. Within FRs, certain amino residues and certain structural features are very highly conserved. In this regard, all V region sequences contain an internal disulfide loop of around 90 amino acid residues. When the V regions fold into a binding-site, the CDRs are displayed as projecting loop motifs which form an antigen-binding surface. It is generally recognized that there are conserved structural regions of FRs which influence the folded shape of the CDR loops into certain "canonical" structures-regardless of the precise CDR amino acid sequence. Further, certain FR residues are known to participate in non-covalent interdomain contacts which stabilize the interaction of the antibody heavy and light chains.

The structures and locations of immunoglobulin variable domains may be determined by reference to Kabat, E. A. et al., Sequences of Proteins of Immunological Interest. 4th Edition. US Department of Health and Human Services. 1987, and updates thereof.

In some embodiments, the antibody is a "monoclonal antibody," which refers to a homogeneous antibody population wherein the monoclonal antibody is comprised of amino acids (naturally occurring and non-naturally occurring) that are involved in the selective binding of an epitope. Monoclonal antibodies are highly specific, being directed against a single epitope. The term "monoclonal antibody" encompasses not only intact monoclonal antibodies and full-length monoclonal antibodies, but also fragments thereof (such as Fab, Fab', F(ab')$_2$, Fv), single chain (ScFv), variants thereof, fusion proteins comprising an antigen-binding portion, humanized monoclonal antibodies, chimeric monoclonal antibodies, and any other modified configuration of the immunoglobulin molecule that comprises an antigen-binding fragment (epitope recognition site) of the required specificity and the ability to bind to an epitope. It is not intended to be limited as regards the source of the antibody or the manner in which it is made (e.g., by hybridoma, phage selection, recombinant expression, transgenic animals). The term includes whole immunoglobulins as well as the fragments, etc. described herein under the definition of "antibody."

The proteolytic enzyme papain preferentially cleaves IgG molecules to yield several fragments, two of which (the F(ab) fragments) each comprise a covalent heterodimer that includes an intact antigen-binding site. The enzyme pepsin is able to cleave IgG molecules to provide several fragments, including the F(ab')$_2$ fragment which comprises both antigen-binding sites. An Fv fragment for use according to certain embodiments can be produced by preferential proteolytic cleavage of an IgM, and on rare occasions of an IgG or IgA immunoglobulin molecule. Fv fragments are, however, more commonly derived using recombinant techniques known in the art. The Fv fragment includes a non-covalent $V_H$::$V_L$ heterodimer including an antigen-binding site which retains much of the antigen recognition and binding capabilities of the native antibody molecule. See Inbar et al., *PNAS USA.* 69:2659-2662, 1972; Hochman et al., *Biochem.* 15:2706-2710, 1976; and Ehrlich et al., *Biochem.* 19:4091-4096, 1980.

In certain embodiments, single chain Fv or scFV antibodies are contemplated. For example, Kappa bodies (III et al., Prot. Eng. 10:949-57, 1997); minibodies (Martin et al., EMBO J 13:5305-9, 1994); diabodies (Holliger et al., PNAS 90: 6444-8, 1993); or Janusins (Traunecker et al., *EMBO J* 10: 3655-59, 1991; and Traunecker et al., *Int. J. Cancer Suppl.* 7:51-52, 1992), may be prepared using standard molecular biology techniques following the teachings of the present application with regard to selecting antibodies having the desired specificity.

A single chain Fv (sFv) polypeptide is a covalently linked $V_H$::$V_L$ heterodimer which is expressed from a gene fusion including $V_H$- and $V_L$-encoding genes linked by a peptide-encoding linker. Huston et al. (*PNAS USA.* 85(16):5879-5883, 1988). A number of methods have been described to discern chemical structures for converting the naturally aggregated—but chemically separated-light and heavy polypeptide chains from an antibody V region into an sFv molecule which will fold into a three dimensional structure substantially similar to the structure of an antigen-binding site. See, e.g., U.S. Pat. Nos. 5,091,513 and 5,132,405, to Huston et al.; and U.S. Pat. No. 4,946,778, to Ladner et al.

In certain embodiments, the antibodies or antigen-binding fragments thereof are humanized. These embodiments refer to a chimeric molecule, generally prepared using recombinant techniques, having an antigen-binding site derived from an immunoglobulin from a nonhuman species and the remaining immunoglobulin structure of the molecule based upon the structure and/or sequence of a human immunoglobulin. The antigen-binding site may comprise either complete variable domains fused onto constant domains or only the CDRs grafted onto appropriate framework regions in the variable domains. Epitope binding sites may be wild-type or modified by one or more amino acid substitutions. This eliminates the constant region as an immunogen in human individuals, but the possibility of an immune response to the foreign variable region remains (LoBuglio et al., *PNAS USA* 86:4220-4224, 1989; Queen et al., *PNAS USA*. 86:10029-10033, 1988; Riechmann et al., Nature. 332:323-327, 1988). Illustrative methods for humanization of antibodies include the methods described in U.S. Pat. No. 7,462,697.

Another approach focuses not only on providing human-derived constant regions, but modifying the variable regions as well so as to reshape them as closely as possible to human form. It is known that the variable regions of both heavy and light chains contain three complementarity-determining regions (CDRs) which vary in response to the epitopes in question and determine binding capability, flanked by four framework regions (FRs) which are relatively conserved in a given species and which putatively provide a scaffolding for the CDRs. When nonhuman antibodies are prepared with respect to a particular epitope, the variable regions can be "reshaped" or "humanized" by grafting CDRs derived from nonhuman antibody on the FRs present in the human antibody to be modified. Application of this approach to various antibodies has been reported by Sato et al., *Cancer Res.* 53:851-856, 1993; Riechmann et al., *Nature* 332:323-327, 1988; Verhoeyen et al., *Science* 239:1534-1536, 1988; Kettleborough et al., *Protein Engineering.* 4:773-3783, 1991; Maeda et al., *Human Antibodies Hybridoma* 2:124-134, 1991; Gorman et al., *PNAS USA.* 88:4181-4185, 1991; Tempest et al., *Bio/Technology* 9:266-271, 1991; Co et al., *PNAS USA.* 88:2869-2873, 1991; Carter et al., *PNAS USA.* 89:4285-4289, 1992; and Co et al., *J Immunol.* 148:1149-1154, 1992. In some embodiments, humanized antibodies preserve all CDR sequences (for example, a humanized mouse antibody which contains all six CDRs from the mouse antibodies). In other embodiments, humanized antibodies have one or more CDRs (one, two, three, four, five, six) which are altered with respect to the original antibody, which are also termed one or more CDRs "derived from" one or more CDRs from the original antibody.

The antibodies, and antigen-binding fragments thereof, described herein can comprise the light chain constant regions or heavy chain constant regions (e.g., Fc regions) of any variety of immunoglobulin subtypes (e.g., IgA, IgD, IgE, IgG, IgM, including subclasses and combinations thereof, e.g., IgG1, IgG2, IgG2, IgG3, IgG4), from any variety of mammals such as mouse, human, rabbit, or goat. The "Fc region" sequence is usually derived from the heavy chain of an immunoglobulin (Ig) molecule. A typical Ig molecule is composed of two heavy chains and two light chains. The heavy chains can be divided into at least three functional regions: the Fd region, the Fc region (fragment crystallizable region), and the hinge region, the latter being found only in IgG, IgA, and IgD immunoglobulins. The Fd region comprises the variable ($V_H$) and constant (CH1) domains of the heavy chains, and together with the variable ($V_L$) and constant (CL) domains of the light chains forms the antigen-binding fragment or Fab region.

The Fc region of IgG, IgA, and IgD immunoglobulins comprises the heavy chain constant domains 2 and 3, designated respectively as CH2 and CH3 regions; and the Fc region of IgE and IgM immunoglobulins comprises the heavy chain constant domains 2, 3, and 4, designated respectively as CH2, CH3, and CH4 regions. The Fc region is mainly responsible for the immunoglobulin effector functions, which include, for example, complement fixation and binding to cognate Fc receptors of effector cells.

The hinge region (found in IgG, IgA, and IgD) acts as a flexible spacer that allows the Fab portion to move freely in space relative to the Fc region. In contrast to the constant regions, the hinge regions are structurally diverse, varying in both sequence and length among immunoglobulin classes and subclasses (see supra). The hinge region may also contain one or more glycosylation site(s), which include a number of structurally distinct types of sites for carbohydrate attachment. For example, IgA1 contains five glycosylation sites within a 17 amino acid segment of the hinge region, conferring significant resistance of the hinge region polypeptide to intestinal proteases. Residues in the hinge proximal region of the CH2 domain can also influence the specificity of the interaction between an immunoglobulin and its respective Fc receptor(s) (see, e.g., Shin et al., Intern. Rev. Immunol. 10:177-186, 1993).

The term "Fc region" or "Fc fragment" or "Fc" as used herein, thus refers to a portion of an antibody, or antigen-binding fragment thereof, which contains one or more of a CH2 region, a CH3 region, and/or a CH4 region from one or more selected immunoglobulin(s), including fragments and variants and combinations thereof. An "Fc region" may also include one or more hinge region(s) of the heavy chain constant region of an immunoglobulin. In certain embodiments, the Fc region does not contain one or more of the CH1, CL, $V_L$, and/or $V_H$ regions of an immunoglobulin.

The Fc region can comprise the CH2 region, CH3 region, CH4 region, and/or hinge region(s) of any one or more immunoglobulin classes, including but not limited to IgA, IgD, IgE, IgG, IgM, including subclasses and combinations thereof. In some embodiments, the Fc region is from an IgA immunoglobulin (e.g., mouse, human, rabbit, goat), including subclasses IgA1 and/or IgA2. In certain embodiments, the Fc region is from an IgD immunoglobulin (e.g., mouse, human, rabbit, goat). In particular embodiments, the Fc region is from an IgE immunoglobulin (e.g., mouse, human, rabbit, goat). In some embodiments, the Fc region is from an IgG immunoglobulin (e.g., mouse, human, rabbit, goat), including subclasses IgG1, IgG2, IgG2, IgG3, and/or IgG4. In certain embodiments, the Fc region is from an IgM immunoglobulin (e.g., mouse, human, rabbit, goat).

Also included are antibodies, or antigen-binding fragments thereof, which comprise "variants" of the sequences described herein (e.g., Table 2, SEQ ID NOS: 13-108). A "variant" sequence, as the term is used herein, refers to a polypeptide or polynucleotide sequence that differs from a reference sequence disclosed herein (e.g., Table 2, SEQ ID NOS: 13-108, by 1, 2, 3, 4, 5, 6, 7, 8, 9, 10, 11, 12, 13, 14, 15, 16, 17, 18, 19, 29 or more substitutions, deletions (e.g., truncations), additions, and/or insertions. Certain variants thus include fragments of a reference sequence described herein. Variant polypeptides are biologically active, that is, they continue to possess the binding activity of a reference polypeptide. Such variants may result from, for example, genetic polymorphism and/or from human manipulation.

In many instances, a biologically active variant will contain one or more conservative substitutions. A "conservative substitution" is one in which an amino acid is substituted for another amino acid that has similar properties, such that one skilled in the art of peptide chemistry would expect the secondary structure and hydropathic nature of the polypeptide to be substantially unchanged. As described above, modifications may be made in the structure of the polynucleotides and polypeptides described herein and still obtain a functional molecule that encodes a variant or derivative polypeptide with desirable characteristics. When it is desired to alter the amino acid sequence of a polypeptide to create an equivalent, or even an improved, variant or portion of a polypeptide of the invention, one skilled in the art will typically change one or more of the codons of the encoding DNA sequence according to Table A below.

TABLE A

| Amino Acids | | | Codons |
|---|---|---|---|
| Alanine | Ala | A | GCA GCC GCG GCU |
| Cysteine | Cys | C | UGC UGU |
| Aspartic acid | Asp | D | GAC GAU |
| Glutamic acid | Glu | E | GAA GAG |
| Phenylalanine | Phe | F | UUC UUU |
| Glycine | Gly | G | GGA GGC GGG GGU |
| Histidine | His | H | CAC CAU |
| Isoleucine | Ile | I | AUA AUC AUU |
| Lysine | Lys | K | AAA AAG |
| Leucine | Leu | L | UUA UUG CUA CUC CUG CUU |
| Methionine | Met | M | AUG |
| Asparagine | Asn | N | AAC AAU |
| Proline | Pro | P | CCA CCC CCG CCU |
| Glutamine | Gln | Q | CAA CAG |
| Arginine | Arg | R | AGA AGG CGA CGC CGG CGU |
| Serine | Ser | S | AGC AGU UCA UCC UCG UCU |
| Threonine | Thr | T | ACA ACC ACG ACU |
| Valine | Val | V | GUA GUC GUG GUU |
| Tryptophan | Trp | W | UGG |
| Tyrosine | Tyr | Y | UAC UAU |

For example, certain amino acids may be substituted for other amino acids in a protein structure without appreciable loss of interactive binding capacity with structures such as, for example, antigen-binding regions of antibodies or binding sites on substrate molecules. Since it is the interactive capacity and nature of a protein that defines that protein's biological functional activity, certain amino acid sequence substitutions can be made in a protein sequence, and, of course, its underlying DNA coding sequence, and nevertheless obtain a protein with like properties. It is thus contemplated that various changes may be made in the peptide sequences of the disclosed compositions, or corresponding DNA sequences which encode said peptides without appreciable loss of their utility.

In making such changes, the hydropathic index of amino acids may be considered. The importance of the hydropathic amino acid index in conferring interactive biologic function on a protein is generally understood in the art (Kyte & Doolittle, 1982, incorporated herein by reference). It is accepted that the relative hydropathic character of the amino acid contributes to the secondary structure of the resultant protein, which in turn defines the interaction of the protein with other molecules, for example, enzymes, substrates, receptors, DNA, antibodies, antigens, and the like. Each amino acid has been assigned a hydropathic index on the basis of its hydrophobicity and charge characteristics (Kyte & Doolittle, 1982). These values are: isoleucine (+4.5); valine (+4.2); leucine (+3.8); phenylalanine (+2.8); cysteine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5). It is known in the art that certain amino acids may be substituted by other amino acids having a similar hydropathic index or score and still result in a protein with similar biological activity, i.e., still obtain a biological functionally equivalent protein. In making such changes, the substitution of amino acids whose hydropathic indices are within ±2 is preferred, those within ±1 are particularly preferred, and those within ±0.5 are even more particularly preferred.

It is also understood in the art that the substitution of like amino acids can be made effectively on the basis of hydrophilicity. U.S. Pat. No. 4,554,101 (specifically incorporated herein by reference in its entirety), states that the greatest local average hydrophilicity of a protein, as governed by the hydrophilicity of its adjacent amino acids, correlates with a biological property of the protein. As detailed in U.S. Pat. No. 4,554,101, the following hydrophilicity values have been assigned to amino acid residues: arginine (+3.0); lysine (+3.0); aspartate (+3.0±1); glutamate (+3.0±1); serine (+0.3); asparagine (+0.2); glutamine (+0.2); glycine (0); threonine (−0.4); proline (−0.5±1); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4). It is understood that an amino acid can be substituted for another having a similar hydrophilicity value and still obtain a biologically equivalent, and in particular, an immunologically equivalent protein. In such changes, the substitution of amino acids whose hydrophilicity values are within ±2 is preferred, those within ±1 are particularly preferred, and those within ±0.5 are even more particularly preferred.

As outlined above, amino acid substitutions are generally therefore based on the relative similarity of the amino acid side-chain substituents, for example, their hydrophobicity, hydrophilicity, charge, size, and the like. Exemplary substitutions that take various of the foregoing characteristics into consideration are well known to those of skill in the art and include: arginine and lysine; glutamate and aspartate; serine and threonine; glutamine and asparagine; and valine, leucine and isoleucine.

Amino acid substitutions may further be made on the basis of similarity in polarity, charge, solubility, hydrophobicity, hydrophilicity and/or the amphipathic nature of the residues. For example, negatively charged amino acids include aspartic acid and glutamic acid; positively charged amino acids include lysine and arginine; and amino acids with uncharged polar head groups having similar hydrophilicity values include leucine, isoleucine and valine; glycine and alanine; asparagine and glutamine; and serine, threonine, phenylalanine and tyrosine. Other groups of amino acids that may represent conservative changes include: (1)

ala, pro, gly, glu, asp, gln, asn, ser, thr; (2) cys, ser, tyr, thr; (3) val, ile, leu, met, ala, phe; (4) lys, arg, his; and (5) phe, tyr, trp, his.

A variant may also, or alternatively, contain non-conservative changes. In a certain embodiment, variant polypeptides differ from a native or reference sequence by substitution, deletion or addition of about or fewer than about 10, 9, 8, 7, 6, 5, 4, 3, 2 amino acids, or even 1 amino acid. Variants may also (or alternatively) be modified by, for example, the deletion or addition of amino acids that have minimal influence on the immunogenicity, secondary structure, enzymatic activity, and/or hydropathic nature of the polypeptide.

In general, variants will display at least about 30%, 40%, 50%, 55%, 60%, 65%, 70%, 75%, 80%, 85%, 90%, 91%, 92%, 93%, 94%, 95%, 96%, 97%, 98%, 99% similarity or sequence identity or sequence homology to a reference polypeptide sequence (e.g., Table 2, SEQ ID NOs: 13-108). Moreover, sequences differing from the reference sequences by the addition (e.g., C-terminal addition, N-terminal addition, both), deletion, truncation, insertion, or substitution (e.g., conservative substitution) of about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 55, 60, 65, 70, 75, 80, 85, 90, 95, or 100 amino acids (including all integers and ranges in between) but which retain the properties or activities of a parent or reference polypeptide sequence are contemplated.

In some embodiments, variant polypeptides differ from reference sequence by at least one but by less than 50, 40, 30, 20, 15, 10, 9, 8, 7, 6, 5, 4, 3 or 2 amino acid residue(s). In other embodiments, variant polypeptides differ from a reference sequence by at least 1% but less than 20%, 15%, 10% or 5% of the residues. (If this comparison requires alignment, the sequences should be aligned for maximum similarity. In some instances, "looped" out sequences from deletions or insertions, or mismatches, are considered differences.

Calculations of sequence similarity or sequence identity between sequences (the terms are used interchangeably herein) are performed as follows. To determine the percent identity of two amino acid sequences, or of two nucleic acid sequences, the sequences are aligned for optimal comparison purposes (e.g., gaps can be introduced in one or both of a first and a second amino acid or nucleic acid sequence for optimal alignment and non-homologous sequences can be disregarded for comparison purposes). In certain embodiments, the length of a reference sequence aligned for comparison purposes is at least 30%, preferably at least 40%, more preferably at least 50%, 60%, and even more preferably at least 70%, 80%, 90%, 100% of the length of the reference sequence. The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position.

The percent identity between the two sequences is a function of the number of identical positions shared by the sequences, taking into account the number of gaps, and the length of each gap, which need to be introduced for optimal alignment of the two sequences.

The comparison of sequences and determination of percent identity between two sequences can be accomplished using a mathematical algorithm. In a certain embodiment, the percent identity between two amino acid sequences is determined using the Needleman and Wunsch, (J. Mol. Biol. 48: 444-453, 1970) algorithm which has been incorporated into the GAP program in the GCG software package, using either a Blossum 62 matrix or a PAM250 matrix, and a gap weight of 16, 14, 12, 10, 8, 6, or 4 and a length weight of 1, 2, 3, 4, 5, or 6. In certain embodiments, the percent identity between two nucleotide sequences is determined using the GAP program in the GCG software package, using a NWSgapdna.CMP matrix and a gap weight of 40, 50, 60, 70, or 80 and a length weight of 1, 2, 3, 4, 5, or 6. A preferred set of parameters includes a Blossum 62 scoring matrix with a gap penalty of 12, a gap extend penalty of 4, and a frameshift gap penalty of 5.

The percent identity between two amino acid or nucleotide sequences can be determined using the algorithm of E. Meyers and W. Miller (*Cabios.* 4:11-17, 1989) which has been incorporated into the ALIGN program (version 2.0), using a PAM120 weight residue table, a gap length penalty of 12 and a gap penalty of 4.

The nucleic acid and protein sequences described herein can be used as a "query sequence" to perform a search against public databases to, for example, identify other family members or related sequences. Such searches can be performed using the NBLAST and XBLAST programs (version 2.0) of Altschul, et al., (1990, *J. Mol. Biol,* 215: 403-10). BLAST nucleotide searches can be performed with the NBLAST program, score=100, wordlength=12 to obtain nucleotide sequences homologous to nucleic acid molecules of the invention. BLAST protein searches can be performed with the XBLAST program, score=50, wordlength=3 to obtain amino acid sequences homologous to protein molecules of the invention. To obtain gapped alignments for comparison purposes, Gapped BLAST can be utilized as described in Altschul et al., (*Nucleic Acids Res.* 25: 3389-3402, 1997). When utilizing BLAST and Gapped BLAST programs, the default parameters of the respective programs (e.g., XBLAST and NBLAST) can be used.

In one embodiment, as noted above, polynucleotides and/or polypeptides can be evaluated using a BLAST alignment tool. A local alignment consists simply of a pair of sequence segments, one from each of the sequences being compared. A modification of Smith-Waterman or Sellers algorithms will find all segment pairs whose scores cannot be improved by extension or trimming, called high-scoring segment pairs (HSPs). The results of the BLAST alignments include statistical measures to indicate the likelihood that the BLAST score can be expected from chance alone.

The raw score, S, is calculated from the number of gaps and substitutions associated with each aligned sequence wherein higher similarity scores indicate a more significant alignment. Substitution scores are given by a look-up table (see PAM, BLOSUM).

Gap scores are typically calculated as the sum of G, the gap opening penalty and L, the gap extension penalty. For a gap of length n, the gap cost would be G+Ln. The choice of gap costs, G and L is empirical, but it is customary to choose a high value for G ($10^{-15}$), e.g., 11, and a low value for L (1-2) e.g., 1.

The bit score, S', is derived from the raw alignment score S in which the statistical properties of the scoring system used have been taken into account. Bit scores are normalized with respect to the scoring system, therefore they can be used to compare alignment scores from different searches. The terms "bit score" and "similarity score" are used interchangeably. The bit score gives an indication of how good the alignment is; the higher the score, the better the alignment.

The E-Value, or expected value, describes the likelihood that a sequence with a similar score will occur in the database by chance. It is a prediction of the number of different alignments with scores equivalent to or better than S that are expected to occur in a database search by chance. The smaller the E-Value, the more significant the alignment. For example, an alignment having an E value of $e^{-117}$ means that a sequence with a similar score is very unlikely to occur simply by chance. Additionally, the expected score for aligning a random pair of amino acids is required to be negative, otherwise long alignments would tend to have high score independently of whether the segments aligned were related. Additionally, the BLAST algorithm uses an appropriate substitution matrix, nucleotide or amino acid and for gapped alignments uses gap creation and extension penalties. For example, BLAST alignment and comparison of polypeptide sequences are typically done using the BLOSUM62 matrix, a gap existence penalty of 11 and a gap extension penalty of 1.

In one embodiment, sequence similarity scores are reported from BLAST analyses done using the BLOSUM62 matrix, a gap existence penalty of 11 and a gap extension penalty of 1.

In a particular embodiment, sequence identity/similarity scores provided herein refer to the value obtained using GAP Version 10 (GCG, Accelrys, San Diego, Calif.) using the following parameters: % identity and % similarity for a nucleotide sequence using GAP Weight of 50 and Length Weight of 3, and the nwsgapdna.cmp scoring matrix; % identity and % similarity for an amino acid sequence using GAP Weight of 8 and Length Weight of 2, and the BLOSUM62 scoring matrix (Henikoff and Henikoff, *PNAS USA*. 89:10915-10919, 1992). GAP uses the algorithm of Needleman and Wunsch (*J Mol Biol.* 48:443-453, 1970) to find the alignment of two complete sequences that maximizes the number of matches and minimizes the number of gaps.

In one particular embodiment, the variant polypeptide comprises an amino acid sequence that can be optimally aligned with a reference polypeptide sequence (see, e.g., the Tables, the Sequence Listing; SEQ ID NOs:1-108) to generate a BLAST bit scores or sequence similarity scores of at least about 50, 60, 70, 80, 90, 100, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, 800, 810, 820, 830, 840, 850, 860, 870, 880, 890, 900, 910, 920, 930, 940, 950, 960, 970, 980, 990, 1000, or more, including all integers and ranges in between, wherein the BLAST alignment used the BLOSUM62 matrix, a gap existence penalty of 11, and a gap extension penalty of 1.

As noted above, a reference polypeptide may be altered in various ways including amino acid substitutions, deletions, truncations, additions, and insertions. Methods for such manipulations are generally known in the art. For example, amino acid sequence variants of a reference polypeptide can be prepared by mutations in the DNA. Methods for mutagenesis and nucleotide sequence alterations are well known in the art. See, for example, Kunkel (*PNAS USA.* 82: 488-492, 1985); Kunkel et al., (*Methods in Enzymol.* 154: 367-382, 1987), U.S. Pat. No. 4,873,192, Watson, J. D. et al., ("Molecular Biology of the Gene," Fourth Edition, Benjamin/Cummings, Menlo Park, Calif., 1987) and the references cited therein. Guidance as to appropriate amino acid substitutions that do not affect biological activity of the protein of interest may be found in the model of Dayhoff et al., (1978) Atlas of Protein Sequence and Structure (Natl. Biomed. Res. Found., Washington, D.C.).

Methods for screening gene products of combinatorial libraries made by such modifications, and for screening cDNA libraries for gene products having a selected property are known in the art. Such methods are adaptable for rapid screening of the gene libraries generated by combinatorial mutagenesis of reference polypeptides. As one example, recursive ensemble mutagenesis (REM), a technique which enhances the frequency of functional mutants in the libraries, can be used in combination with the screening assays to identify polypeptide variants (Arkin and Yourvan, *PNAS USA* 89: 7811-7815, 1992; Delgrave et al., *Protein Engineering.* 6: 327-331, 1993).

Also included are antibodies, or antigen-binding fragments thereof, which "competitively inhibit" the binding of the antibodies described herein (see, e.g., Example 1) to a human or mouse L-type voltage-gated calcium channel alpha 1 subunit polypeptide. Methods for determining mAb specificity and affinity by competitive inhibition can be found, for example, in Harlow, et al., Antibodies: A Laboratory Manual, Cold Spring Harbor Laboratory Press, Cold Spring Harbor, N.Y., 1988), Colligan et al., eds., Current Protocols in Immunology, Greene Publishing Assoc. and Wiley Interscience, N.Y., (1992, 1993); Muller, Meth. Enzymol. 92:589-601, 1983; and Jia, X-C. et al., J. Immunol. Methods 288:91-98, 2004, each of which is incorporated reference.

Particular embodiments include antibodies, or antigen-binding fragments thereof, which competitively inhibit the binding of an antibody to an amino acid sequence on a human or mouse L-type voltage-gated calcium channel (SEQ ID NOs: 1-4). In specific embodiments, the antibody (which is competitively inhibited) is a monoclonal antibody, for example, a whole monoclonal antibody such as an IgG antibody, as described herein. In particular embodiments, the antibody (which is competitively inhibited) is an IgG1 or IgG2a immunoglobulin subtype.

In certain embodiments, the antibody, or antigen-binding fragment thereof, is conjugated or covalently attached to a detectable entity, for example, to facilitate detection. Exemplary detectable entities include, without limitation, iodine-based labels, radioisotopes, fluorophores/fluorescent dyes, and nanoparticles.

Exemplary iodine-based labels include diatrizoic acid (Hypaque®, GE Healthcare) and its anionic form, diatrizoate. Diatrizoic acid is a radio-contrast agent used in advanced X-ray techniques such as CT scanning. Also included are iodine radioisotopes, described below.

Exemplary radioisotopes that can be used as detectable entities include $^{32}P$, $^{33}P$, $^{35}S$, $^{3}H$, $^{18}F$, 11C, $^{13}N$, $^{15}O$, $^{111}In$, $^{169}Yb$, $^{99}mTC$, $^{55}Fe$, and isotopes of iodine such as $^{123}I$, $^{124}I$, $^{125}I$, and $^{131}I$. These radioisotopes have different half-lives, types of decay, and levels of energy which can be tailored to match the needs of a particular protocol.

Examples of fluorophores or fluorochromes that can be used as directly detectable entities include fluorescein, tetramethylrhodamine, Texas Red, Oregon Green®, and a number of others (e.g., Haugland, Handbook of Fluorescent Probes—9th Ed., 2002, Molec. Probes, Inc., Eugene OR; Haugland, The Handbook: A Guide to Fluorescent Probes and Labeling Technologies-10th Ed., 2005, Invitrogen, Carlsbad, CA). Also included are light-emitting or otherwise detectable dyes. The light emitted by the dyes can be visible light or invisible light, such as ultraviolet or infrared light. In exemplary embodiments, the dye may be a fluorescence resonance energy transfer (FRET) dye; a xanthene dye, such as fluorescein and rhodamine; a dye that has an amino group in the alpha or beta position (such as a naphthylamine dye, 1-dimethylaminonaphthyl-5-sulfonate, 1-anilino-8-naphthalende sulfonate and 2-p-touidinyl-6-naphthalene sulfonate); a dye that has 3-phenyl-7-isocyanatocoumarin; an acridine, such as 9-isothiocyanatoacridine and acridine orange; a pyrene, a bensoxadiazole and a stilbene; a dye that has 3-(ε-carboxypentyl)-3'-ethyl-5,5'-dimethyloxacarbocyanine (CYA); 6-carboxy fluorescein (FAM); 5&6-carboxyrhodamine-110 (R110); 6-carboxyrhodamine-6G (R6G); N,N,N', N'-tetramethyl-6-carboxyrhodamine (TAMRA); 6-carboxy-X-rhodamine (ROX); 6-carboxy-4',5'-dichloro-2',7'-dimethoxyfluorescein (JOE); ALEXA FLUOR™; Cy2; Texas Red and Rhodamine Red; 6-carboxy-2',4,7,7'-tetrachlorofluorescein (TET); 6-carboxy-2',4,4',5',7,7'-hexachlorofluorescein (HEX); 5-carboxy-2',4',5',7'-tetrachlorofluorescein (ZOE); NAN; NED; Cy3; Cy3.5; Cy5; Cy5.5; Cy7; and Cy7.5; IR800CW, ICG, Alexa Fluor 350; Alexa Fluor 488; Alexa Fluor 532; Alexa Fluor 546; Alexa Fluor 568; Alexa Fluor 594; Alexa Fluor 647; Alexa Fluor 680, or Alexa Fluor 750.

Nanoparticles usually range from about 1-1000 nm in size and include diverse chemical structures such as gold and silver particles and quantum dots. When irradiated with angled incident white light, silver or gold nanoparticles ranging from about 40-120 nm will scatter monochromatic light with high intensity. The wavelength of the scattered light is dependent on the size of the particle. Four to five different particles in close proximity will each scatter monochromatic light, which when superimposed will give a specific, unique color. Derivatized nanoparticles such as silver or gold particles can be attached to a broad array of molecules including, proteins, antibodies, small molecules, receptor ligands, and nucleic acids. Specific examples of nanoparticles include metallic nanoparticles and metallic nanoshells such as gold particles, silver particles, copper particles, platinum particles, cadmium particles, composite particles, gold hollow spheres, gold-coated silica nanoshells, and silica-coated gold shells. Also included are silica, latex, polystyrene, polycarbonate, polyacrylate, PVDF nanoparticles, and colored particles of any of these materials.

Quantum dots are fluorescing crystals about 1-5 nm in diameter that are excitable by light over a large range of wavelengths. Upon excitation by light having an appropriate wavelength, these crystals emit light, such as monochromatic light, with a wavelength dependent on their chemical composition and size. Quantum dots such as CdSe, ZnSe, InP, or InAs possess unique optical properties; these and similar quantum dots are available from a number of commercial sources (e.g., NN-Labs, Fayetteville, AR; Ocean Nanotech, Fayetteville, AR; Nanoco Technologies, Manchester, UK; Sigma-Aldrich, St. Louis, MO).

Antibodies may be prepared by any of a variety of techniques known to those of ordinary skill in the art. See, e.g., Harlow and Lane, Antibodies: A Laboratory Manual, Cold Spring Harbor Laboratory, 1988. Monoclonal antibodies specific for a polypeptide of interest may be prepared, for example, using the technique of Kohler and Milstein, Eur. J. Immunol. 6:511-519, 1976, and improvements thereto. Also included are methods that utilize transgenic animals such as mice to express human antibodies. See, e.g., Neuberger et al., Nature Biotechnology 14:826, 1996; Lonberg et al., Handbook of Experimental Pharmacology 113:49-101, 1994; and Lonberg et al., Internal Review of Immunology 13:65-93, 1995. Particular examples include the VELOCIMMUNE® platform by REGERNEREX® (see, e.g., U.S. Pat. No. 6,596,541). Antibodies can also be prepared by recombinant techniques, described herein and known in the art.

The antibodies described herein can be used in any of the therapeutic methods and compositions described herein.

Polynucleotides, Host Cells, and Methods of Production

Certain embodiments relate to polynucleotides that encode the antibodies, and antigen-binding fragments thereof, and vectors that comprise such polynucleotides, for example, where the polynucleotides are operably linked to one or more regulatory elements. Also included are recombinant host cells that comprise such polynucleotides, vectors, antibodies, and antigen-binding fragments thereof, in addition to methods of recombinant production of the foregoing.

Antibodies and antigen-binding fragments thereof may be prepared using standard techniques. In particular embodiments, an antibody, or antigen-binding fragment thereof, is expressed as a recombinant protein in an expression system, as described herein and known in the art.

Polynucleotides can contain one or multiple copies of a nucleic acid encoding an antibody, or antigen-binding fragment thereof.

Suitable vectors can be chosen or constructed, containing appropriate regulatory sequences, including promoter sequences, terminator sequences, polyadenylation sequences, enhancer sequences, marker genes and other sequences as appropriate. Vectors may be plasmids, viral e.g., phage, or phagemid, as appropriate. For further details see, for example, Molecular Cloning: a Laboratory Manual: 2nd edition, Sambrook et al., 1989, Cold Spring Harbor Laboratory Press. Many known techniques and protocols for manipulation of nucleic acid, for example, in preparation of nucleic acid constructs, mutagenesis, sequencing, introduction of DNA into cells and gene expression, and analysis of proteins, are described in detail in Current Protocols in Molecular Biology, Second Edition, Ausubel et al. eds., John Wiley & Sons, 1992, or subsequent updates thereto.

As will be understood by those of skill in the art, it may be advantageous in some instances to produce polypeptide-encoding nucleotide sequences possessing non-naturally occurring codons. For example, codons preferred by a particular prokaryotic or eukaryotic host can be selected to increase the rate of protein expression or to produce a recombinant RNA transcript having desirable properties, such as a half-life which is longer than that of a transcript generated from the naturally occurring sequence. Such polynucleotides are commonly referred to as "codon-optimized." Any of the polynucleotides described herein may be utilized in a codon-optimized form. In certain embodiments, a polynucleotide can be codon optimized for use in specific bacteria such as E. coli or yeast such as S. cerevisiae (see, e.g., Burgess-Brown et al., Protein Expr Purif. 59:94-102, 2008).

In some embodiments, nucleic acids or vectors encoding an antibody, or an antigen-binding fragment thereof, are introduced directly into a host cell, and the cell is incubated under conditions sufficient to induce expression of the encoded polypeptide(s). Therefore, according to certain related embodiments, there is provided a recombinant host cell which comprises a polynucleotide that encodes one or more antibodies, or antigen-binding fragments thereof, described herein, optionally in combination with other components of an antibody (e.g., Fc regions), and which optionally comprise additional exogenous polynucleotides.

Expression of antibodies, or antigen-binding fragments thereof, in the host cell may be achieved by culturing the recombinant host cells (containing the polynucleotide(s)) under appropriate conditions. Following production by expression, the antibodies, or antigen-binding fragments thereof, may be isolated and/or purified using any suitable technique, and then used as desired. The term "host cell" is used to refer to a cell into which has been introduced, or which is capable of having introduced into it, a nucleic acid sequence encoding one or more of the antibodies, or antigen-binding fragments thereof, described herein. The term includes the progeny of the parent cell, whether or not the progeny are identical in morphology or in genetic make-up to the original parent, so long as the selected gene is present. Host cells may be chosen for certain characteristics, for instance, the expression of aminoacyl tRNA synthetase(s) that can incorporate unnatural amino acids into the antibody, or antigen-binding fragment thereof.

Systems for cloning and expression of a heterologous or recombinant protein in a variety of different host cells are well known. Suitable host cells include mammalian cells, bacteria, yeast, and baculovirus systems. Mammalian cell lines available in the art for expression of a proteins include Chinese hamster ovary (CHO) cells, HeLa cells, baby hamster kidney cells, HEK-293 cells, NSO mouse melanoma cells and many others. Additional examples of useful mammalian host cell lines include monkey kidney CV1 line transformed by SV40 (COS-7, ATCC CRL 1651); human embryonic kidney line (293 or 293 cells sub-cloned for growth in suspension culture, Graham et al., *J. Gen Virol.* 36:59 (1977)); baby hamster kidney cells (BHK, ATCC CCL 10); mouse sertoli cells (TM4, Mather, *Biol. Reprod.* 23:243-251 (1980)); monkey kidney cells (CV1 ATCC CCL 70); African green monkey kidney cells (VERO-76, ATCC CRL-1587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor (MMT 060562, ATCC CCL51); TR1 cells (Mather et al., *Annals N.Y. Acad. Sci.* 383:44-68 (1982)); MRC 5 cells; FS4 cells; and a human hepatoma line (Hep G2). Other useful mammalian host cell lines include Chinese hamster ovary (CHO) cells, including DHFR-CHO cells (Urlaub et al., *PNAS USA* 77:4216 (1980)); and myeloma cell lines such as NSO and Sp2/0. For a review of certain mammalian host cell lines suitable for antibody production, see, e.g., Yazaki and Wu, Methods in Molecular Biology, Vol. 248 (B. K. C Lo, ed., Humana Press, Totowa, N.J., 2003), pp. 255-268. Certain preferred mammalian cell expression systems include CHO and HEK293-cell based expression systems including 293F cells. Mammalian expression systems can utilize attached cell lines, for example, in T-flasks, roller bottles, or cell factories, or suspension cultures, for example, in 1L and 5L spinners, 5L, 14L, 40L, 100L and 200L stir tank bioreactors, or 20/50L and 100/200L WAVE bioreactors, among others known in the art.

A common, preferred bacterial host is *E. coli*. The expression of proteins in prokaryotic cells such as *E. coli* is well established in the art. For a review, see for example, Pluckthun, *A. Bio/Technology.* 9:545-551 (1991). Expression in eukaryotic cells in culture is also available to those skilled in the art as an option for recombinant production of polypeptides (see Ref, *Curr. Opinion Biotech.* 4:573-576, 1993; and Trill et al., *Curr. Opinion Biotech.* 6:553-560, 1995). In specific embodiments, protein expression may be controlled by a T7 RNA polymerase (e.g., pET vector series). These and related embodiments may utilize the expression host strain BL21(DE3), a λDE3 lysogen of BL21 that supports T7-mediated expression and is deficient in lon and ompT proteases for improved target protein stability. Also included are expression host strains carrying plasmids encoding tRNAs rarely used in *E. coli*, such as Rosetta™ (DE3) and Rosetta 2 (DE3) strains. Cell lysis and sample handling may also be improved using reagents such as Benzonase® nuclease and BugBuster® Protein Extraction Reagent. For cell culture, auto-inducing media can improve the efficiency of many expression systems, including high-throughput expression systems. Media of this type (e.g., Overnight Express™ Autoinduction System) gradually elicit protein expression through metabolic shift without the addition of artificial inducing agents such as IPTG. Particular embodiments employ hexahistidine tags (such as His●Tag® fusions), followed by immobilized metal affinity chromatography (IMAC) purification, or related techniques. In certain aspects, however, clinical grade proteins can be isolated from *E. coli* inclusion bodies, without or without the use of affinity tags (see, e.g., Shimp et al., *Protein Expr Purif.* 50:58-67, 2006). As a further example, certain embodiments may employ a cold-shock induced *E. coli* high-yield production system, because over-expression of proteins in *Escherichia coli* at low temperature improves their solubility and stability (see, e.g., Qing et al., *Nature Biotechnology.* 22:877-882, 2004).

In addition, a host cell strain may be chosen for its ability to modulate the expression of the inserted sequences or to process the expressed protein in the desired fashion. Such modifications of the polypeptide include, but are not limited to, post-translational modifications such as acetylation, carboxylation, glycosylation, phosphorylation, lipidation, and acylation. Post-translational processing, which cleaves a "prepro" form of the protein may also be used to facilitate correct insertion, folding and/or function. Different host cells such as yeast, CHO, HeLa, MDCK, HEK293, and W138, in addition to bacterial cells, which have or even lack specific cellular machinery and characteristic mechanisms for such post-translational activities, may be chosen to ensure the correct modification and processing of the protein (e.g., antibody) of interest.

For long-term, high-yield production of recombinant proteins, stable expression is generally preferred. For example, cell lines that stably express a polynucleotide of interest may be transformed using expression vectors which may contain viral origins of replication and/or endogenous expression elements and a selectable marker gene on the same or on a separate vector. Following the introduction of the vector, cells may be allowed to grow for about 1-2 days in an enriched media before they are switched to selective media. The purpose of the selectable marker is to confer resistance to selection, and its presence allows growth and recovery of cells which, successfully express the introduced sequences. Resistant clones of stably transformed cells may be proliferated using tissue culture techniques appropriate to the cell type. Transient production, such as by transient transfection or infection, can also be employed. Exemplary mammalian expression systems that are suitable for transient production include HEK293 (e.g., 293F cells) and CHO-based systems.

Host cells transformed with a polynucleotide sequence of interest may be cultured under conditions suitable for the expression and recovery of the protein from cell culture. Certain specific embodiments utilize serum free cell expression systems. Examples include HEK293 cells and CHO cells that can grow on serum free medium (see, e.g., Rosser et al., *Protein Expr. Purif.* 40:237-43, 2005; and U.S. Pat. No. 6,210,922).

The protein(s) produced by a recombinant cell can be purified and characterized according to a variety of techniques known in the art. Exemplary systems for performing protein purification and analyzing protein purity include fast protein liquid chromatography (FPLC) (e.g., AKTA and Bio-Rad FPLC systems), high-performance liquid chromatography (HPLC) (e.g., Beckman and Waters HPLC). Exemplary chemistries for purification include ion exchange chromatography (e.g., Q, S), size exclusion chromatography, salt gradients, affinity purification (e.g., Ni, Co, FLAG, maltose, glutathione, protein A/G), gel filtration, reverse-phase, ceramic HyperD® ion exchange chromatography, and hydrophobic interaction columns (HIC), among others known in the art. Also included are analytical methods such as SDS-PAGE (e.g., coomassie, silver stain), immunoblot, Bradford, and ELISA, which may be utilized during any step of the production or purification process, typically to measure the purity of the protein composition.

Also included are methods of concentrating recombinantly produced proteins, e.g., antibodies. Examples include lyophilization, which is typically employed when the solution contains few soluble components other than the protein of interest. Lyophilization is often performed after HPLC run, and can remove most or all volatile components from the mixture. Also included are ultrafiltration techniques, which typically employ one or more selective permeable membranes to concentrate a protein solution. The membrane allows water and small molecules to pass through and retains the protein; the solution can be forced against the membrane by mechanical pump, gas pressure, or centrifugation, among other techniques.

In certain embodiments, the antibodies, or antigen-binding fragments thereof, have a purity of at least about 90%, as measured according to routine techniques in the art. In certain embodiments, such as diagnostic compositions or certain therapeutic compositions, the antibodies, or antigen-binding fragments thereof, have a purity of at least about 95%. In specific embodiments, such as therapeutic or pharmaceutical compositions, the antibodies, or antigen-binding fragments thereof, have a purity of at least about 97% or 98% or 99%. In other embodiments, such as when being used as reference or research reagents, the antibodies, or antigen-binding fragments thereof, can be of lesser purity, and may have a purity of at least about 50%, 60%, 70%, or 80%. Purity can be measured overall or in relation to selected components, such as other proteins, e.g., purity on a protein basis.

In certain embodiments, the compositions described here are about substantially endotoxin free, including, for example, about 95% endotoxin free, preferably about 99% endotoxin free, and more preferably about 99.99% endotoxin free. The presence of endotoxins can be detected according to routine techniques in the art, as described herein. In specific embodiments, the antibodies, or antigen-binding fragments thereof, are made from a eukaryotic cell such as a mammalian or human cell in substantially serum free media.

Methods of Use

Embodiments include methods relating to the use of the antibodies and antigen-binding fragments thereof described herein. In particular embodiments, such methods comprise contacting a cell expressing an L-type voltage-gated calcium channel with an antibody or antigen-binding fragment thereof described herein, thereby modulating the activity of the L-type voltage gated calcium channel. In some aspects, the antibody or antigen-binding fragment specifically binds to the channel. In some embodiments, the antibody or antigen-binding fragment specifically binds to an extracellular pore loop of an alpha 1 subunit of the L-type voltage gated calcium channel. In specific embodiments, the antibody or antigen-binding fragment thereof specifically binds to the extracellular pore loop between transmembrane segments S5 an S6 of domain 1 of the alpha one subunit. The alpha 1 subunit can belong to a Cav1.1, Cav1.2, Cav1.3, or Cav1.4 calcium channel, or any isoform or variant thereof. In certain embodiments, the cell is an immune cell, such as a hematopoietic cell.

Certain embodiments provide methods for modulating the activity of a cell comprising contacting the cell with an antibody or antigen binding fragment thereof as described herein. In some embodiments, the cell expresses an L-type voltage gated calcium channel. In some embodiments, the antibody or antigen-binding fragment thereof increases the cellular activity of the cell. In some embodiments, the antibody or antigen-binding fragment thereof decreases the cellular activity of the cell.

Particular embodiments relate to methods of modulating an immune response in a subject comprising administering to the subject an effective amount of an antibody or antigen-binding fragment thereof described herein. In some embodiments, the antibody or antigen-binding fragment thereof contacts an immune cell expressing an L-type voltage-gated calcium channel and modulates an activity of the immune cell. In certain embodiments, administering an antibody or antigen-binding fragment described herein increases an immune response in the subject. In some embodiments, administering an antibody or antigen-binding fragment described herein decreases an immune response in the subject.

Certain embodiments relate to methods of treating a disease in a subject comprising administering to the subject an effective amount of an antibody or antigen-binding fragment thereof as described herein. In some embodiments, the disease is an inflammatory disease. In some embodiments, the disease is a cancer.

Particular embodiments relate to modulating activity of an L-type voltage-gated calcium channel. Modulating activity refers to increasing activity, decreasing activity, or a combination of both. In some aspects, activity of the channel refers to the calcium conductance of the channel. Methods of altering channel activity can include altering calcium conductance by changing the probabilities the channel is found in an open or closed conformation, altering the voltage thresholds that trigger conversion into an open conformation, changing the duration of time the channel is open following activation of the channel, or altering the calcium conductance of the channel when it is in an open or closed conformation.

In some embodiments, an antibody or antigen binding fragment thereof as described herein contacts an L-type voltage-gated calcium channel and thereby modulates the activity of the channel. In some embodiments, the antibody or antigen-binding fragment thereof inhibits activity of the L-type voltage gated channel. In particular embodiments, inhibiting activity of an L-type voltage-gated calcium channel reduces activity by a statistically significant amount. In particular embodiments, inhibiting activity of an L-type voltage-gated calcium channel results in a decrease in channel activity of 5%, 6%, 7%, 8%, 9%, 10%, 11%, 12%, 13%, 14%, 15%, 16%, 17%, 18%, 19%, 20%, 25%, 30%, 35%, 40%, 45%, 50%, 55%, 60%, 65%, 70%, 75%, 80%, 85%, 90%, 95%, or 100% (including all integers and ranges in between).

In some embodiments, the antibody or antigen-binding fragment increases activity of the L-type voltage gated channel. In particular embodiments, increasing activity of an L-type voltage-gated calcium channel increases the activity by a statistically significant amount. In particular embodiments, increasing activity of an L-type voltage-gated calcium channel results in an increase in channel activity of a 5%, 6%, 7%, 8%, 9%, 10%, 11%, 12%, 13%, 14%, 15%, 16%, 17%, 18%, 19%, 20%, 25%, 30%, 35%, 40%, 45%, 50%, 55%, 60%, 65%, 70%, 75%, 80%, 85%, 90%, 95%, or 100% (including all integers and ranges in between). In certain embodiments, increasing in channel activity results in a 2-fold, 3-fold, 4-fold, 5-fold, 6-fold, 7-fold, 8-fold, 9-fold, 10-fold, 20-fold, 30-fold, 40-fold, 50-fold, 60-fold, 70-fold, 80-fold, 90-fold, 100-fold, 200-fold, 300-fold, 400-fold, 500-fold, 1,000-fold, 10,000-fold, or greater than 10,000-fold increase (including all integers and ranges in between) of channel activity.

In certain embodiments, modulation of activity of an L-type voltage-gated calcium channel is quantified by standard techniques known in the art. In some embodiments, modulation of activity of an L-type voltage-gated calcium channel is measured by contacting the channel with an antibody or antigen-binding fragment described herein, measuring the activity of the channel, and comparing the measurement to a measurement of a control channel. In particular embodiments, activity of the channel is assessed by measuring calcium conductance of the channel. Standard techniques for measuring calcium conductance of an L-type voltage-gated calcium channel are known in the art and include, but are not limited to electrophysiological techniques such as patch clamp recording, single channel recording, and whole cell recording; calcium imaging techniques utilizing chemical indicators such as fura-2, indo-1, fluo-3, fluo-4, Calcium Green-1, or genetically encoded indicators such as Pericams, Cameleons, and GCaMP, and measurement of events correlated to L-type voltage-gated channel activity such as expression, phosphorylation, or translocation of a protein.

In some embodiments, contacting a cell expressing an L-type voltage-gated channel with an antibody or antigen binding fragment thereof of the current invention modulates activity of the cell. Modulating the activity of a cell refers to modulating at least one cellular process. Examples of a cellular process include, but are not limited to, cell survival, apoptosis, necrosis, programed cell death, transcription, translation, lipid synthesis, maturation, differentiation, catabolism, digestion, absorption, secretion, division, cell growth, migration, remodeling, repair, and storage. In some embodiments, the antibody or antigen-binding fragment thereof decreases activity of the cell. In some embodiments, the antibody or antigen-binding fragment thereof increases activity of the cell. In some embodiments, the antibody or antigen-binding fragment thereof both increases and decreases activity of the cell. Activity of a cell can be modulated, for example, by modulating the degree to which a cell performs the activity, or by increasing or decreasing the number of cells that perform the activity. Cellular activity can be both increased and decreased, for example, by an antibody that initially increases the activity of the then produces a sustained decrease in the cell, or for example, by increasing the activity in one population of cells and decreasing the activity in a different population of cells.

Some embodiments contemplate a model whereby L-type voltage-gated calcium channels regulate cellular activities and processes by regulating the intracellular concentration of calcium. Calcium ions are signaling molecules as the cytosolic concentration of calcium ions regulates a multitude of enzymes and proteins. Movement of calcium ions into the cytosol can influence cellular processes or activities by regulating the voltage gradient across membrane, for example, by contributing to the action potential of a cardiac cell, or by acting as a secondary messenger. Secondary messengers are molecules that relay and amplify signals, for example, from the cell surface, to target molecules in the cell, such as in the cytosol and/or nucleus. Calcium ions are usually maintained at a low concentration in the cytoplasm through active extracellular transport of calcium ions, or transport of calcium ions into intracellular stores such as the endoplasmic reticulum. A transient rise in the cytoplasmic calcium concentration allows calcium ions to bind to a large number of calcium-binding proteins that serve as molecular targets, for example, calmodulin, a $Ca^{2+}$-binding protein abundant in the cytosol of all cells. Calcium ions bind to and activate calmodulin, which then initiates its effects by binding to still other downstream targets, such as protein kinases. Calcium signaling can activate other secondary messenger systems, such as the phospholipase C/protein kinase C signaling cascade. This signaling in turn can coordinate and trigger cellular processes or activity, for example, transcription, translation, secretion or maturation.

Thus, some embodiments contemplate, but are not bound by, a model whereby L-type voltage-gated calcium channels regulate a cellular process or activity by regulating cytosolic calcium concentrations. In some embodiments, modulating the activity of an L-type calcium channel modulates an activity of the cell expressing the channel by regulating intracellular calcium signaling. Thus, in some embodiments, where an activity of the cell is positively regulated by calcium, enhancing, agonizing, activating, or increasing activity of an L-type calcium channel increases the activity of the cell by increasing the cytosolic concentration of calcium ions in the cell, and conversely, decreasing or inhibiting calcium channel activity decreases, or prevents an increase of, intracellular calcium concentrations and inhibits or decreases the activity of the cell. Conversely, if a cellular activity is negatively coupled to calcium signaling in a cell expressing an L-type voltage gated calcium channel, increasing channel activity will inhibit the cellular activity, and inhibiting the channel activity will increase the cellular activity. In some embodiments, modulating an L-type voltage-gated calcium channel of a cell modulates one or more cellular activities regulated by calcium in the cell, while not modulating one or more different cellular activities regulated by calcium in the cell.

In some embodiments, an antibody or antigen binding fragment thereof as described herein contacts a cell expressing an L-type voltage-gated calcium channel and thereby modulates an activity of the cell. In some embodiments, the antibody or antigen-binding fragment thereof inhibits the activity of the cell. In particular embodiments, inhibiting the activity of the cell reduces activity of the cell by a statistically significant amount. In particular embodiments, inhibiting the activity of the cell results in a decrease of cellular activity of 5%, 6%, 7%, 8%, 9%, 10%, 11%, 12%, 13%, 14%, 15%, 16%, 17%, 18%, 19%, 20%, 25%, 30%, 35%, 40%, 45%, 50%, 55%, 60%, 65%, 70%, 75%, 80%, 85%, 90%, 95%, or 100% (including all integers and ranges in between).

In some embodiments, the antibody or antigen-binding fragment increases the activity of the cell. In particular embodiments, increasing the activity of the cell increases the activity by a statistically significant amount. In particular embodiments, increasing the activity of a cell results in an increase of cellular activity of 5%, 6%, 7%, 8%, 9%, 10%, 11%, 12%, 13%, 14%, 15%, 16%, 17%, 18%, 19%, 20%, 25%, 30%, 35%, 40%, 45%, 50%, 55%, 60%, 65%, 70%, 75%, 80%, 85%, 90%, 95%, or 100% (including all integers and ranges in between). In certain embodiments, increasing in activity of a cell results in a 2-fold, 3-fold, 4-fold, 5-fold, 6-fold, 7-fold, 8-fold, 9-fold, 10-fold, 20-fold, 30-fold, 40-fold, 50-fold, 60-fold, 70-fold, 80-fold, 90-fold, 100-fold, 200-fold, 300-fold, 400-fold, 500-fold, 1,000-fold, 10,000-fold, or greater than 10,000-fold increase (including all integers and ranges in between) of channel activity.

In certain embodiments, modulation of an activity in a cell is quantified by standard techniques known in the art. In some embodiments, modulation of activity of an L-type voltage-gated calcium channel is measured by contacting the cell with an antibody or antigen-binding fragment thereof, measuring the activity of the cell, and comparing the measurement to a measurement of a control cell. In some embodiments, cell activity is measured in cultured cells, animal models, or samples or biopsy taken from a subject. Techniques to examine cellular activity are well known in the art, and include assays to examine cell survival, transcription, translation, lipid synthesis, differentiation, absorption, secretion, division, growth, migration, and remodeling. Appropriate functional assays can be readily determined by one skilled in the art taking into consideration the cell type involved and the activity to be measured.

In certain embodiments, antibodies and antigen-binding fragments thereof as described herein contact voltage-gated calcium channels that are expressed in immune cells, such as hematopoietic cells. Hematopoietic cells include cells from the myeloid lineage (including monocytes, macrophages, neutrophils, basophils, eosinophils, erythrocytes, megakaryocytes, platelets, mast cells and dendritic cells) and cells from the lymphoid lineage (including T cells, B cells, and natural killer (NK) cells). In some embodiments, the antibodies and antigen-binding fragments thereof decrease immune cell activity. In some embodiments, antibodies and antigen-binding fragments thereof increase immune cell activity. In some embodiments, antibodies and antigen-binding fragments thereof increase and decrease immune cell activity, for example, by initially increasing immune cell function and then decreasing immune cell function, or by increasing the activity of one population of immune cells and decreasing the activity of another population of immune cells.

Examples of immune cell activity include, but are not limited to, a cellular process of an immune cell, as well as cellular processes or activities that contribute to an innate or adaptive immune response. Activities contributing to adaptive immune response include activities performed by cells of lymphoid lineage, such as T cells and B cells. In T cells, these activities include, but are not limited to, inducing maturation of B cells in plasma cells and memory B cells, activation of cytotoxic T cells and macrophages, cytokine production and secretion by helper (CD4$^+$) T cells; lysing cells (such as virally infected cells or tumor cells) by cytotoxic (CD8$^+$) T cells; suppression of T cell mediated immunity by regulatory (suppressor) T cells; expansion by cell division in memory T cells. T cell activities also include T cell receptor binding to antigens and T cell maturation. In B cells, activities include antibody production and secretion by plasma cells, antigen binding to the B cell receptor, and B cell receptor activation. B cell activities also include maturation and survival. Examples of immune cell activity that contributes to innate immunity include release of histamine-containing granules and chemokines by mast cells, engulfment of cells, pathogens, or particles by phagocytes and macrophages; release of oxidizing agents, free oxygen radicals, and hypochlorite by neutrophils; release of histamine, toxic proteins, and free radicals by basophils and eosinophils; and destruction of infected cells by Natural Killer (NK) cells. Certain embodiments contemplate, but are not bound by, a model whereby these examples of immune cell function are considered positively coupled to calcium signaling.

Maturation generally refers to a process whereby a less specialized cell develops into a more specialized cell type. Maturation involves signal-regulated adjustments in cells, immune cells, and/or thymocytic cells that lead to cellular specialization. Examples of maturation in the immune system include, but are not limited to, monocyte maturation to macrophage; B thymocyte maturation to B lymphocyte, and further maturing to a plasma cell or memory B cell; and T thymocyte maturation to T lymphocyte, and further maturation to cytotoxic T lymphocyte, cytokine induced killer T cell, helper T cell, regulatory T cell, or a natural killer T cell.

In some embodiments, an antibody or antigen binding fragment thereof as described herein contacts an immune cell expressing an L-type voltage gated calcium channel and thereby modulates an activity of the immune cell. In some embodiments, the antibody or antigen-binding fragment inhibits the activity of the immune cell. In particular embodiments, inhibiting the activity of the immune cell reduce activity by a statistically significant amount. In particular embodiments, inhibiting the activity of the cell results in a decrease of cellular activity of 5%, 6%, 7%, 8%, 9%, 10%, 11%, 12%, 13%, 14%, 15%, 16%, 17%, 18%, 19%, 20%, 25%, 30%, 35%, 40%, 45%, 50%, 55%, 60%, 65%, 70%, 75%, 80%, 85%, 90%, 95%, or 100% (including all integers and ranges in between).

In some embodiments, the antibody or antigen-binding fragment increases the activity of the immune cell. In particular embodiments, increasing the activity of the immune cell increase the activity by a statistically significant amount. In particular embodiments, increasing the immune cell activity results in an increase of immune cell activity of 5%, 6%, 7%, 8%, 9%, 10%, 11%, 12%, 13%, 14%, 15%, 16%, 17%, 18%, 19%, 20%, 25%, 30%, 35%, 40%, 45%, 50%, 55%, 60%, 65%, 70%, 75%, 80%, 85%, 90%, 95%, or 100% (including all integers and ranges in between). In certain embodiments, increasing the activity of an immune cell results in a 2-fold, 3-fold, 4-fold, 5-fold, 6-fold, 7-fold, 8-fold, 9-fold, 10-fold, 20-fold, 30-fold, 40-fold, 50-fold, 60-fold, 70-fold, 80-fold, 90-fold, 100-fold, 200-fold, 300-fold, 400-fold, 500-fold, 1,000-fold, 10,000-fold, or greater than 10,000-fold increase (including all integers and ranges in between) of channel activity.

Appropriate functional assays can be readily determined by one skilled in the art taking into consideration the cell type involved. For example, cell survival, cell proliferation, cell differentiation and/or cell activation of an immune cell could be assessed by standard techniques. For example, changes in gene expression associated with particular processes can be measured with known techniques in the art, for example, fluorescence in situ hybridization, immunohistochemistry, qPCR, and western blot analysis. Alternatively, measurements of processes such cytokine secretion or cytolytic ability can be directly assessed using techniques known in the art. Suitable assays to assess immune function of various hematopoietic cells are known in the art.

Some embodiments relate to methods of contacting immune cells with antibodies or antigen-binding fragments described herein to modify activity of an immune cell for the purposes of treating a subject in need thereof. In some aspects, the subject is in need of treatment for a disease. In particular embodiments, immune cells are contacted in vitro for the purposes of treating a subject, for example, through adoptive cell transfer. Adoptive cell transfer, as used herein, refers to the transfer immune-derived cells, back into the same patient or into a new recipient host with the goal of transferring the immunologic functionality and characteristics into the new host. If possible, use of autologous cells helps the recipient by minimizing graft versus host disease issues. In certain embodiments, an antibody or antigen-binding fragment thereof described herein is administered to the subject.

As used herein, the term "immune response" includes T cell mediated and/or B cell mediated immune responses. Exemplary immune responses include T cell responses, e.g., cytokine production and cellular cytotoxicity. In addition, the term immune response includes immune responses that are indirectly affected by T cell activation, e.g., antibody production (humoral responses) and activation of cytokine responsive cells, e.g., macrophages. Immune cells involved in the immune response include lymphocytes, such as B cells and T cells (CD4+, CD8+, Th1 and Th2 cells); antigen presenting cells (e.g., professional antigen presenting cells such as dendritic cells, macrophages, B lymphocytes, Langerhans cells, and nonprofessional antigen presenting cells such as keratinocytes, endothelial cells, astrocytes, fibroblasts, oligodendrocytes); natural killer cells; myeloid cells, such as macrophages, eosinophils, mast cells, basophils, and granulocytes. In some embodiments, the antibodies or antigen-binding fragments described herein are effective to reduce inflammatory cell trafficking to the site of inflammation. In some embodiments, the term "immune response" encompasses activation of pattern recognition receptors (PRRs) and release of inflammatory mediators on macrophages, dendritic cells, histiocytes, Kupffer cells and/or mastocytes. Examples of inflammatory mediators include lysosome granules, histamine, IFN-gamma, IL-8, Leukotriene B4, nitric oxide, prostaglandins, and TNF-alpha.

In particular embodiments, antibodies and antigen-binding fragments described herein that decrease L-type voltage channel activity are used as immunosuppressants, which find application, for example, in the treatment of autoimmune diseases, in reducing the risk of transplant rejection, and/or in the treatment of other disorders requiring suppression of the immune system, such as treatment of allergy. In some embodiments, antibodies or antigen-binding fragments thereof that inhibit L-type voltage-gated calcium channels expressed in T cells or B cells are useful, for example, as immunosuppressants. In another example, antibodies or antigen-binding fragments thereof that inhibit L-type voltage-gated calcium channels in mast cells are useful, for example, to reduce mast cell activity and treat allergy.

Examples of autoimmune diseases that may be treated in accordance with certain embodiments of the invention include, but are not limited to, X-linked agammaglobulinemia, systemic lupus erythematosus, inflammatory (rheumatoid) arthritis, Hashimoto's thyroiditis, pernicious anemia, inflammatory bowel disease (Crohn's disease and ulcerative colitis), psoriasis, renal fibroses, pulmonary fibroses, hepatic fibroses, Addison's disease, Type I diabetes, systemic lupus erythematosus (SLE), dermatomyositis, Sjogren's syndrome, multiple sclerosis, myasthenia gravis, Reiter's syndrome, and Grave's disease. Clinical indicators of response can be measured for each of these diseases. For example, a reduction in pain, reduction in inflammation of tissues (for example, joints), improved tissue (for example, kidney) function, or improved ability to digest food can serve as indicators of successful immunosuppression.

Certain embodiments contemplate the administration of a therapeutic agent targeted to a voltage-gated calcium channel expressed in hematopoietic cells in conjunction with an anti-inflammatory agent or immunosuppressive agent. Certain embodiments contemplate the administration of an antibody or antigen-binding fragment described herein in conjunction with a known anti-inflammatory agent or immunosuppressive agent. Certain embodiments contemplate the administration of an antibody or antigen-binding fragment described herein in conjunction with an anti-inflammatory agent or immunosuppressive agent. Examples of immunosuppressive agents include non-steroidal anti-inflammatory agents (such as diclofenac, diflunisal, etodolac, flurbiprofen, ibuprofen, indomethacin, ketoprofen, ketorolac, nabumetone, naproxen, oxaprozin, piroxicam, sulindac, tolmetin, celecoxib, or rofecoxib), steroids (such as cortisone, dexamethasone, hydrocortisone, methylprednisolone, prednisolone, prednisone, or triamcinolone) and immunosuppressive agents (such as cyclosporin, tacrolimus, mycophenolic acid, or sirolimus). Other examples include biological response modifiers (such as Kineret® (anakinra), Enbrel® (etanercept), or Remicade® (infliximab)), disease-modifying anti-rheumatic drugs (DMARD) (such as Arava® (leflunomide)), Hyalgan® (hyaluronan) and Synvisc® (hylan G-F20).

In particular embodiments, antibodies and antigen-binding fragments described herein that increase activity of an L-type voltage-gated calcium channel that is expressed on an immune cell. These antibodies are used, for example, to increase or generate an immune response. Such agents and methods may be useful in the treatment of cancer and/or treatment of immune suppression.

Certain embodiments therefore relate to the treatment of cancer in a subject in need thereof, comprising administering to the subject an antibody or antigen-binding fragment thereof, as described herein. In some embodiments, the subject is not significantly immunosuppressed or immunodeficient. Examples of cancers include breast cancer, cervical cancer, prostate cancer, gastrointestinal cancer, lung cancer, ovarian cancer, testicular cancer, head and neck cancer, bladder cancer, kidney cancer (e.g., renal cell carcinoma), soft tissue sarcoma, squamous cell carcinoma, CNS or brain cancer, melanoma, non-melanoma cancer, thyroid cancer, endometrial cancer, an epithelial tumor, bone cancer, and hematopoietic cancer. In certain embodiments, the lung cancer is osteosarcoma, chondrosarcoma, or a Ewing Sarcoma Family of Tumors (ESFTs). In certain embodiments, the gastrointestinal cancer is esophageal cancer, stomach (gastric) cancer, pancreatic cancer, liver cancer, gallbladder (biliary) cancer, small intestinal cancer, colorectal cancer, anal or rectal cancer, or gastrointestinal carcinoid or stromal tumor. In certain embodiments, the melanoma is lentigo maligna, lentigo maligna melanoma, superficial spreading melanoma, acral lentiginous melanoma, mucosal melanoma, nodular melanoma, polypoid melanoma, desmoplastic melanoma, amelanotic melanoma, soft-tissue melanoma, or uveal melanoma. In certain embodiments, the hematopoietic cancer is a lymphoma, leukemia, or multiple myeloma. In certain embodiments, the lymphoma is a T-cell lymphoma, B-cell lymphoma, small lymphocytic lymphoma, mangle cell lymphoma, anaplastic large cell lymphoma (ALCL), follicular lymphoma, Hodgkin's lymphoma, or non-Hodgkin's lymphoma. In certain embodiments, the leukemia is chronic lymphocytic leukemia (CLL), hairy cell leukemia, acute lymphoblastic leukemia, myelocytic leukemia, acute myeloid or myelogenous leukemia, or chronic myelogenous leukemia. In certain embodiments, the brain cancer is a glioma, meningioma, pituitary adenoma, vestibular schwannoma, primary CNS lymphoma, neuroblastoma, primitive neuroectodermal tumor (medulloblastoma), or glioblastoma multiforme.

Certain methods include the treatment of cancers that express (e.g., over-express) one or more Cav1 channels. For instance, in certain embodiments, the cancer expresses (e.g., over-expresses), Cav1.1, Cav1.2, Cav1.3, Cav1.4, or any combination thereof. In some embodiments, the cancer expresses (e.g., over-expresses) Cav1.1 and the therapeutic antibody or antigen-binding fragment thereof binds (e.g., selectively binds) to Cav1.1. In some embodiments, the cancer expresses (e.g., over-expresses) Cav1.2 and the therapeutic antibody or antigen-binding fragment thereof binds (e.g., selectively binds) to Cav1.2. In some embodiments, the cancer expresses (e.g., over-expresses) Cav1.3 and the therapeutic antibody or antigen-binding fragment thereof binds (e.g., selectively binds) to Cav1.3. In some embodiments, the cancer expresses (e.g., over-expresses) Cav1.4 and the therapeutic antibody or antigen-binding fragment thereof binds (e.g., selectively binds) to Cav1.4.

FIG. 10 illustrates the association between Cav channel expression and certain cancer types. Thus, certain embodiments relate to the treatment of any one or more of the cancers in FIG. 10, which optionally express (e.g., over-express) one or more Cav1 channels. In some embodiments, the antibody or antigen-binding fragment thereof binds to Cav1.1 and is used in the treatment of a skeletal muscle cancer, larynx cancer, thyroid cancer, prostate cancer, leukemia, solid tumor, Burkett lymphoma, meduloblastoma, endometrial cancer, or lung carcinoma that expresses (e.g., over-expresses) Cav1.1 (see, e.g., FIG. 10). In some embodiments, the antibody or antigen-binding fragment thereof binds to Cav1.2 and is used in the treatment of a cancer of the spleen, cancer of the thymus, uterine cancer, brain cancer, colon cancer, chondrosarcoma, lymphoma, leukemia, neuroblastoma, or Hodgkin's lymphoma that expresses (e.g., over-expresses) Cav1.2 (see, e.g., FIG. 10). In some embodiments, the antibody or antigen-binding fragment thereof binds to Cav1.3 and is used in the treatment of a cancer of the bone, brain, lung, intestine, pituitary gland, pancreas, adrenal gland, kidney, testis, bronchial epithelium, or breast (e.g., breast carcinoma) that expresses (e.g., over-expresses) Cav1.3 (see, e.g., FIG. 10). In some embodiments, the antibody or antigen-binding fragment thereof binds to Cav1.4 and is used in the treatment of a cancer of the lung, muscle, thymus, pineal gland, small intestine, spleen that expresses (e.g., over-expresses) Cav1.4, or in the treatment of leukemia, lymphoma, or meningioma that expresses (e.g., over-expresses) Cav1.4 (see, e.g., FIG. 10).

Some methods include administering an antibody in combination with an additional cancer therapy. In certain embodiments, the additional cancer therapy selected from one or more of an anti-cancer agent, radiotherapy, surgery, transplantation, photodynamic therapy, symptomatic care, and antibiotic therapy. In certain embodiments, the additional anti-cancer agent is selected from a small molecule and an antibody. In certain embodiments, the small molecule is a cytotoxic, chemotherapeutic, or anti-angiogenic agent. In certain embodiments, the small molecule cytotoxic, chemotherapeutic, or anti-angiogenic agent is selected from one or more of alkylating agents, anti-metabolites, anthracyclines, anti-tumor antibiotics, platinums, type I topoisomerase inhibitors, type II topoisomerase inhibitors, *vinca* alkaloids, and taxanes.

In certain embodiments, the additional small molecule is selected from one or more of chlorambucil, cyclophosphamide, cilengitide, lomustine (CCNU), melphalan, procarbazine, thiotepa, carmustine (BCNU), enzastaurin, busulfan, daunorubicin, doxorubicin, gefitinib, erlotinib idarubicin, temozolomide, epirubicin, mitoxantrone, bleomycin, cisplatin, carboplatin, oxaliplatin, camptothecins, irinotecan, topotecan, amsacrine, etoposide, etoposide phosphate, teniposide, temsirolimus, everolimus, vincristine, vinblastine, vinorelbine, vindesine, CT52923, paclitaxel, imatinib, dasatinib, sorafenib, pazopanib, sunitnib, vatalanib, geftinib, erlotinib, AEE-788, dichloroacetate, tamoxifen, fasudil, SB-681323, semaxanib, donepizil, galantamine, memantine, rivastigmine, tacrine, rasigiline, naltrexone, lubiprostone, safinamide, istradefylline, pimavanserin, pitolisant, isradipine, pridopidine (ACR16), tetrabenazine, bexarotene, glatirimer acetate, fingolimod, and mitoxantrone, including pharmaceutically acceptable salts and acids thereof.

In certain embodiments, the additional antibody is selected from one or more of 3F8, 8H9, abagovomab, adecatumumab, afutuzumab, alacizumab (pegol), alemtuzumab, altumomab pentetate, amatuximab, anatumomab mafenotox, apolizumab, arcitumomab, bavituximab, bectumomab, belimumab, bevacizumab, bivatuzumab (mertansine), brentuximab vedotin, cantuzumab (mertansine), cantuzumab (ravtansine), capromab (pendetide), carlumab, catumaxomab, cetuximab, citatuzumab (bogatox), cixutumumab, clivatuzumab (tetraxetan), conatumumab, dacetuzumab, daclizumab, dalotuzumab, detumomab, drozitumab, ecromeximab, edrecolomab, elotuzumab, enavatuzumab, ensituximab, epratuzumab, ertumaxomab, etaracizumab, farletuzumab, FBTA05, figitumumab, flanvotumab, galiximab, gemtuzumab, ganitumab, gemtuzumab (ozogamicin), girentuximab, glembatumumab (vedotin), ibritumomab tiuxetan, icrucumab, igovomab, indatuximab ravtansine, intetumumab, inotuzumab ozogamicin, ipilimumab (MDX-101), iratumumab, labetuzumab, lexatumumab, lintuzumab, lorvotuzumab (mertansine), lucatumumab, lumiliximab, mapatumumab, matuzumab, milatuzumab, mitumomab, mogamulizumab, moxetumomab (pasudotox), nacolomab (tafenatox), naptumomab (estafenatox), narnatumab, necitumumab, nimotuzumab, nivolumab, Neuradiab® (with or without radioactive iodine), NR-LU-10, ofatumumab, olaratumab, onartuzumab, oportuzumab (monatox), oregovomab, panitumumab, patritumab, pemtumomab, pertuzumab, pritumumab, racotumomab, radretumab, ramucirumab, rilotumumab, rituximab, robatumumab, samalizumab, sibrotuzumab, siltuximab, tabalumab, tanezumab, taplitumomab (paptox), tenatumomab, teprotumumab, TGN1412, ticilimumab, trastuzumab, tremelimumab, tigatuzumab, TNX-650, tositumomab, TRBS07, tucotuzumab (celmoleukin), ublituximab, urelumab, veltuzumab, volociximab, votumumab, and zalutumumab, including antigen-binding fragments thereof.

Also included are compositions for use in treating cancer, comprising a pharmaceutically acceptable carrier and an antibody or antigen-binding fragment thereof, as described herein. Some embodiments include compositions (e.g., pharmaceutical compositions), comprising a pharmaceutically acceptable carrier, an anti-cancer agent, and an antibody or antigen-binding fragment thereof, as described herein.

Certain embodiments of the invention provide for the use of the antibodies and antigen-binding fragments thereof described herein to increase an immune response in an immunocompromised subject, for example, to treat or prevent an opportunistic infection in an immunocompromised subject. Immunocompromised subjects are more susceptible to opportunistic infections, for example, viral, fungal, protozoan, or bacterial infections, prion diseases, and certain neoplasms. Those who can be considered to be immunocompromised include, but are not limited to, subjects with AIDS (or HIV positive), subjects with severe combined immune deficiency (SCID), diabetics, subjects who have had transplants and who are taking immunosuppressive agents/therapies, and those who are receiving chemotherapy for cancer. Immunocompromised individuals also include subjects with most forms of cancer (other than skin cancer), sickle cell anemia, cystic fibrosis, those who do not have a spleen, subjects with end stage kidney disease (dialysis), and those who have been taking corticosteroids on a frequent basis by pill or injection within the last year. Subjects with severe liver, lung, or heart disease also can be immunocompromised.

Formulations and Administration

The antibodies and antigen-binding fragments thereof as described herein may be administered in any manner which is medically acceptable. This may include injections, by parenteral routes such as intravenous, intravascular, intraarterial, subcutaneous, intramuscular, intratumor, intraperitoneal, intraventricular, intraepidural, or others as well as oral, nasal, ophthalmic, rectal, or topical. Sustained release administration is also specifically included in the invention, by such means as depot injections or erodible implants. Localized delivery is particularly contemplated, by such means as delivery via a catheter to one or more arteries, such as the renal artery or a vessel supplying a localized tumor.

The subject antibodies may be formulated with a pharmaceutically acceptable carrier. The term "pharmaceutically acceptable carrier" means one or more organic or inorganic ingredients, natural or synthetic, with which the antibody is combined to facilitate its application. A suitable carrier includes sterile saline although other aqueous and non-aqueous isotonic sterile solutions and sterile suspensions known to be pharmaceutically acceptable are known to those of ordinary skill in the art.

Solutions or suspensions may include, for example, a sterile diluent (such as water), saline solution (e.g., phosphate buffered saline (PBS), physiological saline, Ringer's solution, isotonic sodium chloride), fixed oil, polyethylene glycol, glycerin, propylene glycol or other synthetic solvent; antimicrobial agents (such as benzyl alcohol and methyl parabens); antioxidants (such as ascorbic acid and sodium bisulfite), chelating agents (such as ethylenediaminetetraacetic acid (EDTA)); and/or buffers (such as acetates, citrates, phosphates, and other organic acids), including combinations of the foregoing. Also included as suitable carriers are solutions containing thickening and solubilizing agents, such as glucose, polyethylene glycol, polypropylene glycol and mixtures thereof. A surfactant may be added to facilitate the formation of a homogeneous solution or suspension. Surfactants are compounds that non-covalently interact with the antibody, or antigen-binding fragment thereof, so as to facilitate dissolution or homogeneous suspension of the conjugate in the aqueous system.

Additional examples of carriers include low molecular weight (e.g., less than about 10 residues) polypeptides or peptides; proteins such as serum albumin, gelatin, or immunoglobulins; hydrophilic polymers such as polyvinylpyrrolidone; amino acids such as glycine, glutamine, asparagine, arginine, or lysine; monosaccharides, disaccharides, and other carbohydrates including glucose, mannose, or dextrins; sugar alcohols such as mannitol or sorbitol; salt-forming counterions such as sodium; and/or nonionic surfactants such as polysorbate 20 (TWEEN™) polyethylene glycol (PEG), and poloxamers (PLURONICS™), and the like.

In some embodiments, the antibody, or antigen-binding fragment thereof, is entrapped in microcapsules prepared, for example, by coacervation techniques or by interfacial polymerization (for example, hydroxymethylcellulose or gelatin-microcapsules and poly-(methylmethacylate) microcapsules, respectively), in colloidal drug delivery systems (for example, liposomes, albumin microspheres, microemulsions, nano-particles and nanocapsules), or in macroemulsions. Such techniques are disclosed in Remington's Pharmaceutical Sciences, 16th edition, Oslo, A., Ed., (1980). The particle(s) or liposomes may further comprise other diagnostic agents, such as detectable entities.

In particular embodiments, the antibody, or antigen-binding fragment thereof, is a freeze-dried or lyophilized, cryodesiccated. These terms refer to a dehydration process of freezing the antibody composition and then reducing the surrounding pressure to allow the frozen water in the composition to sublimate directly from the solid phase to the gas phase. Also included are solid compositions such as powders, granules, compressed tablets, pills, capsules, and the like. In some iembodiments, solid composition contain one or more inert diluents or edible carriers. In certain embodiments, one or more of the following may be present: binders such as carboxymethylcellulose, ethyl cellulose, microcrystalline cellulose, gum tragacanth or gelatin; and excipients such as starch, lactose or dextrins, disintegrating agents such as alginic acid, sodium alginate, Primogel, corn starch and the like.

Certain embodiments include kits, comprising one or more of the antibodies, or antigen-binding fragments thereof, as described herein, optionally in one or more containers. The kits can include written instructions on how to use and/or prepare the antibodies for use, for example, as a medicament. In some embodiments, the written instructions describe how to use the antibodies, or antigen-binding fragments thereof, to administer antibodies or antigen-binding fragments thereof to a subject in need thereof.

An "effective amount" refers to that amount which is capable of ameliorating or delaying progression of the diseased, degenerative or damaged condition. An effective amount can be determined on an individual basis and will be based, in part, on consideration of the symptoms to be treated and results sought. An effective amount can be determined by one of ordinary skill in the art employing such factors and using no more than routine experimentation.

The kits herein may also include a one or more additional therapeutic agents or other components suitable or desired for the indication being treated, or for the desired diagnostic application. An additional therapeutic agent may be contained in a second container, if desired.

The following Examples are offered by way of illustration and not by way of limitation.

EXAMPLES

Example 1

Design and Generation of Antibodies Directed Against L-Type Voltage Gated Calcium Channels Antibodies were designed to the target L-type voltage-gated calcium channel subtypes Cav1.1, Cav1.2, Cav1.3, or Cav1.4. For each channel, an amino acid sequence was selected to use as targets for use as an antigen for generating mouse monoclonal antibodies. Amino acid sequences were selected to meet several criteria. First, the amino acid sequences had to be unique to their respective channels. Second, the amino acid sequences had to reside on an exposed portion of the channel positioned outside of the cell. Third, the amino acid sequence had to be found in both the mouse and human channel. Fourth, the sequence needed to be in a region of the channel that would affect the channel's activity when bound by an antibody.

For each of the L-type voltage-gated calcium channel subtype, an amino acid sequence located in the extracellular domain of the pore loop between transmembrane segments S5 and S6 of motif I of the alpha 1 subunit was selected (see FIG. 1). The amino acid sequences are displayed in table E1. Each sequence that was selected is unique to the channel subtype, positioned in an extracellular region of the channel, and conserved in mouse and human. Further, the extracellular domain of the pore loop between transmembrane segments S5 and S6 contributes to channel selectivity.

TABLE E1

Target Amino Acid Sequences

| Description | Sequence | SEQ ID NO: |
|---|---|---|
| Cav1.4 | GPGRPGDAPHTG | 1 |
| Cav1.3 | LTKETEGGNHSSGKSG | 2 |
| Cav1.2 | ATKADGANALGGKGA | 3 |
| Cav1.1 | PMQIELRHREWVH | 4 |

Monoclonal antibodies were generated using standard methods known in the art. Briefly, each peptide from table E1 was used to immunize 2 mice. After an immune response was detected, spleens of immunized mice were harvested, and lymphocytes were then isolated and fused with myeloma cells to generate hybridomas. Hybridomas were subcultured and cryopreserved (FIG. 2).

Example 2

Figure 9:
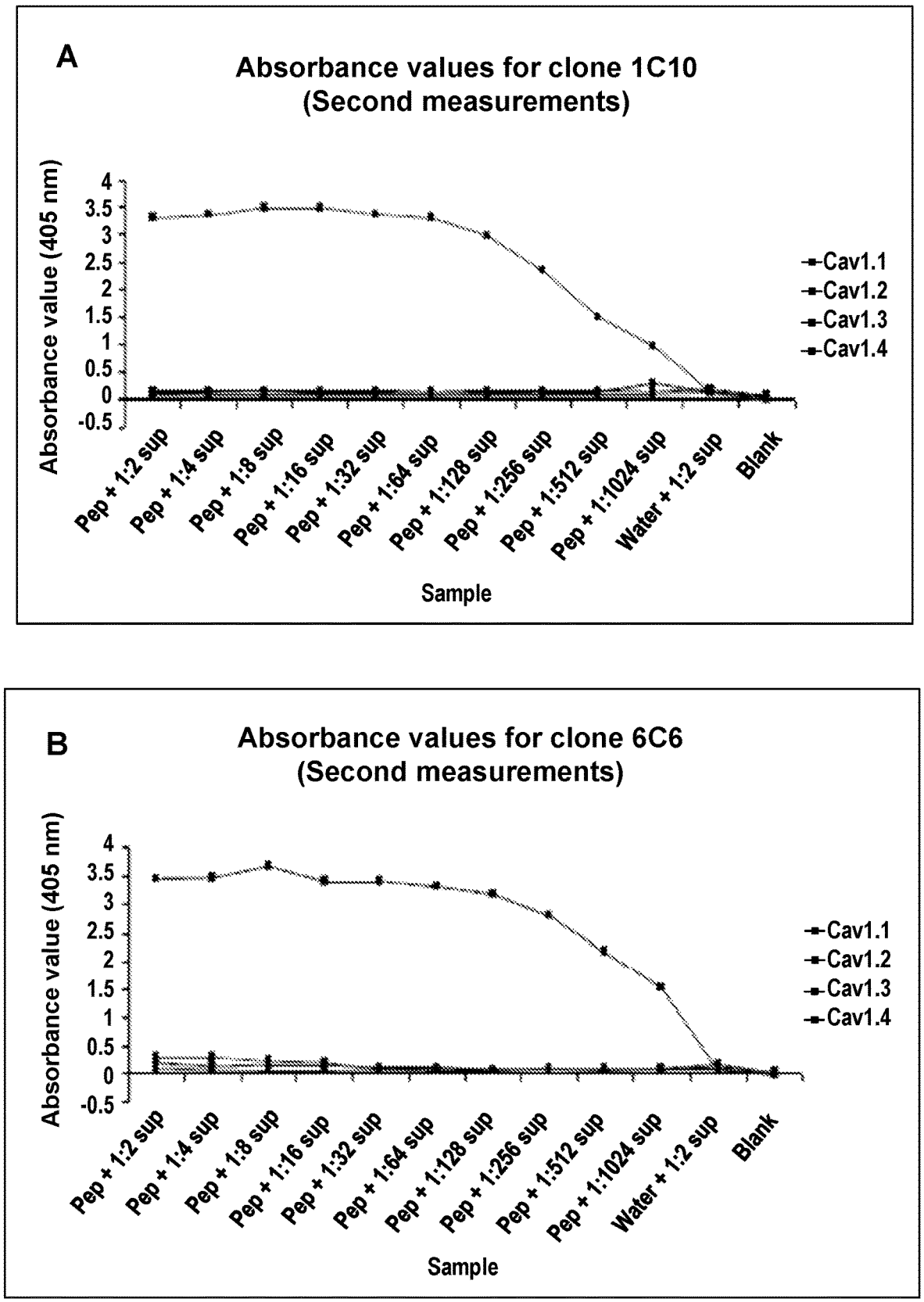
FIG. 9 shows representative results of selective binding data for hybridomas. Clone 1C10 (9A) selectively binds to Cav1.4, and clone 6C6 (9B) selectively binds to Cav1.2. Also shown are the binding data for clone 1C8 (9C), clone 6A3 (9D) which selectively binds to Cav1.2, clone 1D2 (9F) which selectively binds to Cav1.2, clone 1E7 (9F) which selectively binds to Cav1.2, clone 1F4 (9G) which selectively binds to Cav1.1, clone 2D5 (9H) which selectively binds to Cav1.4, clone 5F4 (9I), clone 5G10 (9J), clone 6E1 (9K), clone 6H7 (9L), clone 8G1 (9M), clone 9C3 (9N), and clone 10E11 (9O).
Figure 9:
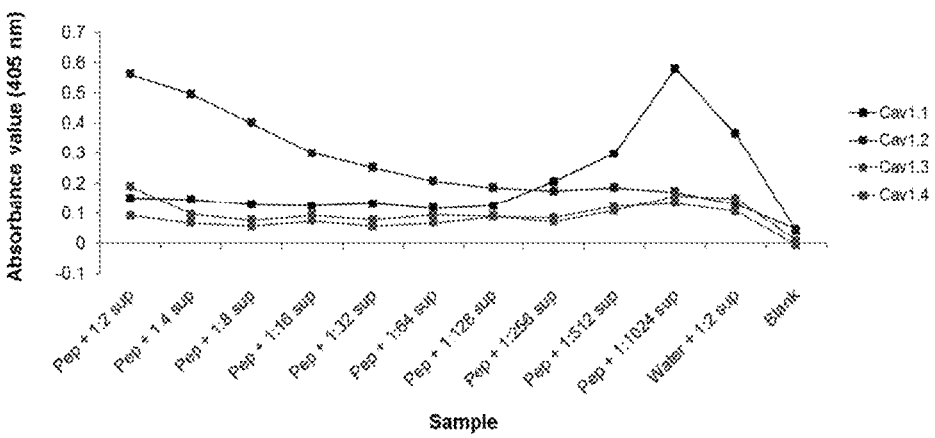
Figure 9:
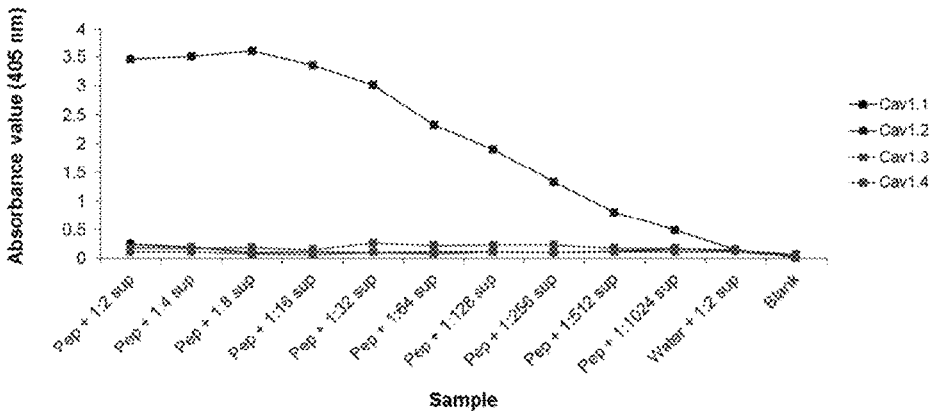
Figure 9:
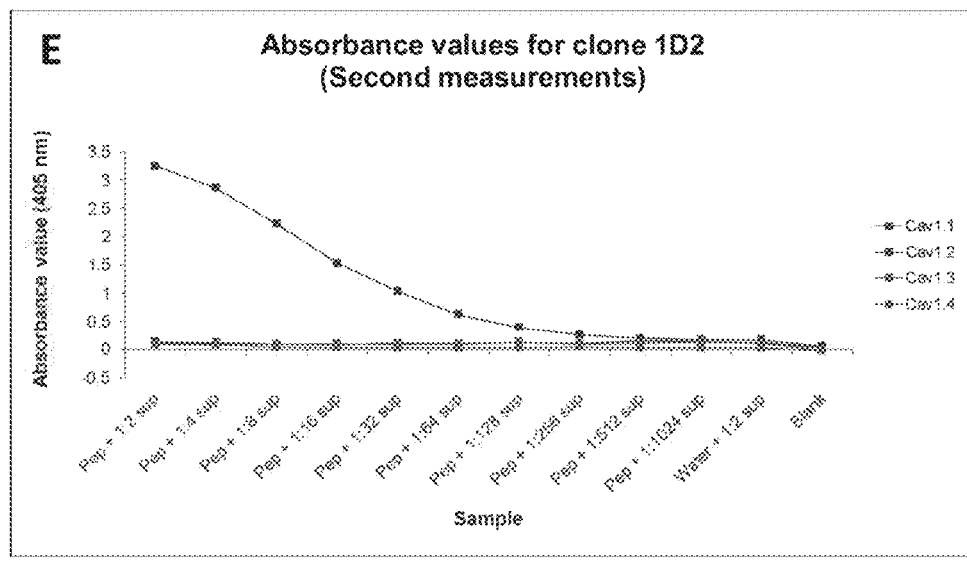
Figure 9:
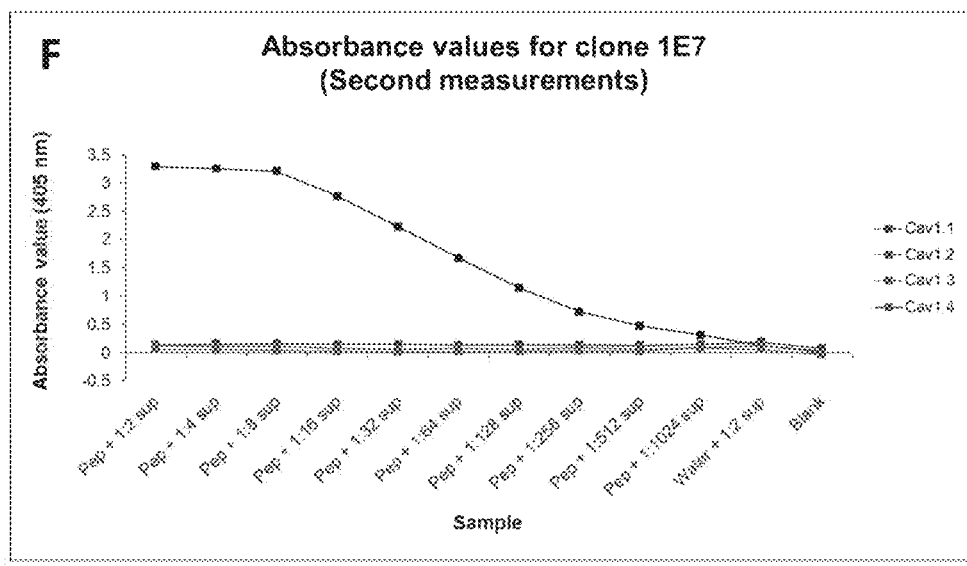
Figure 9:
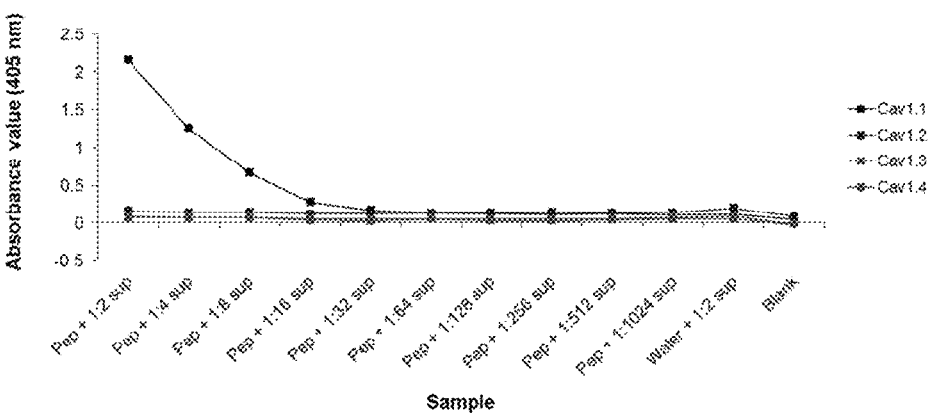
Figure 9:
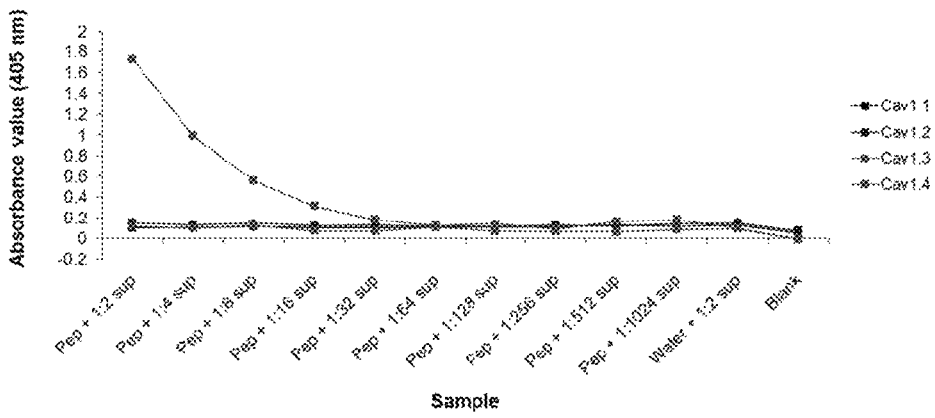
Figure 9:
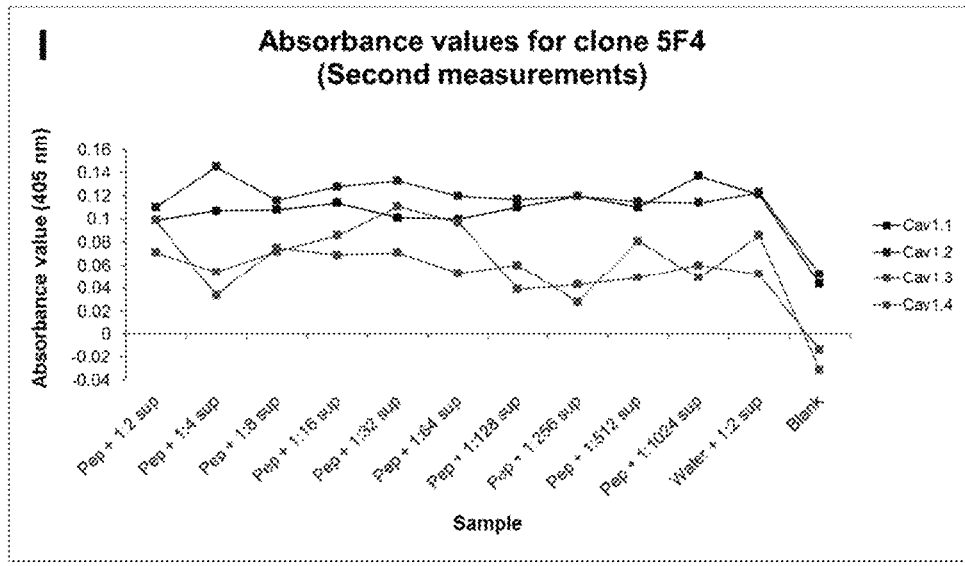
Figure 9:
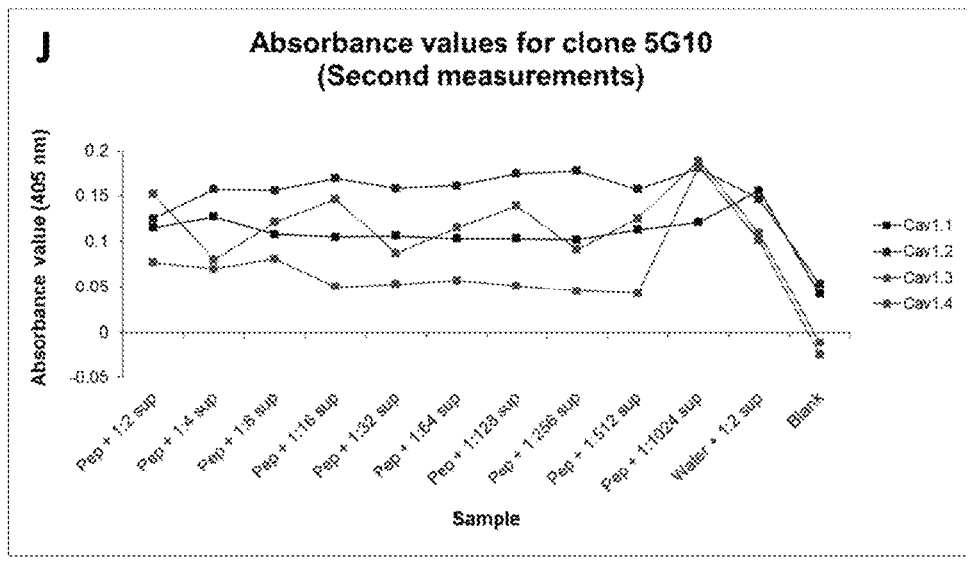
Figure 9:
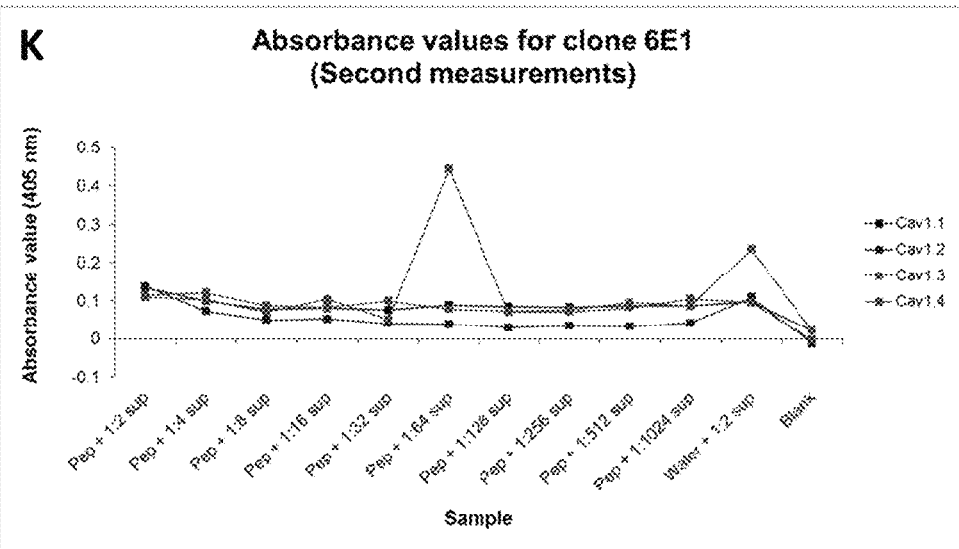
Figure 9:
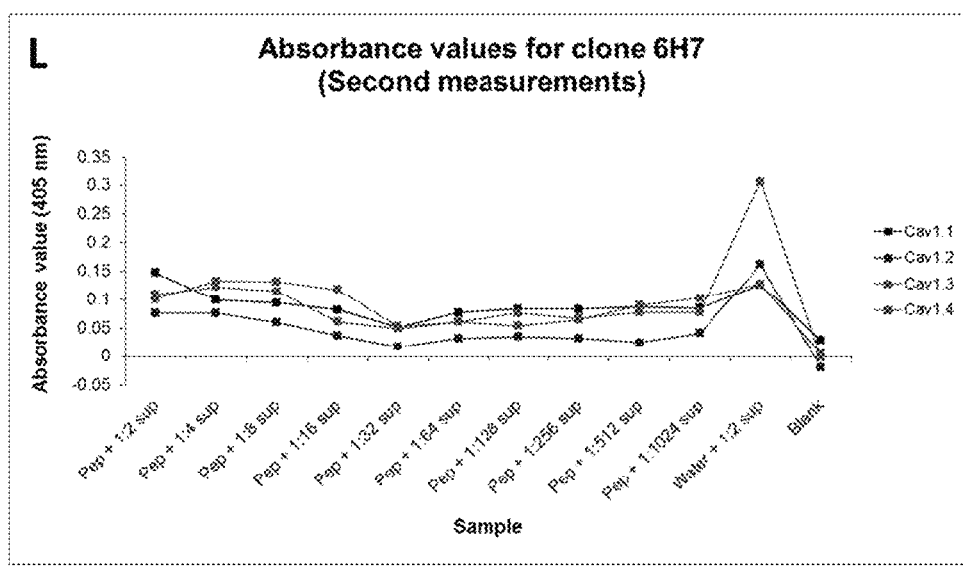
Figure 9:
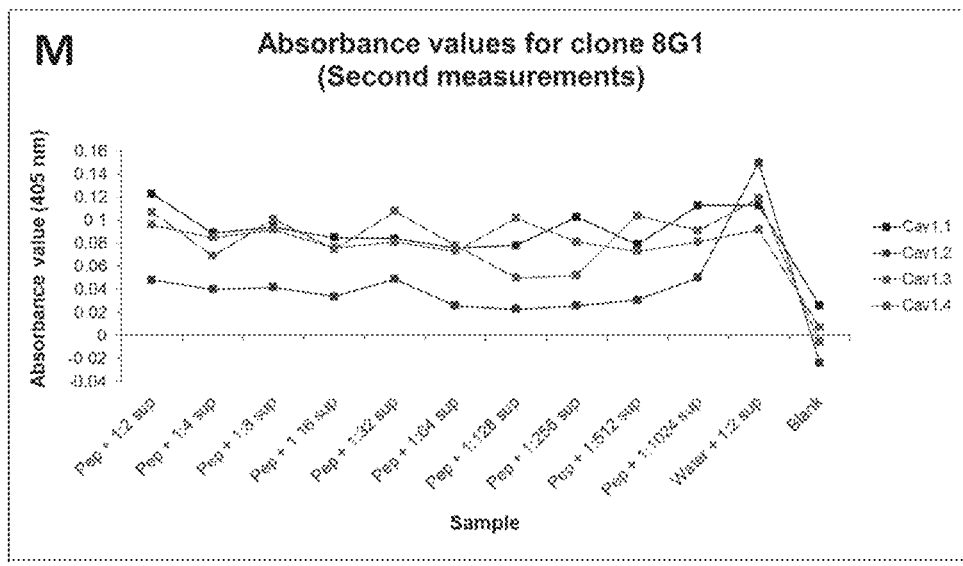
Figure 9:
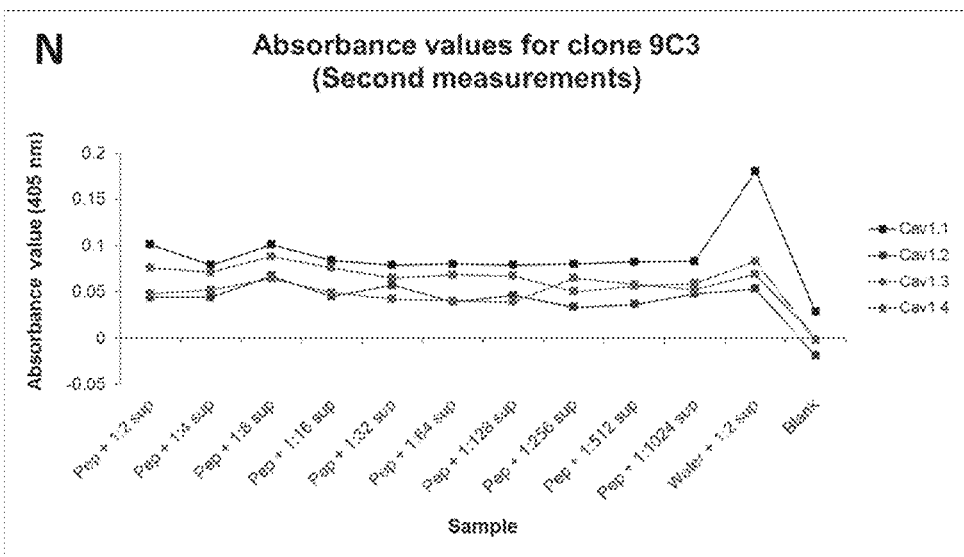
Figure 9:
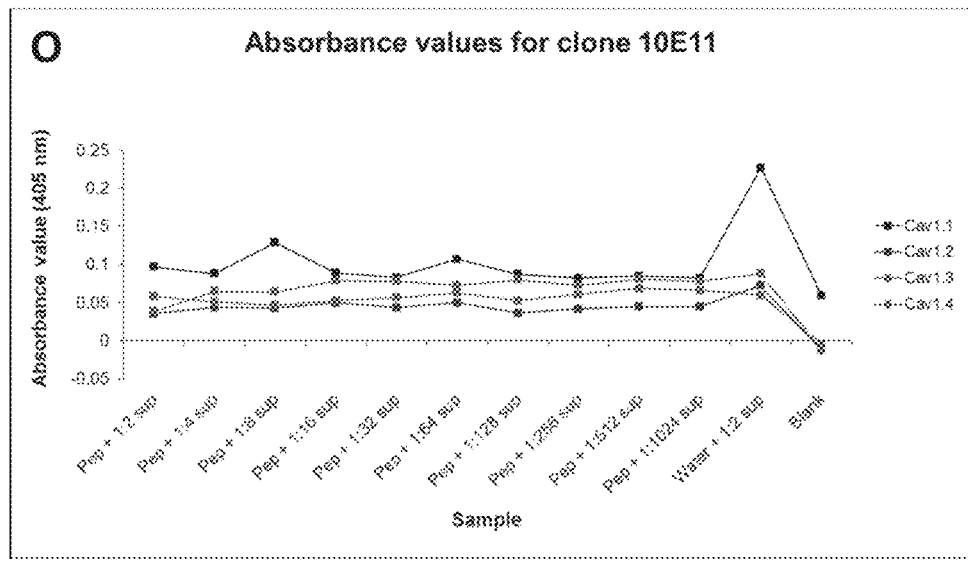

Characterization of Hybridoma Antibody Directed Against L-Type Voltage Gated Calcium Channels ELISA experiments were preformed to characterize monoclonal antibodies generated to target the extracellular pore domain of the L-type voltage-gated calcium channels. Sixty-three antibodies of interest were tested for their abilities to bind to the peptides with amino acid sequences from Table E1 that were used to generate the antibodies. Antibody binding was tested in wells coated with BSA and all the peptides with from each L-type voltage gated calcium channel, BSA and the Cav1.1 peptide, BSA and the Cav1.2 peptide, BSA and the Cav1.3 peptide, and BSA and the Cava.4 peptide. Binding was detected with a mixture of IgG and IgM secondary antibodies, and signal was compared to negative controls. Representative results of these experiments are presented (FIG. 3). The results indicated that the antibodies could specifically bind to the target peptides. Clones were observed that bound only to Cav1.1 (for example, see clones 1E7 and 1F4; FIG. 3), only to Cav1.2 (clones 1F7 and 6C6; FIGS. 3 and 9), only to Cav1.3 (clones 1B10, 1B11, and 2D4; FIG. 3), and only to Cav1.4 (clones 1C10 and 2B3, FIG. 3). In addition, some antibodies were observed that could bind to two Cav1 channels (for example, clones 1A3, 1B9, and 1C8) or three Cav1 channels (1D2). These results demonstrate that monoclonal antibodies that recognize extracellular pore loops of L-type voltage gated-calcium channels were successfully generated.

To determine if the antibodies could bind to L-type voltage gated calcium channels expressed on immune cells, flow cytometry experiments were performed to test the binding of the monoclonal antibodies to immune cells. Splenocytes and thymocytes were isolated from spleens and thymi that were harvested from wild-type C57BI6 mice. Cells were prepared for flow cytometry. Supernatants containing antibody were collected from hybridoma cultures to test the ability of the monoclonal antibodies to bind to the cells. FITC conjugated Goat anti-mouse IgG andante mouse IgM was used for secondary antibody to detect monoclonal binding.

Figure 4:
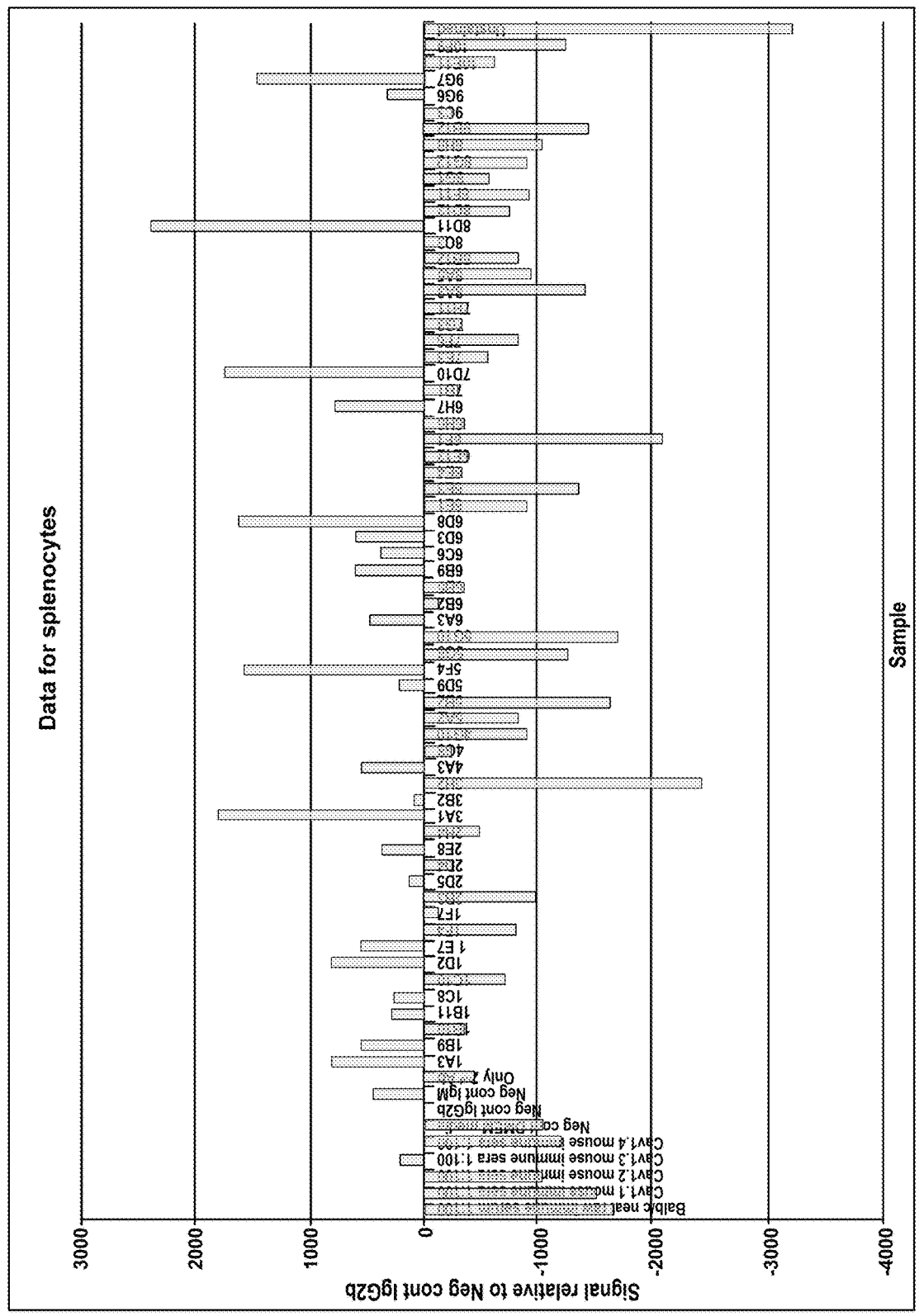
FIG. 4 shows representative results of flow cytometry experiments performed on antibodies produced by hybridoma clones. Supernatants containing monoclonal antibodies produced by hybridomas were tested to determine binding to wild-type mouse splenocytes. The binding signals of the monoclonal antibodies relative to IgG2b control antibody are displayed.
Figure 5:
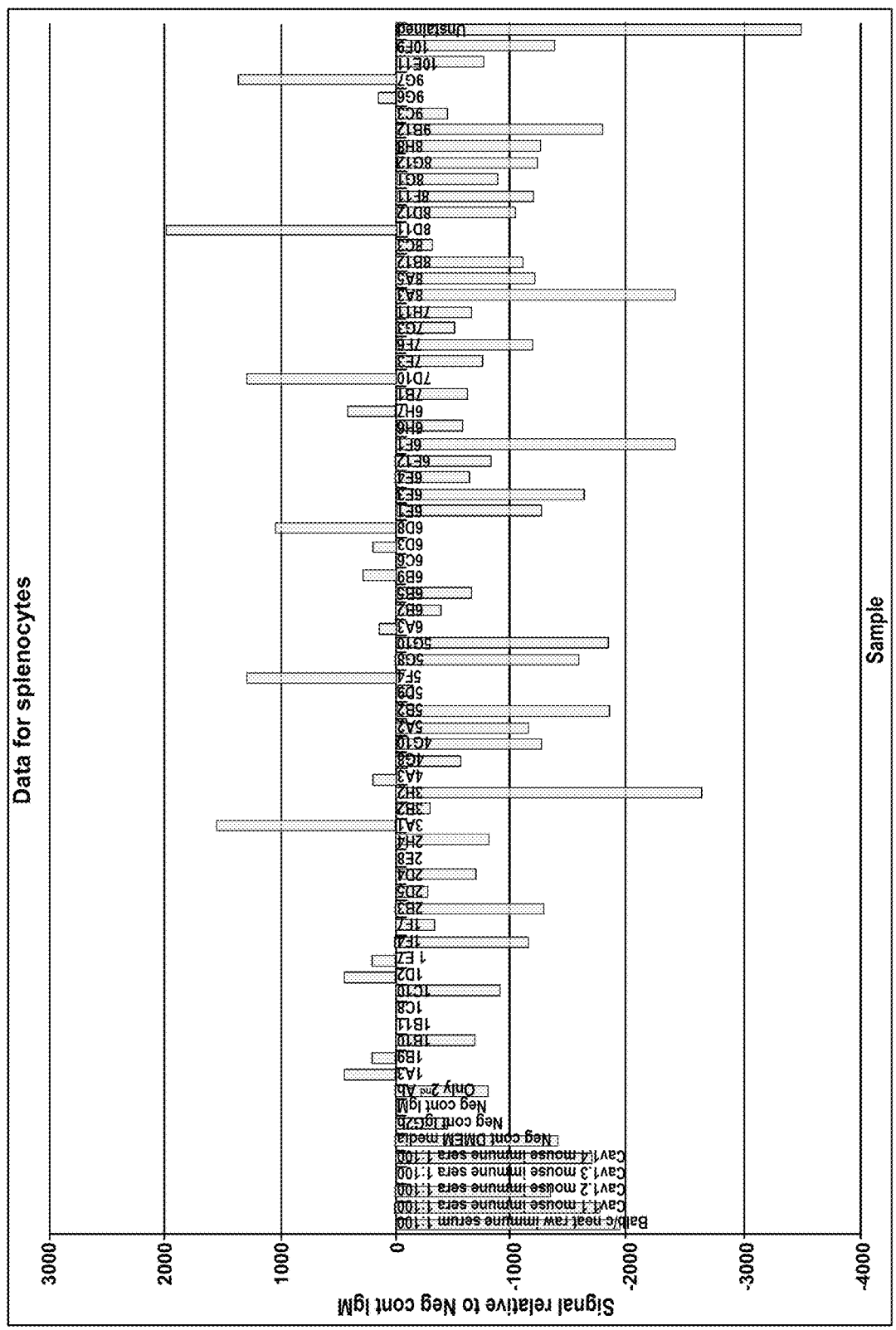
FIG. 5 shows representative results of flow cytometry experiments performed on antibodies produced by hybridoma clones. Supernatants containing monoclonal antibodies produced by hybridomas were tested to determine binding to wild-type mouse splenocytes. The binding signals of the monoclonal antibodies relative to IgM control antibody are displayed.

Antibodies collected from hybridoma clones were tested for their ability to bind to wild-type mouse splenocytes. Splenocytes consist of a variety of cell populations such as T and B lymphocytes, dendritic cells and macrophages. Negative controls included unstained (no antibody or media), negative control DMEM media, negative control IgG2b antibody, and negative IgM antibody. Binding was quantified as a ratio of test antibody signal to negative control igG2b antibody (FIG. 4) or negative control IgM antibody (FIG. 5). Representative results (FIGS. 4 and 5) demonstrate that monoclonal antibodies that bind to splenocytes were identified, for example, clones 3A1, 5F4, and 7D10.

Figure 6:
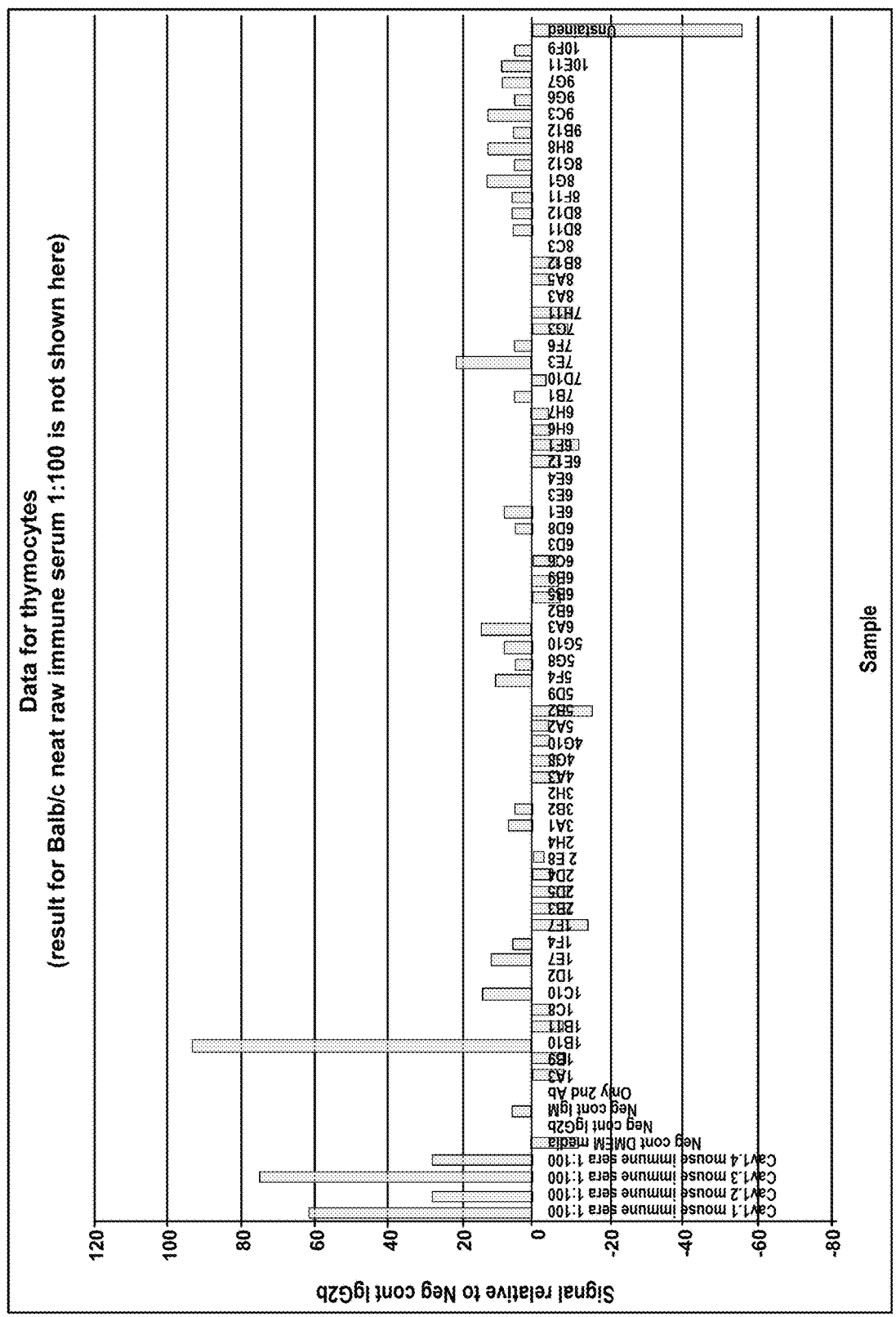
FIG. 6 shows representative results of flow cytometry experiments performed on antibodies produced by hybridoma clones. Supernatants containing monoclonal antibodies produced by hybridomas were tested to determine binding to wild-type mouse thymocytes. The binding signals of the monoclonal antibodies relative to IgG2b control antibody are displayed.
Figure 7:
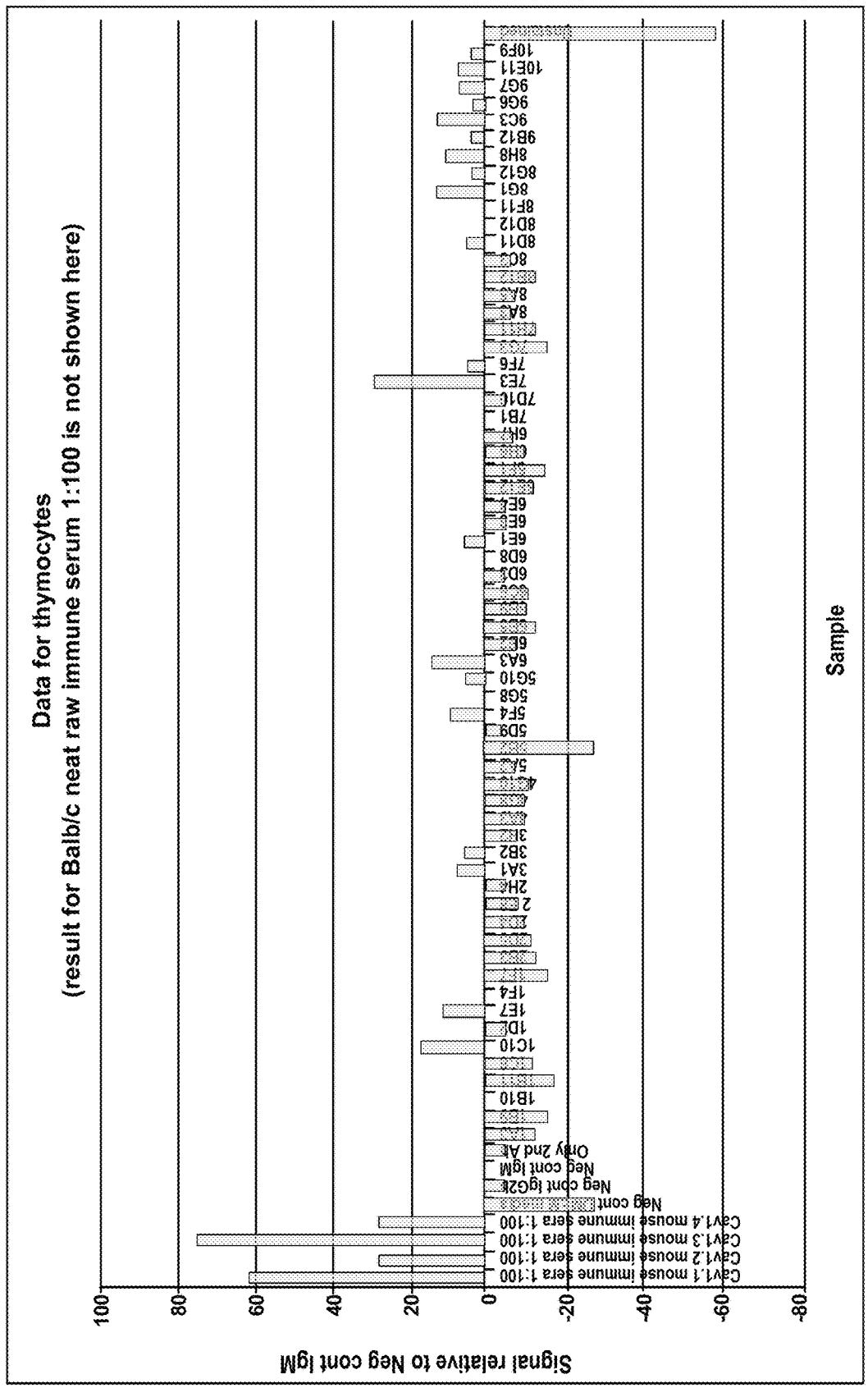
FIG. 7 shows representative results of flow cytometry experiments performed on antibodies produced by hybridoma clones. Supernatants containing monoclonal antibodies produced by hybridomas were tested to determine binding to wild-type mouse thymocytes. The binding signals of the monoclonal antibodies relative to IgM control antibody are displayed.

A similar experiment tested antibodies collected from hybridoma clones for their ability to bind to wild-type mouse thymocytes. Thymocytes are hematopoietic progenitor cells present in the thymus that differentiate into mature T lymphocytes. Immunosera from mice immunized with Cav1.1, Cav1.2, Cav1.3, and Cav1.4 were used as positive controls. Negative controls included unstained (no antibody or media), negative control DMEM media, negative control IgG2b antibody, and negative IgM antibody. Binding was quantified as a ratio of test antibody signal to negative control igG2b antibody (FIG. 6) or negative control IgM antibody (FIG. 7). Representative results (FIGS. 5 and 6) demonstrate that monoclonal antibodies that bind to thymocytes were identified, for example, clones 1E10 and 7E3.

Taken together, these results demonstrate that monoclonal antibodies were generated that can recognize extracellular pore loops of L-type voltage-gated calcium channel alpha 1 subunits and that can bind to targets on immune cells. Following this series of experiments, 31 clones on interest were identified (Summarized in FIG. 8) based on their ability to bind to an L-type voltage-gated calcium channel subtype and to bind to a target on a splenocyte or thymocyte. Twenty-eight hybridomas were identified that produce antibodies selective for one subtype (Cav1.4, Cav1.3, Cav1.2, or Cav1.1), three hybridomas were identified that produce antibodies selective for two subtypes (Cav1.4 and Cav1.2; or Cav1.3 and Cav1.2), and one hybridoma was identified that produces antibody selective for three subtypes (Cav1.4, Cav1.3, and Cav1.2).

Example 3

Hybridoma Antibodies Bind to and Inhibit Growth of Jurkat T-Cells

The hybridoma clones were additionally evaluated in a flow cytometry-based binding assay using the human Jurkat leukemia cell line (Jurkat). Cell binding and growth inhibition assays were performed using standard techniques. The results are shown in Table E2 below.

TABLE E2

Jurkat Binding and Growth Assays

| Clone ID | Binding Specificity | | | | | Cell binding | Growth Inhibition |
| --- | --- | --- | --- | --- | --- | --- | --- |
| | Cav1.1 | Cav1.2 | Cav1.3 | Cav1.4 | Isotype | Jurkat | |
| 1C8 | | | Yes | | IgG | Yes | Yes |
| 1C10 | | | | Yes | IgG | Yes | Yes |
| 1D2 | | Yes | Yes | Yes | IgM | Yes | Yes |
| 1E7 | Yes | | | | IgM | Yes | Yes |
| 1F4 | Yes | | | | IgG | Yes | Yes |
| 2D5 | | | Yes | | IgG | Yes | Yes |
| 5F4 | | | Yes | | IgG | Yes | Yes |
| 5G10 | | | Yes | | IgG | NS | Yes |
| 6A3 | | Yes | Yes | | IgG | Yes | Yes |
| 6C6 | | Yes | | | IgG | Yes | NS |
| 6E1 | | | Yes | | IgG | Yes | Yes |
| 6H7 | | | Yes | | IgG | Yes | Yes |
| 8G1 | | | Yes | | IgG | Yes | Yes |
| 9C3 | | | Yes | | IgG | Yes | Yes |
| 10E11 | | | Yes | | IgG | Yes | Yes |

NS—Non-specific at time of assay.

These results show that supernatants from the hybridoma clones in Table E2 were able to bind to and inhibit the growth of human Jurkat T-cells, evidencing the therapeutic potential of these antibodies in the treatment of various cancers, including hematopoietic cancers.

---

```
                            SEQUENCE LISTING

Sequence total quantity: 108
SEQ ID NO: 1            moltype = AA  length = 12
FEATURE                 Location/Qualifiers
REGION                  1..12
                        note = Conserved mammalian extracellular domain of Cav1.4
source                  1..12
                        mol_type = protein
                        organism = unidentified
SEQUENCE: 1
GPGRPGDAPH TG                                                              12

SEQ ID NO: 2            moltype = AA  length = 16
FEATURE                 Location/Qualifiers
REGION                  1..16
                        note = Conserved mammalian extracellular domain of Cav1.3
source                  1..16
                        mol_type = protein
                        organism = unidentified
SEQUENCE: 2
LTKETEGGNH SSGKSG                                                          16

SEQ ID NO: 3            moltype = AA  length = 15
FEATURE                 Location/Qualifiers
REGION                  1..15
                        note = Conserved mammalian extracellular domain of Cav1.2
source                  1..15
                        mol_type = protein
                        organism = unidentified
SEQUENCE: 3
ATKADGANAL GGKGA                                                           15

SEQ ID NO: 4            moltype = AA  length = 13
FEATURE                 Location/Qualifiers
REGION                  1..13
                        note = Conserved mammalian extracellular domain of Cav1.1
source                  1..13
                        mol_type = protein
                        organism = unidentified
SEQUENCE: 4
PMQIELRHRE WVH                                                             13

SEQ ID NO: 5            moltype = AA  length = 1977
FEATURE                 Location/Qualifiers
```

```
source                  1..1977
                        mol_type = protein
                        organism = Homo sapiens
SEQUENCE: 5
MSESEGGKDT TPEPSPANGA GPGPEWGLCP GPPAVEGESS GASGLGTPKR RNQHSKHKTV    60
AVASAQRSPR ALFCLTLANP LRRSCISIVE WKPFDILILL TIFANCVALG VYIPFPEDDS   120
NTANHNLEQV EYVFLVIFTV ETVLKIVAYG LVLHPSAYIR NGWNLLDFII VVVGLFSVLL   180
EQGPGRPGDA PHTGGKPGGF DVKALRAFRV LRPLRLVSGV PSLHIVLNSI MKALVPLLHI   240
ALLVLFVIII YAIIGLELFL GRMHKTCYFL GSDMEAEEDP SPCASSGSGR ACTLNQTECR   300
GRWPGPNGGI TNFDNFFFAM LTVFQCVTME GWTDVLYWMQ DAMGYELPWV YFVSLVIFGS   360
FFVLNLVLGV LSGEFSKERE KAKARGDFQK QREKQQMEED LRGYLDWITQ AEELDMEDPS   420
ADDNLGSMAE EGRAGHRPQL AELTNRRRGR LRWFSHSTRS THSTSSHASL PASDTGSMTE   480
TQGDEDEEEG ALASCTRCLN KIMKTRVCRR LRRANRVLRA RCRRAVKSNA CYWAVLLLVF   540
LNTLTIASEH HGQPVWLTQI QEYANKVLLC LFTVEMLLKL YGLGPSAYVS SFFNRFDCFV   600
VCGGILETTL VEVGAMQPLG ISVLRCVRLL RIFKVTRHWA SLSNLVASLL NSMKSIASLL   660
LLLFLFIIIF SLLGMQLFGG KFNFDQTHTK RSTFDTFPQA LLTVFQILTG EDWNVVMYDG   720
IMAYGGPFFP GMLVCIYFII LFICGNYILL NVFLAIAVDN LASGDAGTAK DKGGEKSNEK   780
DLPQENEGLV PGVEKEEEEG ARREGADMEE EEEEEEEEEE EEEEGAGGV ELLQEVVPKE    840
KVVPIPEGSA FFCLSQTNPL RKGCHTLIHH HVFTNLILVF IILSSVSLAA EDPIRAHSFR   900
NHILGYFDYA FTSIFTVEIL LKMTVFGAFL HRGSFCRSWF NMLDLLVVSV SLISFGIHSS   960
AISVVKILRV LRVLRPLRAI NRAKGLKHVV QCVFVAIRTI GNIMIVTTLL QFMFACIGVQ  1020
LFKGKFYTCT DEAKHTPQEC KGSFLVYPDG DVSRPLVRER LWVNSDFNFD NVLSAMMALF  1080
TVSTFEGWPA LLYKAIDAYA EDHGPIYNYR VEISVFFIVY IIIIAFFMMN IFVGFVIITF  1140
RAQGEQEYQN CELDKNQRQC VEYALKAQPL RRYIPKNPHQ YRVWATVNSA AFEYLMFLLI  1200
LLNTVALAMQ HYEQTAPFNY AMDILNMVFT GLFTIEMVLK IIAFKPKHYF TDAWNTFDAL  1260
IVVGSIVDIA VTEVNNGGHL GESSEDSSRI SITFFRLFRV MRLVKLLSKG EGIRTLLWTF  1320
IKSFQALPYV ALLIAMIFFI YAVIGMQMFG KVALQDGTQI NRNNNFQTFP QAVLLLFRCA  1380
TGEAWQEIML ASLPGNRCDP ESDFGPGEEF TCGSNFAIAY FISFFMLCAF LIINLFVAVI  1440
MDNFDYLTRD WSILGPHHLD EFKRIWSEYD PGAKGRIKHL DVVALLRRIQ PPLGFGKLCP  1500
HRVACKRLVA MNMPLNSDGT VTFNATLFAL VRTSLKIKTE GNLEQANQEL RIVIKKIWKR  1560
MKQKLLDEVI PPPDEEEVTV GKFYATFLIQ DYFRKFRRRK EKGLLGNDAA PSTSSALQAG  1620
LRSLQDLGPE MRQALTCDTE EEEEEGQEGV EEEDEKDLET NKATMVSQPS ARRGSGISVS  1680
LPVGDRLPDS LSFGPSDDDR GTPTSSQPSV PQAGSNTHRR GSGALIFTIP EEGNSQPKGT  1740
KGQNKQDEDE EVPDRLSYLD EQAGTPPCSV LLPPHRAQRY MDGHLVPRRR LLPPTPAGRK  1800
PSFTIQCLQR QGSCEDLPIP GTYHRGRNSG PNRAQGSWAT PPQRGRLLYA PLLLVEEGAA  1860
GEGYLGRSSG PLRTFTCLHV PGTHSDPSHG KRGSADSLVE AVLISEGLGL FARDPRFVAL  1920
AKQEIADACR LTLDEMDNAA SDLLAQGTSS LYSDEESILS RFDEEDLGDE MACVHAL     1977

SEQ ID NO: 6            moltype = AA   length = 2161
FEATURE                 Location/Qualifiers
source                  1..2161
                        mol_type = protein
                        organism = Homo sapiens
SEQUENCE: 6
MMMMMMMKKM QHQRQQQADH ANEANYARGT RLPLSGEGPT SQPNSSKQTV LSWQAAIDAA    60
RQAKAAQTMS TSAPPPVGSL SQRKQQYAK SKKQGNSSNS RPARALFCLS LNNPIRRACI    120
SIVEWKPFDI FILLAIFANC VALAIYIPFP EDDSNSTNHN LEKVEYAFLI IFTVETFLKI   180
IAYGLLLHPN AYVRNGWNLL DFVIVIVGLF SVILEQLTKE TEGGNHSSGK SGGFDVKALR   240
AFRVLRPLRL VSGVPSLQVV LNSIIKAMVP LLHIALLVLF VIIIYAIIGL ELFIGKMHKT   300
CFFADSDIVA EEDPAPCAFS GNGRQCTANG TECRSGWVGP NGGITNFDNF AFAMLTVFQC   360
ITMEGWTDVL YWMNDAMGFE LPWVYFVSLV IFGSFFVLNL VLGVLSGEFS KEREKAKARG   420
DFQKLREKQQ LEEDLKGYLD WITQAEDIDP ENEEEGGEEG KRNTSMPTSE TESVNTENVS   480
GEGENRGCCG SLCQAISKSK LSRRWRRWNR FNRRRCRAAV KSVTFYWLVI VLVFLNTLTI   540
SSEHYNQPDW LTQIQDIANK VLLALFTCEM LVKMYSLGLQ AYFVSLFNRF DCFVVCGGIT   600
ETILVELEIM SPLGISVFRC VRLLRIFKVT RHWTSLSNLV ASLLNSMKSI ASLLLLLFLF   660
IIIFSLLGMQ LFGGKFNFDE TQTKRSTFDN FPQALLTVFQ ILTGEDWNAV MYDGIMAYGG   720
PSSSGMIVCI YFIILFICGN YILLNVFLAI AVDNLADAES LNTAQKEEAE EKERKKIARK   780
ESLENKKNNK PEVNQIANSD NKVTIDDYRE EDEDKDPYPP CDVPVGEEEE EEEEDEPEVP   840
AGPRPRRISE LNMKEKIAPI PEGSAFFILS KTNPIRVGCH KLINHHIFTN LILVFIMLSS   900
AALAAEDPIR SHSFRNTILG YFDYAFTAIF TVEILLKMTT FGAFLHKGAF CRNYFNLLDM   960
LVVGSLVSF GIQSSAISVV KILRVLRVLR PLRAINRAKG LKHVVQCFFV AIRTIGNIMI   1020
VTTLLQFMFA CIGVQLFKGK FYRCTDEAKS NPEECRGLFI LYKDGDVDSP VVRERIWQNS  1080
DFNFDNVLSA MMALFTVSTF EGWPALLYKA IDSNGENIGP IYNHRVEISI FFIIYIIVA   1140
FFMMNIFVGF VIVTFQEGQE KEYKNCELDK NQRQCVEYAL KARPLRRYIP KNPYQYKFWY  1200
VVNSSPFEYM MFVLIMLNTL CLAMQHYEQS KMFNDAMDIL NMVFTGVFTV EMVLKVIAFK  1260
PKGYFSDAWN TFDSLIVIGS IIDVALSEAD PTESENVPVP TATPGNSEES NRISITFFRL  1320
FRVMRLVKLL SRGEGIRTLL WTFIKSFQAL PYVALLIAML FFIYAVIGMQ MFGKVAMRDN  1380
NQINRNNNFQ TFPQAVLLLF RCATGEAWQE IMLACLPGEL CDPESDYNPG EEYTCGSNFA  1440
IVYFISFYML CAFLIINLFV AVIMDNFDYL TRDWSILGPH HLDEFKRIWS EYDPEAKGRI  1500
KHLDVVTLLR RIQPPLGFGK LCPHRVACKR LVAMNMPLNS DGTVMFNATL FALVRTALKI  1560
KTEGNLEQAN EELRAVIKKI WKKTSMKLLD QVVPPAGDDE VTVGKFYATF LIQDYFRKFK  1620
KRKEQGLVGK YPAKNTTIAL QAGLRTLHDI GPEIRRAISC DLQDDEPEET KREEEDDVFK  1680
RNGALLGNHV NHVNSDRRDS LQQTNTTHRP LHVQRPSIPP ASDTEKPLFP PAGNSVCHNH  1740
HNHNSIGKQV PTSTNANLNN ANMSKAAHGK RPSIGNLEHV SENGHHSSHK HDREPQRRSS  1800
VKRTRYYETY IRSDSGDEQL PTICREDPEI HGYFRDPHCL GEQEYFSSEE CYEDDSSPTW  1860
SRQNYGYYSR YPGRNIDSER PRGYHHPQGF LEDDDSPVCY DSRRSPRRRL LPPTPASHRR  1920
SSFNFECLRR QSSQEEVPSS PIFPHRTALP LHLMQQQIMA VAGLDSSKAQ KYSPSHSTRS  1980
WATPPATPPY RDWTPCYTPL IQVEQSEALD QVNGSLPSLH RSSWYTDEPD ISYRTFTPAS  2040
LTVPSSFRNK NSDKQRSADS LVEAVLISEG LGRYARDPKF VSATKHEIAD ACDLTIDEME  2100
```

| | | | | |
|---|---|---|---|---|
| SAASTLLNGN | VRPRANGDVG | PLSHRQDYEL | QDFGPGYSDE | EPDPGRDEED LADEMICITT 2160 |
| L | | | | 2161 |

```
SEQ ID NO: 7              moltype = AA   length = 2221
FEATURE                   Location/Qualifiers
source                    1..2221
                          mol_type = protein
                          organism = Homo sapiens
SEQUENCE: 7
MVNENTRMYI PEENHQGSNY GSPRPAHANM NANAAAGLAP EHIPTPGAAL SWQAAIDAAR   60
QAKLMGSAGN ATISTVSSTQ RKRQQYGKPK KQGSTTATRP PRALLCLTLK NPIRRACISI  120
VEWKPFEIII LLTIFANCVA LAIYIPFPED DSNATNSNLE RVEYLFLIIF TVEAFLKVIA  180
YGLLFHPNAY LRNGWNLLDF IIVVVGLFSA ILEQATKADG ANALGGKGAG FDVKALRAFR  240
VLRPLRLVSG VPSLQVVLNS IIKAMVPLLH IALLVLFVII IYAIIGLELF MGKMHKTCYN  300
QEGIADVPAE DDPSPCALET GHGRQCQNGT VCKPGWDGPK HGITNFDNFA FAMLTVFQCI  360
TMEGWTDVLY WVNDAVGRDW PWIYFVTLII IGSFFVLNLV LGVLSGEFSK EREKAKARGD  420
FQKLREKQQL EEDLKGYLDW ITQAEDIDPE NEDEGMDEEK PRNMSMPTSE TESVNTENVA  480
GGDIEGENCG ARLRHRISKS KFSRYWRRWN RFCRRKCRAA VKSNVFYWLV IFLVFLNTLT  540
IASEHYNQPN WLTEVQDTAN KALLALFTAE MLLKMYSLGL QAYFVSLFNR FDCFVVCGGI  600
LETILVETKI MSPLGISVLR CVRLLRIFKI TRYWNSLSNL VASLLNSVRS IASLLLLLFL  660
FIIIFSLLGM QLFGGKFNFD EMQTRRSTFD NFPQSLLTVF QILTGEDWNS VMYDGIMAYG  720
GPSFPGMLVC IYFIILFICG NYILLNVFLA IAVDNLADAE SLTSAQKEEE EEKERKKLAR  780
TASPEKKQEL VEKPAVGESK EEKIELKSIT ADGESPPATK INMDDLQPNE NEDKSPYPNP  840
ETTGEEDEEE PEMPVGPRPR PLSELHLKEK AVPMPEASAF FIFSSNNRFR LQCHRIVNDT  900
IFTNLILFFI LLSSISLAAE DPVQHTSFRN HILFYFDIVF TTIFTIEIAL KILGNADYVF  960
TSIFTLEIIL KMTAYGAFLH KGSFCRNYFN ILDDLLVVSVS LISFGIQSSA INVVKILRVL 1020
RVLRPLRAIN RAKGLKHVVQ CVFVAIRTIG NIVIVTTLLQ FMFACIGVQL FKGKLYTCSD 1080
SSKQTEAECK GNYITYKDGE VDHPIIQPRS WENSKFDFDN VLAAMMALFT VSTFEGWPEL 1140
LYRSIDSHTE DKGPIYNYRV EISIFFIIYI IIIAFFMMNI FVGFVIVTFQ EQGEQEYKNC 1200
ELDKNQRQCV EYALKARPLR RYIPKNQHQY KVWYVVNSTY FEYLMFVLIL LNTICLAMQH 1260
YGQSCLFKIA MNILNMLFTG LFTVEMILKL IAFKPKGYFS DPWNVFDFLI VIGSIIDVIL 1320
SETNHYFCDA WNTFDALIVV GSIVDIAITE VNPAEHTQCS PSMNAEEENSR ISITFFRLFR 1380
VMRLVKLLSR GEGIRTLLWT FIKSFQALPY VALLIVMLFF IYAVIGMQVF GKIALNDTTE 1440
INRNNNFQTF PQAVLLLFRC ATGEAWQDIM LACMPGKKCA PESEPSNSTE GETPCGSSFA 1500
VFYFISFYML CAFLIINLFV AVIMDNFDYL TRDWSILGPH HLDEFKRIWA EYDPEAKGRI 1560
KHLDVVTLLR RIQPPLGFGK LCPHRVACKR LVSMNMPLNS DGTVMFNATL FALVRTALRI 1620
KTEGNLEQAN EELRAIIKKI WKRTSMKLLD QVVPPAGDDE VTVGKFYATF LIQEYFRKFK 1680
KRKEQGLVGK PSQRNALSLQ AGLRTLHDIG PEIRRAISGD LTAEEELDKA MKEAVSAASE 1740
DDIFRRAGGL FGNHVSYYQS DGRSAFPQTF TTQRPLHINK AGSSQGDTES PSHEKLVDST 1800
FTPSSYSSTG SNANINNANN TALGRLPRPA GYPSTVSTVE GHGPPLSPAI RVQEVAWKLS 1860
SNRERHVPMC EDLELRRDSG SAGTQAHCLL LRRANPSRCH SRESQAAMAG QEETSQDETY 1920
EVKMNHDTEA CSEPSLLSTE MLSYQDDENR QLTLPEEDKR DIRQSPKRGF LRSASLGRRA 1980
SFHLECLKRQ KDRGGDISQK TVLPLHLVHH QALAVAGLSP LLQRSHSPAS FPRPFATPPA 2040
TPGSRGWPPQ PVPTLRLEGV ESSEKLNSSF PSIHCGSWAE TTPGGGGSSA ARRVRPVSLM 2100
VPSQAGAPGR QFHGSASSLV EAVLISEGLG QFAQDPKFIE VTTQELADAC DMTIEEMESA 2160
ADNILSGGAP QSPNGALLPF VNCRDAGQDR AGGEEDAGCV RARGRPSEEE LQDSRVYVSS 2220
L                                                                2221

SEQ ID NO: 8              moltype = AA   length = 1873
FEATURE                   Location/Qualifiers
source                    1..1873
                          mol_type = protein
                          organism = Homo sapiens
SEQUENCE: 8
MEPSSPQDEG LRKKQPKKPV PEILPRPPRA LFCLTLENPL RKACISIEVW KPFETIILLT   60
IFANCVALAV YLPMPEDDNN SLNLGLEKLE YFFLIVFSIE AAMKIIAYGF LFHQDAYLRS  120
GWNVLDFTIV FLGVFTVILE QVNVIQSHTA PMSSKGAGLD VKALRAFRVL RPLRLVSGVP  180
SLQVVLNSIF KAMLPLFHIA LLVLFMVIIY AIIGLELFKG KMHKTCYFIG TDIVATVENE  240
EPSPCARTGS GRRCTINGSE CRGGWPGPNH GITHFDNFAF SMLTVYQCIT MEGWTDVLYW  300
VNDAIGNEWP WIYFVTLILL GSFFILNLVL GVLSGEFTKE REKAKSRGTF QKLREKQQLD  360
EDLRGYMSWI TQGEVMDVED FREGKLSLDE GGSDTESLYE IAGLNKIIQF IRHWRQWNRI  420
FRWKCHDIVK SKVFYWLVIL IVALNTLSIA SEHHNQPLWL TRLQDIANRV LLSLFTTEML  480
MKMYGLGLRQ YFMSIFNRFD CFVVCSGILE ILLVESGAMT PLGISVLRCI RLLRIFKITK  540
YWTSLSNLVA SLLNSIRSIA SLLLLLFLFI VIFALLGMQL FGGRYDFEDT EVRRSNFDNF  600
PQALISVFQV LTGEDWTSMM YNGIMAYGGP SYPGMLVCIY FIILFVCGNY ILLNVFLAIA  660
VDNLAEAESL TSAQKAKAEE KKRRKMSKGL PDKSEEEKST MAKKLEQKPK GEGIPTTAKL  720
KIDEFESNVN EVKDPYPSAD FPGDDEEDEP EIPLSPRPRP LAELQLKEKA VPIPEASSFF  780
IFSPTNKIRV LCHRIVNATW FTNFILLFIL LSSAALAAED PIRADSMRNQ ILKHFDIGFT  840
SVFTVEIVLK MTTYGAFLHK GSFCRNYFNM LDLLVAVSL ISMGLESSAI SVVKILRVLR  900
VLRPLRAINR AKGLKHVVQC MFVAISTIGN IVLVTTLLQF MFACIGVQLF KGKFFRCTDL  960
SKMTEEECRG YYYVYKDGDP MQIELRHREW VHSDFHFDNV LSAMMSLFTV STFEGWPQLL 1020
YKAIDSNAED VGPIYNNRVE MAIFFIIYII LIAFFMMNIF VGFVIVTFQE QGETEYKNCE 1080
LDKNQRQCVE YALKARPLRC YIPKNPYQYQ VWYIVTSSYF EYLMFALIML NTICLGMQHY 1140
NQSEQMNHIS DILNVFAFTII FTLEMILKLM AFKARGYFGD PWNVFDFLIV IGSIIDVILS 1200
EIDTFLASSG GLYCLGGGCG NVDPDESARI SSAFFRLFRV MRLIKLLSRA EGVRTLLWTF 1260
IKSFQALPYV ALLIVMLFFI YAVIGMQMFG KIALVDGTQI NRNNNFQTFP QAVLLLFRCA 1320
TGEAWQEILL ACSYGKLCDP ESDYAPGEEY TCGTNFAYYY FISFYMLCAF LVINLFVAVI 1380
MDNFDYLTRD WSILGPHHLD EFKAIWAEYD PEAKGRIKHL DVVTLLRRIQ PPLGFGKFCP 1440
HRVACKRLVG MNMPLNSDGT VTFNATLFAL VRTALKITE GNFEQANEEL RAIIKKIWKR 1500
```

```
TSMKLLDQVI PPIGDDEVTV GKFYATFLIQ EHFRKFMKRQ EEYYGYRPKK DIVQIQAGLR    1560
TIEEEAAPEI CRTVSGDLAA EEELERAMVE AAMEEGIFRR TGGLFGQVDN FLERTNSLPP    1620
VMANQRPLQF AEIEMEEMES PVFLEDFPQD PRTNPLARAN TNNANANVAY GNSNHSNSHV    1680
FSSVHYEREF PEETETPATR GRALGQPCRV LGPHSKPCVE MLKGLLTQRA MPRGQAPPAP    1740
CQCPRVESSM PEDRKSSTPG SLHEETPHSR STRENTSRCS APATALLIQK ALVRGGLGTL    1800
AADANFIMAT GQALADACQM EPEEVEIMAT ELLKGREAPE GMASSLGCLN LGSSLGSLDQ    1860
HQGSQETLIP PRL                                                      1873

SEQ ID NO: 9            moltype = AA   length = 1984
FEATURE                 Location/Qualifiers
source                  1..1984
                        mol_type = protein
                        organism = Mus musculus
SEQUENCE: 9
MSESEVGKDT TPEPSPANGT GPGPEWGLCP GPPTVGTDTS GASGLGTPRR RTQHNKHKTV    60
AVASAQRSPR ALFCLTLTNP IRRSCISIVE WKPFDILILL TIFANCVALG VYIPFPEDDS    120
NTANHNLEQV EYVFLVIFTV ETVLKIVAYG LVLHPSAYIR NGWNLLDFII VVVGLFSVLL    180
EQGPGRPGDA PHTGGKPGGF DVKALRAFRV LRPLRLVSGV PSLHIVLNSI MKALVPLLHI    240
ALLVLFVIII YAIIGLELFL GRMHKTCYFL GSDMEAEEDP SPCASSGSGR SCTLNHTECR    300
GRWPGPNGGI TNFDNFFFAM LTVFQCITME GWTDVLYWMQ DAMGYELPWV YFVSLVIFGS    360
FFVLNLVLGV LSGEFSKERE KAKARGDFQK LREKQQMEED LRGYLDWITQ AEELDLHDPS    420
VDGNLASLAE EGRAGHRPQL SELTNRRRGR LRWFSHSTRS THSTSSHASL PASDTGSMTD    480
TPGDEDEEEG TMASCTRCLN KIMKTRICRH FRRANRGLRA RCRRAVKSNA CYWAVLLLVF    540
LNTLTIASEH HGQPLWLTQT QEYANKVLLC LFTVEMLLKL YGLGPSVYVA SFFNRFDCFV    600
VCGGILETTL VEVGAMQPLG ISVLRCVRLL RIFKVTRHWA SLSNLVASLL NSMKSIASLL    660
LLLFLFIIIF SLLGMQLFGG KFNFDQTHTK RSTFDTFPQA LLTVFQILTG EDWNVVMYDG    720
IMAYGGPFFP GMLVCVYFII LFICGNYILL NVFLAIAVDN LASGDAGTAK DKGREKSSEG    780
NPPKENKVLV PGGENEDAKG ARSEGAAPGM EEEEEEEEEE EEEEEENGA GHVELLQEVV    840
PKEKVVPIPE GSAFFCLSQT NPLRKACHTL IHHHIFTSLI LVFIILSSVS LAAEDPIRAH    900
SFRNHILGYF DYAFTSIFTV EILLKMTVFG AFLHRGSFCR SWFNLLDLLV VSVSLISFGI    960
HSSAISVVKI LRVLRVLRPL RAINRAKGLK HVVQCVFVAI RTIGNIMIVT TLLQFMFACI    1020
GVQLFKGKFY SCTDEAKHTL KECGSFLIY PDGDVSRPLV RERLWVNSDF NPDNVLSAMM    1080
ALFTVSTFEG WPALLYKAID ANAEDEGPIY NYHVEISVFF IVYIIIIAFF MMNIFVGFVI    1140
ITFRAQGEQE YQNCELDKNQ RQCVEYALKA QPLRRYIPKN PHQYRVWATV NSAAFEYLMF    1200
LLILLNTVAL AMQHYEQTAP FNYAMDILNM VFTGLFTIEM VLKIIAFKPK HYFADAWNTF    1260
DALIVVGSVV DIAVTEVNNG GHLGESSEDS SRISITFFRL FRVMRLVKLL SKGEGIRTLL    1320
WTFIKSFQAL PYVALLIAMI FFIYAVIGMQ MFGKVALQDG TQINRNNNFQ TFPQAVLLLF    1380
RCATGEAWQE IMLASLPGNR CDPESDFGPG EEFTCGSSFA IVYFISFFML CAFLIINLFV    1440
AVIMDNFDYL TRDWSILGPH HLDEFKRIWS EYDPGAKGRI KHLDVVALLR RIQPPLGFGK    1500
LCPHRVACKR LVAMNVPLNS DGTVTFNATL FALVRTSLKI KTEGNLDQAN QELRMVIKKI    1560
WKRIKQKLLD EVIPPPDEEE VTVGKFYATF LIQDYFRKFR RRKEKGLLGR EAPTSTSSAL    1620
QAGLRSLQDL GPEIRQALTY DTEEEEEEEE AVGQEAEEEE AENNPEPYKD SIDSQPQSRW    1680
NSRISVSLPV KEKLPDSLST GPSDDDGLAP NSRQPSVIQA GSQPHRRSSG VFMFTIPEEG    1740
SIQLKGTQGQ DNQNEEQEVP DWTPDDDEQA GTPSNPVLLP PHWSQQHVNG HHVPRRRLLP    1800
PTPAGRKPSF TIQCLQRQGS CEDLPIPGTY HRGRTSGPSR AQGSWAAPPQ KGRLLYAPLL    1860
LVEESTVGEG YLGKLGGPLR TFTCLQVPGA HPNPSHRKRG SADSLVEAVL ISEGLGLFAQ    1920
DPRFVALAKQ EIADACHLTL DEMDSAASDL LAQRTTSLYS DEESILSRFD EEDLGDEMAC    1980
VHAL                                                                1984

SEQ ID NO: 10           moltype = AA   length = 2166
FEATURE                 Location/Qualifiers
source                  1..2166
                        mol_type = protein
                        organism = Mus musculus
SEQUENCE: 10
MNLPTFSSDL ILIKSVLSQE TDARYKGRVV SAVESTEDFS QAFAEANYAR GTRLPISGEG    60
PTSQPNSSKQ TVLSWQAAID AARQAKAAQT MSTSAPPPVG SLSQRKRQQY AKSKKQGNSS    120
NSRPARALFC LSLNNPIRRA CISIVEWKPF DIFILLAIFA NCVALAIYIP FPEDDSNSTN    180
HNLEKVEYAF LIIFTVETFL KIIAYGLLLH PNAYVRNGWN LLDFVIVIVG LFSVILEQLT    240
KETEGGNHSS GKSGGFDVKA LRAFRVLRPL RLVSGVPSLQ VVLNSIIKAM VPLLHIALLV    300
LFVIIIYAII GLELFIGKMH KTCFFADSDI VAEEDPAPCA FSGNGRQCTA NGTECRSGWV    360
GPNGGITNFD NFAFAMLTVF QCITMEGWTD VLYWVNDAIG WEWPWVYFVS LIILGSFFVL    420
NLVLGVLSGE FSKEREKAKA RGDFQKLREK QQLEEDLKGY LDWITQAEDI DPENEEEGGE    480
EGKRNTSMPT SETESVNTEN VSGEGETQGC CGTLCQAISK SKLSRRWRRW NRFNRRRCRA    540
AVKSVTFYWL VIVLVFLNTL TISSEHYNQP DWLTQIQDIA NKVLLALFTC EMLVKMYSLG    600
LQAYFVSLFN RFDCFVVCGG ITETILVELE LMSPLGVSVF RCVRLLRIFK VTRHWTSLSN    660
LVASLLNSMK SIASLLLLF LFIIIFSLLG MQLFGGKFNF DETQTKRSTF DNFPQALLTV    720
FQILTGEDWN AVMYDGIMAY GGPSSSGMIV CIYFIILFIC GNYILLNVFL AIAVDNLADA    780
ESLNTAQKEE AEEKERKKIA RKESLENKKN NKPEVNQIAN SDNKVTIDDY QEDAEDKDPY    840
PPCDVPVGEE EEEEEEDEPE VPAGRPRRI SELNMKEKIA PIPEGSAFFI LSKTNPIRVG    900
CHKLINHHIF TNLILVFIML SSAALAAEDP IRSHSFRNTI LGYFDYAFTA IFTVEILLKM    960
TTFGAFLHKG AFCRNYFNLL DMLVVGVSLV SFGIQSSAIS VVKILRVLRV LRPLRAINRA    1020
KGLKHVVQCV FVAIRTIGNI MIVTTLLQFM FACIGVQLFK GKFYRCTDEA KSNPEECRGL    1080
FILYKDGVD SPVVRERIWQ NSDFNFDNVL SAMMALFTVS TFEGWPALLY KAIDSNGENV    1140
GPVYNYRVEI SIFFIIYIII VAFFMMNIFV GFVIVTFQEQ GEKEYKNCEL DKNQRQCVEY    1200
ALKARPLRRY IPKNPYQYKF WYVVNSSPFE YMMFVLIMLN TLCLAMQHYE QSKMFNDAMD    1260
ILNMVFTGVF TVEMVLKVIA FKPKGYFSDA WNTFDSLIVI GSIIDVALSE ADNSEESNRI    1320
SITFFRLFRV MRVLKLLSRG EGIRTLLWTF IKSFQALPYV ALLIAMFFI YAVIGMQMFG    1380
KVAMRDNNQI NRNNNFQTFP QAVLLLFRCA TGEAWQEIML ACLPGKLCDP DSDYNPGEEY    1440
```

```
TCGSNFAIVY FISFYMLCAF LIINLFVAVI MDNFDYLTRD WSILGPHHLD EFKRIWSEYD  1500
PEAKGRIKHL DVVTLLRRIQ PPLGFGKLCP HRVACKRLVA MNMPLNSDGT VMFNATLFAL  1560
VRTALKIKTE GNLEQANEEL RAVIKKIWKK TSMKLLDQVV PPAGDDEVTV GKFYATFLIQ  1620
DYFRKFKKRK EQGLVGKYPA KNTTIALQAG LRTLHDIGPE IRRAISCDLQ DDEPEDSKPE  1680
EEDVFKRNGA LLGNHVNHVN SDRRDSLQQT NTTHRPLHVQ RPSMPPASDT EKPLFPPAGN  1740
SGCHNHHNHN SIGKQAPTST NANLNNANMS KAAHGKPPSI GNLEHVSENG HYSCKHDREL  1800
QRRSSIKRTR YYETYIRSES GDEQFPPTICR EDPEIHGYFR DPRCLGEQEY FSSEECCEDD  1860
SSPTWSRQNY NYYNRYPGSS MDFERPRGYH HPQGFLEDDD SPTGYDSRRS PRRRLLPPTP  1920
PSHRRSSFNF ECLRRQSSQD DVLPSPALPH RAALPLHLMQ QQIMAVAGLD SSKAQKYSPS  1980
HSTRSWATPP ATPPYRDWSP CYTPLIQVDR SESMDQVNGS LPSLHRSSWY TDEPDISYRT  2040
FTPASLTVPS SFRNKNSDKQ RSADSLVEAV LISEGLGRYA RDPKFVSATK HEIADACDLT  2100
IDEMESAAST LLNGSVCPRA NGDMGPISHR QDYELQDFGP GYSDEEPDPG REEEDLADEM  2160
ICITTL                                                           2166

SEQ ID NO: 11          moltype = AA   length = 2139
FEATURE                Location/Qualifiers
source                 1..2139
                       mol_type = protein
                       organism = Mus musculus
SEQUENCE: 11
MVNENTRMYV PEENHQGSNY GSPRPAHANM NANAAAGLAP EHIPTPGAAL SWQAAIDAAR    60
QAKLMGSAGN ATISTVSSTQ RKRQQYGKPK KQGGTTATRP PRALLCLTLK NPIRRACISI   120
VEWKPFEIII LLTIFANCVA LAIYIPFPED DSNATNSNLE RVEYLFLIIF TVEAFLKVIA   180
YGLLFHPNAY LRNGWNLLDF IIVVVGLFSA ILEQATKADG ANALGGKGAG FDVKALRAFR   240
VLRPLRLVSG VPSLQVVLNS IIKAMVPLLH IALLVLFVII IYAIIGLELF MGKMHKTCYN   300
QEGIIDVPAE EDPSPCALET GHGRQCQNGT VCKPGWDGPK HGITNFDNFA FAMLTVFQCI   360
TMEGWTDVLY WMQDAMGYEL PWVYFVSLVI FGSFFVLNLV LGVLSGEFSK EREKAKARGD   420
FQKLREKQQL EEDLKGYLDW ITQAEDIDPE NEDEGMDEDK PRNMSMPTSE TESVNTENVA   480
GGDIEGENCG ARLAHRISKS KFSRYWRRWN RFCRRKCRAA VKSNVFYWLV IFLVFLNTLT   540
IASEHYNQPH WLTEVQDTAN KALLALFTAE MLLKMYSLGL QAYFVSLFNR FDCFIVCGGI   600
LETILVETKI MSPLGISVLR CVRLLRIFKI TRYWNSLSNL VASLLNSVRS IASLLLLLFL   660
FIIIFSLLGM QLFGGKFNFD EMQTRRSTFD NFPQSLLTVF QILTGEDWNS VMYDGIMAYG   720
GPSFPGMLVC IYFIILFICG NYILLNVFLA IAVDNLADAE SLTSAQKEEE EKERKKLAR    780
TASPEKKQEV MEKPAVEESK EEKIELKSIT ADGESPPTTK INMDDLQPSE NEDKSPHSNP   840
DTAGEEDEEE PEMPVGPRPR PLSELHLKEK AVPMPEASAF FIFSPNNRFR LQCHRIVNDT   900
IFTNLILFFI LLSSISLAAE DPVQHTSFRN HILGNADYVF TSIFTLEIIL KMTAYGAFLH   960
KGSFCRNYFN ILDLLVVSVS LISFGIQSSA INVVKILRVL RVLRPLRAIN RAKGLKHVVQ  1020
CVFVAIRTIG NIVIVTTLLQ FMFACIGVQL FKGKLYTCSD SSKQTEAECK GNYITYKDGE  1080
VDHPIIQPRS WENSKFDFDN VLAAMMALFT VSTFEGWPEL LYRSIDSHTE DKGPIYNYRV  1140
EISIFFIIYI IIIAFFMMNI FVGFVIVTFQ EQGEQEYKNC ELDKNQRQCV EYALKARPLR  1200
RYIPKNQHQY KVWYVVNSTY FEYLMFVLIL LNTICLAMQH YGQSCLFKIA MNILNMLFTG  1260
LFTVEMILKL IAFKPKGYFS DPWNVFDFLI VIGSIIDVIL SETNPAEHTQ CSPSMSAEEN  1320
SRISITFFRL FRVMRLVKLL SRGEGIRTLL WTFIKSFQAL PYVALLIVML FFIYAVIGMQ  1380
VFGKIALNDT TEINRNNNFQ TFPQAVLLLF RCATGEAWQD IMLACMPGKK CAPESEPSNS  1440
TEGETPCGSS FAVFYFISFY MLCAFLIINL FVAVIMDNFD YLTRDWSILG PHHLDEFKRI  1500
WAEYDPEAKG RIKHLDVVTL LRRIQPPLGF GKLCPHRVAC KRLVSMNNPL NSDGTVMFNA  1560
TLFALVRTAL RIKTEGNLEQ ANEELRAIIK KIWKRTSMKL LDQVVPPAGD DEVTVGKFYA  1620
TFLIQEYFRK FKKRKEQGLV GKPSQRNALS LQAGLRTLHD IGPEIRRAIS GDLTAEEELD  1680
KAMKEAVSAA SEDDIFRRAG GLFGNHVTYY QSDSRGNFPQ TFATQRPLHI NKTGNNQADT  1740
ESPSHEKLVD STFTPSSYSS TGSNANINNA NNTALGRFPH PAGYSSTVST VEGHGPPLSP  1800
AVRVQEAAWK LSSKRCHSRE SQGATVNQEI FPDETRSVRN SEEAEYCSEP SLLSTDMFSY  1860
QEDEHRQLTC PEEDKREIQP SPKRSFLRSA SLGRRASFHL ECLKRQKDQG GDISQKTALP  1920
LHLVHHQALA VAGLSPLLQR SHSPTTFPRP CPTPPVTPGS RGRPLRPIPT LRLEGAESSE  1980
KLNSSFPSIH CSSWSEETTA CSGSSSMARR ARPVSLTVPS QAGAPGRQFH GSASSLVEAV  2040
LISEGLGQFA QDPKFIEVTT QELADACDMT IEEMENAADN ILSGGAQQSP NGTLLPFVNC  2100
RDPGQDRAVA PEDESCAYAL GRGRSEEALA DSRSYVSNL                        2139

SEQ ID NO: 12          moltype = AA   length = 1880
FEATURE                Location/Qualifiers
source                 1..1880
                       mol_type = protein
                       organism = Mus musculus
SEQUENCE: 12
MEPPSPQDEG LRKQPKKPV PEILPRPPRA LFCLTLQNPL RKACISIVEW KPFETIILLT    60
IFANCVALAV YLPMPEDDNN TLNLGLEKLE YFFLIVFSIE AAMKIIAYGF LFHQDAYLRS   120
GWNVLDPIIV FLGVFTVILE QVNIIQTNTA PMSSKGAGLD VKALRAFRVL RPLRLVSGVP   180
SLQVVLNSIF KAMLPLFHIA LLVLFMVIIY AIIGLELFKG KMHKTCYFIG TDIVATVENE   240
KPSPCARTGS GRPCTINGSE CRGGWPGPNH GITHFDNFAF SMLTVYQCIS MEGWTDVLYW   300
VNDAIGNEWP WIYFVTLILL GSFFILNLVL GVLSGEFTKE REKAKSRGTF QKLREKQQLE   360
EDLRGYMSWI TQEVMDVDD LREGKLSLDE GGSTDESLYE IEGLNKIIQF IRHWRQWNRV   420
FRWKCHDLVK SKVFYWLVIL IVALNTLSIA SEHHNQPLWL THLQDVANRV LLTLFTIEML   480
MKMYGLGLRQ YFMSIFNRFD CFVVCSGILE ILLVESGAMS PLGISVLRCI RLLRLFKITK   540
YWTSLSNLVA SLLNSIRSIA SLLLLLFLFI IFALLGMQLF GRYDFEDT EVRRSNFDNF   600
PQALISVFQV LTGEDWNSVM YNGIMAYGGP TYPGVLVCIY FIILFVCGNY ILLNVFLAIA   660
VDNLAEAESL TSAQKAKAEE RKRRKMSKGL PDKSEEERAT VTKKLEQKSK GEGIPTTAKL   720
KIDEFESNVN EVKDPYPSAD FPGDDEEDEP EIPVSPRPRP LAELQLKEKA VPIPEASSFF   780
IFSPTNKIRV LCHRIVNATW FTNFILLFIL LSSAALAAED PIRADSMRNQ ILEYFDYVFT   840
AVFTVEIVLK MTTYGAFLHK GSFCRNYFNI LDLLVVAVSL ISMGLESSAI SVVKILRVLR   900
VLRPLRAINR AKGLKHVVQC VFVAIRTIGN IVIVTTLLQF MFACIGVQLF KGKFYSCNDL   960
```

```
SKMTEEECRG YYYIYKDGDP TQIELRPRQW IHNDFHFDNV LSAMMSLFTV STFEGWPQLL   1020
YKAIDSNEED TGPVYNNRVE MAIFFIIYII LIAFFMMNIF VGFVIVTFQE QGETEYKNCE   1080
LDKNQRQCVQ YALKARPLRC YIPKNPYQYQ VWYVVTSSYF EYLMFALIML NTICLGMQHY   1140
NQSEQMNHIS DILNVAFTII FTLEMVLKLI AFKPRAYFGD PWNVFDFLIV IGSIIDVILS   1200
EIDTFLASSG GLYCLGGGCG NVDPDESARI SSAFFRLFRV MRLVKLLNRA EGVRTLLWTF   1260
IKSFQALPYV ALLIVMLFFI YAVIGMQMFG KIAMVDGTQI NRNNNFQTFP QAVLLLFRCA   1320
TGEAWQEILL ACSYGKLCDP ESDYAPGEEH TCGTNFAYYY FISFYMLCAF LIINLFVAVI   1380
MDNFDYLTRD WSILGPHHLD EFKAIWAEYD PEAKGRIKHL DVVTLLRRIQ PPLGFGKFCP   1440
HRVACKRLVG MNMPLNSDGT VTFNATLFAL VRTALKIKTE GNFEQANEEL RAIIKKIWKR   1500
TSMKLLDQVI PPIGDDEVTV GKFYATFLIQ EHFRKFMKRQ EEYYGYRPKK DTVQIQAGLR   1560
TIEEEAAPEI HRAISGDPTA EEELERAMVE AAMEEGIFRR TGGLFGQVDN FLERTNSLPP   1620
VMANQRPLQF AEIEMEELES PVFLEDFPQN PGTHPLARAN TNNANANVAY GNSSHRNNPV   1680
FSSICYEREF LGEADMPVTR EGPLSQPCSG SGPHSRSHVD KLKRPMTQRG MPEGQVPPSP   1740
CQLSQAEHPV QKEGKGPTSR FLETPNSRNF EEHVPRNSAH RCTAPATAML IQEALVRGGL   1800
DSLAADANFV MATGQALADA CQMEPEEVEV AATELLKQES PEAGPCLGAL SLRSSPGPPE   1860
SDDWGSQTTL ITPRCEAYTE                                              1880

SEQ ID NO: 13              moltype = AA   length = 108
FEATURE                    Location/Qualifiers
REGION                     1..108
                           note = Produced from hybridoma cells
VARIANT                    3..4
                           note = misc_feature - X can be any naturally occurring
                            amino acid
source                     1..108
                           mol_type = protein
                           organism = synthetic construct
SEQUENCE: 13
SQXXSITCTV SGFSLTSYGV HWVRQSPGKG LEWLGVIWRG GNTDYSAAFM SRLIITKDNS    60
KSQVFFKMNS LQADDTAIYY CVKKAYYYGS NYYTMDYWGQ GTSVTVSS                108

SEQ ID NO: 14              moltype = AA   length = 8
FEATURE                    Location/Qualifiers
REGION                     1..8
                           note = Produced from hybridoma cells
source                     1..8
                           mol_type = protein
                           organism = synthetic construct
SEQUENCE: 14
GFSLTSYG                                                              8

SEQ ID NO: 15              moltype = AA   length = 7
FEATURE                    Location/Qualifiers
REGION                     1..7
                           note = Produced from hybridoma cells
source                     1..7
                           mol_type = protein
                           organism = synthetic construct
SEQUENCE: 15
IWRGGNT                                                               7

SEQ ID NO: 16              moltype = AA   length = 16
FEATURE                    Location/Qualifiers
REGION                     1..16
                           note = Produced from hybridoma cell line
source                     1..16
                           mol_type = protein
                           organism = synthetic construct
SEQUENCE: 16
VKKAYYYGSN YYTMDY                                                    16

SEQ ID NO: 17              moltype = AA   length = 112
FEATURE                    Location/Qualifiers
REGION                     1..112
                           note = Produced from hybridoma cell line
source                     1..112
                           mol_type = protein
                           organism = synthetic construct
SEQUENCE: 17
DVLMTQTPLS LPVSLGDQAS ISCRSSQSIV HSNGNTYLEW YLQKPGQSPK LLIYKVSNRF    60
SGVPDRFSGS GSGTDFTLKI SRVEAEDLGV YYCFQGSHVP FTFGSGTKLE IK           112

SEQ ID NO: 18              moltype = AA   length = 11
FEATURE                    Location/Qualifiers
REGION                     1..11
                           note = Produced from hybridoma cell line
source                     1..11
                           mol_type = protein
                           organism = synthetic construct
```

```
SEQUENCE: 18
QSIVHSNGNT Y                                                          11

SEQ ID NO: 19           moltype =    length =
SEQUENCE: 19
000

SEQ ID NO: 20           moltype = AA   length = 9
FEATURE                 Location/Qualifiers
REGION                  1..9
                        note = Produced from hybridoma cell line
source                  1..9
                        mol_type = protein
                        organism = synthetic construct
SEQUENCE: 20
FQGSHVPFT                                                              9

SEQ ID NO: 21           moltype = AA   length = 91
FEATURE                 Location/Qualifiers
REGION                  1..91
                        note = Produced from hybridoma cell line
VARIANT                 2
                        note = misc_feature - X can be any naturally occurring
                         amino acid
source                  1..91
                        mol_type = protein
                        organism = synthetic construct
SEQUENCE: 21
KXSGYTFTEY TMHWVKQSHG KSLEWIGGIN RNNGGTYYNQ KVRGKATLTV DKSSSTAYME      60
LRSLTSEDSA VYYCAHRFAY WGQGTLVTVS A                                     91

SEQ ID NO: 22           moltype = AA   length = 8
FEATURE                 Location/Qualifiers
REGION                  1..8
                        note = Produced from hybridoma cell line
source                  1..8
                        mol_type = protein
                        organism = synthetic construct
SEQUENCE: 22
GYTFTEYT                                                               8

SEQ ID NO: 23           moltype = AA   length = 8
FEATURE                 Location/Qualifiers
REGION                  1..8
                        note = Produced from hybridoma cell line
source                  1..8
                        mol_type = protein
                        organism = synthetic construct
SEQUENCE: 23
INRNNGGT                                                               8

SEQ ID NO: 24           moltype = AA   length = 6
FEATURE                 Location/Qualifiers
REGION                  1..6
                        note = Produced from hybridoma cell line
source                  1..6
                        mol_type = protein
                        organism = synthetic construct
SEQUENCE: 24
AHRFAY                                                                 6

SEQ ID NO: 25           moltype = AA   length = 111
FEATURE                 Location/Qualifiers
REGION                  1..111
                        note = Produced from hybridoma cell line
source                  1..111
                        mol_type = protein
                        organism = synthetic construct
SEQUENCE: 25
DIVLTQSPAS LAVSLGQRAT ISCRASESVD SYGNSFMHWY QQKPGQPPKL LIYRASNLES      60
GIPARFSGSG SGTDFTLTIN PVEADDVATY YCQQSNEDPF TFGSGTKLEI K               111

SEQ ID NO: 26           moltype = AA   length = 10
FEATURE                 Location/Qualifiers
REGION                  1..10
                        note = Produced from hybridoma cell line
source                  1..10
                        mol_type = protein
                        organism = synthetic construct
```

```
SEQUENCE: 26
ESVDSYGNSF                                                                10

SEQ ID NO: 27           moltype =    length =
SEQUENCE: 27
000

SEQ ID NO: 28           moltype = AA   length = 9
FEATURE                 Location/Qualifiers
REGION                  1..9
                        note = Produced from hybridoma cell line
source                  1..9
                        mol_type = protein
                        organism = synthetic construct
SEQUENCE: 28
QQSNEDPFT                                                                 9

SEQ ID NO: 29           moltype = AA   length = 113
FEATURE                 Location/Qualifiers
REGION                  1..113
                        note = Produced from hybridoma cell line
source                  1..113
                        mol_type = protein
                        organism = synthetic construct
SEQUENCE: 29
GGLVQPGGSR KLSCAASGFT FSSFGMHWVR QAPEKGLEWV AYISSGSSTI YYADTVKGRF         60
TISRDNPKNT LFLQMTSLRS EDTAMYYCAR RGVRRPGEAM DYWGQGTSVT VSS                113

SEQ ID NO: 30           moltype = AA   length = 8
FEATURE                 Location/Qualifiers
REGION                  1..8
                        note = Produced from hybridoma cell line
source                  1..8
                        mol_type = protein
                        organism = synthetic construct
SEQUENCE: 30
GFTFSSFG                                                                  8

SEQ ID NO: 31           moltype = AA   length = 8
FEATURE                 Location/Qualifiers
REGION                  1..8
                        note = Produced from hybridoma cell line
source                  1..8
                        mol_type = protein
                        organism = synthetic construct
SEQUENCE: 31
ISSGSSTI                                                                  8

SEQ ID NO: 32           moltype = AA   length = 14
FEATURE                 Location/Qualifiers
REGION                  1..14
                        note = Produced from hybridoma cell line
source                  1..14
                        mol_type = protein
                        organism = synthetic construct
SEQUENCE: 32
ARRGVRRPGE AMDY                                                           14

SEQ ID NO: 33           moltype = AA   length = 110
FEATURE                 Location/Qualifiers
REGION                  1..110
                        note = Produced from hybridoma cell line
VARIANT                 100
                        note = misc_feature - X can be any naturally occurring
                         amino acid
VARIANT                 109
                        note = misc_feature - X can be any naturally occurring
                         amino acid
source                  1..110
                        mol_type = protein
                        organism = synthetic construct
SEQUENCE: 33
DIVLTQSPAS LAVSLGQRAT ISCRASKSVS TSGYSYMHWY QQKPGQPPKL LIYLASNLES         60
GVPARFSGSG SGTDFTLNIH PVEEEDAATY YCQHSRELTX SEGGPSWIXN                    110

SEQ ID NO: 34           moltype = AA   length = 10
FEATURE                 Location/Qualifiers
REGION                  1..10
                        note = Produced from hybridoma cell line
```

```
source                          1..10
                                mol_type = protein
                                organism = synthetic construct
SEQUENCE: 34
KSVSTSGYSY                                                                      10

SEQ ID NO: 35           moltype =    length =
SEQUENCE: 35
000

SEQ ID NO: 36           moltype = AA   length = 7
FEATURE                 Location/Qualifiers
REGION                  1..7
                        note = Produced from hybridoma cell line
source                  1..7
                        mol_type = protein
                        organism = synthetic construct
SEQUENCE: 36
QHSRELH                                                                         7

SEQ ID NO: 37           moltype = AA   length = 81
FEATURE                 Location/Qualifiers
REGION                  1..81
                        note = Produced from hybridoma cell line
VARIANT                 76
                        note = misc_feature - X can be any naturally occurring
                         amino acid
source                  1..81
                        mol_type = protein
                        organism = synthetic construct
SEQUENCE: 37
PGASVKISCK TSGYTFTEYT MHWVKQSHGK SLEWIGGINR NNGGTYYNQK VRGKATLTVD        60
KSSSTAYMEL RSLTSXGFCS L                                                  81

SEQ ID NO: 38           moltype = AA   length = 8
FEATURE                 Location/Qualifiers
REGION                  1..8
                        note = Produced from hybridoma cell line
source                  1..8
                        mol_type = protein
                        organism = synthetic construct
SEQUENCE: 38
GYTFTEYT                                                                        8

SEQ ID NO: 39           moltype = AA   length = 8
FEATURE                 Location/Qualifiers
REGION                  1..8
                        note = Produced from hybridoma cell line
source                  1..8
                        mol_type = protein
                        organism = synthetic construct
SEQUENCE: 39
INRNNGGT                                                                        8

SEQ ID NO: 40           moltype =    length =
SEQUENCE: 40
000

SEQ ID NO: 41           moltype = AA   length = 110
FEATURE                 Location/Qualifiers
REGION                  1..110
                        note = Produced from hybridoma cell line
VARIANT                 109
                        note = misc_feature - X can be any naturally occurring
                         amino acid
source                  1..110
                        mol_type = protein
                        organism = synthetic construct
SEQUENCE: 41
DIVLTQSPAS LAVSLGQRAT ISCRASKSVS TSGYSYMHWY QQKPGQPPKL LIYLASNLES        60
GVPARFSGSG SGTDFTLNIH PVEEEDAATY YCQHIRELTR SEGGPSWKXN                  110

SEQ ID NO: 42           moltype = AA   length = 10
FEATURE                 Location/Qualifiers
REGION                  1..10
                        note = Produced from hybridoma cell line
source                  1..10
                        mol_type = protein
                        organism = synthetic construct
```

```
SEQUENCE: 42
KSVSTSGYSY                                                            10

SEQ ID NO: 43           moltype =    length =
SEQUENCE: 43
000

SEQ ID NO: 44           moltype = AA   length = 7
FEATURE                 Location/Qualifiers
REGION                  1..7
                        note = Produced from hybridoma cell line
source                  1..7
                        mol_type = protein
                        organism = synthetic construct
SEQUENCE: 44
QHIRELT                                                               7

SEQ ID NO: 45           moltype = AA   length = 109
FEATURE                 Location/Qualifiers
REGION                  1..109
                        note = Produced from hybridoma cell line
VARIANT                 6..7
                        note = misc_feature - X can be any naturally occurring
                         amino acid
source                  1..109
                        mol_type = protein
                        organism = synthetic construct
SEQUENCE: 45
LVQPGXXLKL SCKSNEYEFP SHDMSWVRTT PEKRLELVAA INSDGGNTYY PDTMERRFII      60
SRDNTKKTLY LQMSSLRSED TALYYCARHS MVTPDLLTGA KGLWSLSLQ                 109

SEQ ID NO: 46           moltype = AA   length = 8
FEATURE                 Location/Qualifiers
REGION                  1..8
                        note = Produced from hybridoma cell line
source                  1..8
                        mol_type = protein
                        organism = synthetic construct
SEQUENCE: 46
EYEFPSHD                                                              8

SEQ ID NO: 47           moltype = AA   length = 8
FEATURE                 Location/Qualifiers
REGION                  1..8
                        note = Produced from hybridoma cell line
source                  1..8
                        mol_type = protein
                        organism = synthetic construct
SEQUENCE: 47
INSDGGNT                                                              8

SEQ ID NO: 48           moltype = AA   length = 11
FEATURE                 Location/Qualifiers
REGION                  1..11
                        note = Produced from hybridoma cell line
source                  1..11
                        mol_type = protein
                        organism = synthetic construct
SEQUENCE: 48
ARHSMVTPDL L                                                          11

SEQ ID NO: 49           moltype = AA   length = 110
FEATURE                 Location/Qualifiers
REGION                  1..110
                        note = Produced from hybridoma cell line
VARIANT                 109
                        note = misc_feature - X can be any naturally occurring
                         amino acid
source                  1..110
                        mol_type = protein
                        organism = synthetic construct
SEQUENCE: 49
DIVLTQSPAS LAVSLGQRAT ISCRASKSVS TSGYSYMHWY QQKPGQPPKL LIYLASNLES      60
GVPARFSGSG SGTDFTLNIH PVEEEDAATY YCQHIRELTR SEGGPSWKXN                110

SEQ ID NO: 50           moltype = AA   length = 10
FEATURE                 Location/Qualifiers
REGION                  1..10
                        note = Produced from hybridoma cell line
```

```
source                      1..10
                            mol_type = protein
                            organism = synthetic construct
SEQUENCE: 50
KSVSTSGYSY                                                                  10

SEQ ID NO: 51               moltype =    length =
SEQUENCE: 51
000

SEQ ID NO: 52               moltype = AA   length = 8
FEATURE                     Location/Qualifiers
REGION                      1..8
                            note = Produced from hybridoma cell line
source                      1..8
                            mol_type = protein
                            organism = synthetic construct
SEQUENCE: 52
QHIRELTR                                                                     8

SEQ ID NO: 53               moltype = AA   length = 86
FEATURE                     Location/Qualifiers
REGION                      1..86
                            note = Produced from hybridoma cell line
source                      1..86
                            mol_type = protein
                            organism = synthetic construct
SEQUENCE: 53
PGASVKISCK GSGYTFTDYT MHWVKQSHAK SLEWIGVISS YSGNTNYNQK FEGKATMTVD            60
KSSSTAYMEL ARLTSEDSAI YYCARH                                                86

SEQ ID NO: 54               moltype = AA   length = 8
FEATURE                     Location/Qualifiers
REGION                      1..8
                            note = Produced from hybridoma cell line
source                      1..8
                            mol_type = protein
                            organism = synthetic construct
SEQUENCE: 54
GYTFTDYT                                                                     8

SEQ ID NO: 55               moltype = AA   length = 8
FEATURE                     Location/Qualifiers
REGION                      1..8
                            note = Produced from hybridoma cell line
source                      1..8
                            mol_type = protein
                            organism = synthetic construct
SEQUENCE: 55
ISSYSGNT                                                                     8

SEQ ID NO: 56               moltype =    length =
SEQUENCE: 56
000

SEQ ID NO: 57               moltype = AA   length = 112
FEATURE                     Location/Qualifiers
REGION                      1..112
                            note = Produced from hybridoma cell line
source                      1..112
                            mol_type = protein
                            organism = synthetic construct
SEQUENCE: 57
DVVMTQTPLT LSVTIGQPAS ISCKSSQSLL DSDGKTYLNW LLQRPGQSPK RLIYLVSKLD            60
SGVPDRFTGS GSGTDFTLKI SRVEAEDLGV YYCWQGTHFP FTFGSGTKLE IK                   112

SEQ ID NO: 58               moltype = AA   length = 11
FEATURE                     Location/Qualifiers
REGION                      1..11
                            note = Produced from hybridoma cell line
source                      1..11
                            mol_type = protein
                            organism = synthetic construct
SEQUENCE: 58
QSLLDSDGKT Y                                                                11

SEQ ID NO: 59               moltype =    length =
SEQUENCE: 59
000
```

```
SEQ ID NO: 60           moltype = AA   length = 9
FEATURE                 Location/Qualifiers
REGION                  1..9
                        note = Produced from hybridoma cell line
source                  1..9
                        mol_type = protein
                        organism = synthetic construct
SEQUENCE: 60
WQGTHFPFT                                                                    9

SEQ ID NO: 61           moltype = AA   length = 108
FEATURE                 Location/Qualifiers
REGION                  1..108
                        note = Produced from hybridoma cell line
source                  1..108
                        mol_type = protein
                        organism = synthetic construct
SEQUENCE: 61
LVKPGGSLKL SCAASGFTFS SYAMSWVRQT PEKRLEWVAS ISSGGSTYYP DSVKGRFTIS            60
RDNARNILYL QMSSLRSEDT AMYYCARLGD GYYPFAYWGQ GTLVTVSA                        108

SEQ ID NO: 62           moltype = AA   length = 8
FEATURE                 Location/Qualifiers
REGION                  1..8
                        note = Produced from hybridoma cell line
source                  1..8
                        mol_type = protein
                        organism = synthetic construct
SEQUENCE: 62
GFTFSSYA                                                                     8

SEQ ID NO: 63           moltype = AA   length = 7
FEATURE                 Location/Qualifiers
REGION                  1..7
                        note = Produced from hybridoma cell line
source                  1..7
                        mol_type = protein
                        organism = synthetic construct
SEQUENCE: 63
ISSGGST                                                                      7

SEQ ID NO: 64           moltype = AA   length = 12
FEATURE                 Location/Qualifiers
REGION                  1..12
                        note = Produced from hybridoma cell line
source                  1..12
                        mol_type = protein
                        organism = synthetic construct
SEQUENCE: 64
ARLGDGYYPF AY                                                               12

SEQ ID NO: 65           moltype =    length =
SEQUENCE: 65
000

SEQ ID NO: 66           moltype =    length =
SEQUENCE: 66
000

SEQ ID NO: 67           moltype = AA   length = 6
FEATURE                 Location/Qualifiers
source                  1..6
                        mol_type = protein
                        organism = Homo sapiens
SEQUENCE: 67
AAAAAA                                                                       6

SEQ ID NO: 68           moltype = AA   length = 8
FEATURE                 Location/Qualifiers
source                  1..8
                        mol_type = protein
                        organism = Homo sapiens
SEQUENCE: 68
AAAAAAAA                                                                     8

SEQ ID NO: 69           moltype = AA   length = 95
FEATURE                 Location/Qualifiers
REGION                  1..95
```

```
                        note = Produced from hybridoma cell line
VARIANT                 3
                        note = misc_feature - X can be any naturally occurring
                          amino acid
source                  1..95
                        mol_type = protein
                        organism = synthetic construct
SEQUENCE: 69
KGXGYTFTDY TMHWVKQSHA KSLEWIGVIS SYSGNTNYNQ KFEGKATMTV DKSSSTAYME    60
LARLTSEDSA IYYCARHYGY DVTFWGQGTL VTVSA                               95

SEQ ID NO: 70           moltype = AA   length = 8
FEATURE                 Location/Qualifiers
REGION                  1..8
                        note = Produced from hybridoma cell line
source                  1..8
                        mol_type = protein
                        organism = synthetic construct
SEQUENCE: 70
GYTFTDYT                                                             8

SEQ ID NO: 71           moltype = AA   length = 8
FEATURE                 Location/Qualifiers
REGION                  1..8
                        note = Produced from hybridoma cell line
source                  1..8
                        mol_type = protein
                        organism = synthetic construct
SEQUENCE: 71
ISSYSGNT                                                             8

SEQ ID NO: 72           moltype = AA   length = 10
FEATURE                 Location/Qualifiers
REGION                  1..10
                        note = Produced from hybridoma cell line
source                  1..10
                        mol_type = protein
                        organism = synthetic construct
SEQUENCE: 72
ARHYGYDVTF                                                          10

SEQ ID NO: 73           moltype = AA   length = 107
FEATURE                 Location/Qualifiers
REGION                  1..107
                        note = Produced from hybridoma cell line
VARIANT                 86
                        note = misc_feature - X can be any naturally occurring
                          amino acid
VARIANT                 97
                        note = misc_feature - X can be any naturally occurring
                          amino acid
source                  1..107
                        mol_type = protein
                        organism = synthetic construct
SEQUENCE: 73
DIVLTQSPAS LAVSLGQRAT ISCRASKSVS TSGYSYMHWY QQKPGQPPKL LIYLASNLES    60
GVPARFSGSG SGTDFTLNIH PVEEEXAATY YCQHIRXAYT FGGGTKL                 107

SEQ ID NO: 74           moltype = AA   length = 10
FEATURE                 Location/Qualifiers
REGION                  1..10
                        note = Produced from hybridoma cell line
source                  1..10
                        mol_type = protein
                        organism = synthetic construct
SEQUENCE: 74
KSVSTSGYSY                                                          10

SEQ ID NO: 75           moltype =    length =
SEQUENCE: 75
000

SEQ ID NO: 76           moltype = AA   length = 8
FEATURE                 Location/Qualifiers
REGION                  1..8
                        note = Produced from hybridoma cell line
source                  1..8
                        mol_type = protein
                        organism = synthetic construct
```

```
SEQUENCE: 76
QHIRELTR                                                                  8

SEQ ID NO: 77           moltype = AA  length = 106
FEATURE                 Location/Qualifiers
REGION                  1..106
                        note = Produced from hybridoma cell line
source                  1..106
                        mol_type = protein
                        organism = synthetic construct
SEQUENCE: 77
LVQPGGSRKL SCAASGFTFS NFGMHWVRQA PEKGLEWVAY ISSGSNTIYY ADTVKGRFTI    60
SRDNGKNTLF LQMTSLRSED TAIYYCASYG NYAAYWGQGT LVTVSA                  106

SEQ ID NO: 78           moltype = AA  length = 8
FEATURE                 Location/Qualifiers
REGION                  1..8
                        note = Produced from hybridoma cell line
source                  1..8
                        mol_type = protein
                        organism = synthetic construct
SEQUENCE: 78
GFTFSNFG                                                                  8

SEQ ID NO: 79           moltype = AA  length = 8
FEATURE                 Location/Qualifiers
REGION                  1..8
                        note = Produced from hybridoma cell line
source                  1..8
                        mol_type = protein
                        organism = synthetic construct
SEQUENCE: 79
ISSGSNTI                                                                  8

SEQ ID NO: 80           moltype = AA  length = 9
FEATURE                 Location/Qualifiers
REGION                  1..9
                        note = Produced from hybridoma cell line
source                  1..9
                        mol_type = protein
                        organism = synthetic construct
SEQUENCE: 80
ASYGNYAAY                                                                 9

SEQ ID NO: 81           moltype = AA  length = 107
FEATURE                 Location/Qualifiers
REGION                  1..107
                        note = Produced from hybridoma cell line
VARIANT                 86
                        note = misc_feature - X can be any naturally occurring
                         amino acid
VARIANT                 97
                        note = misc_feature - X can be any naturally occurring
                         amino acid
source                  1..107
                        mol_type = protein
                        organism = synthetic construct
SEQUENCE: 81
DIVLTQSPAS LAVSLGQRAT ISCRASKSVS TSGYSYMHWY QQKPGQPPKL LIYLASNLES    60
GVPARFSGSG SGTDFTLNIH PVEEEXAATY YCQHIRXAYT FGGGTKL                 107

SEQ ID NO: 82           moltype = AA  length = 10
FEATURE                 Location/Qualifiers
REGION                  1..10
                        note = Produced from hybridoma cell line
source                  1..10
                        mol_type = protein
                        organism = synthetic construct
SEQUENCE: 82
KSVSTSGYSY                                                               10

SEQ ID NO: 83           moltype =     length =
SEQUENCE: 83
000

SEQ ID NO: 84           moltype = AA  length = 8
FEATURE                 Location/Qualifiers
REGION                  1..8
                        note = Produced from hybridoma cell line
```

```
VARIANT                    5
                           note = misc_feature - X can be any naturally occurring
                              amino acid
source                     1..8
                           mol_type = protein
                           organism = synthetic construct
SEQUENCE: 84
QHIRXAYT                                                                      8

SEQ ID NO: 85              moltype = AA  length = 95
FEATURE                    Location/Qualifiers
REGION                     1..95
                           note = Produced from hybridoma cell line
VARIANT                    57
                           note = misc_feature - X can be any naturally occurring
                              amino acid
source                     1..95
                           mol_type = protein
                           organism = synthetic construct
SEQUENCE: 85
LSITCTVSGF SLTDYGVSWI RQSPGKGLEW LGIIWGGGST YYNSVLKSRL SINKDNXKSQ             60
VFLKMNSLQT DDTAMYYCAK HRGDWGQGTL VTVSA                                       95

SEQ ID NO: 86              moltype = AA  length = 8
FEATURE                    Location/Qualifiers
REGION                     1..8
                           note = Produced from hybridoma cell line
source                     1..8
                           mol_type = protein
                           organism = synthetic construct
SEQUENCE: 86
GFSLTDYG                                                                      8

SEQ ID NO: 87              moltype = AA  length = 7
FEATURE                    Location/Qualifiers
REGION                     1..7
                           note = Produced from hybridoma cell line
source                     1..7
                           mol_type = protein
                           organism = synthetic construct
SEQUENCE: 87
IWGGGST                                                                       7

SEQ ID NO: 88              moltype = AA  length = 6
FEATURE                    Location/Qualifiers
REGION                     1..6
                           note = Produced from hybridoma cell line
source                     1..6
                           mol_type = protein
                           organism = synthetic construct
SEQUENCE: 88
AKHRGD                                                                        6

SEQ ID NO: 89              moltype = AA  length = 108
FEATURE                    Location/Qualifiers
REGION                     1..108
                           note = Produced from hybridoma cell line
VARIANT                    86
                           note = misc_feature - X can be any naturally occurring
                              amino acid
VARIANT                    89
                           note = misc_feature - X can be any naturally occurring
                              amino acid
source                     1..108
                           mol_type = protein
                           organism = synthetic construct
SEQUENCE: 89
DIVLTQSPAS LAVSLGQRAT ISCRASKSVS TSGYSYMHWY QQKPGQPPKL LIYLASNLES             60
GVPARFSGSG SGTDFTLNIH PVEEEXAAXY YCQHIRELTR SEGGPSWK                         108

SEQ ID NO: 90              moltype = AA  length = 10
FEATURE                    Location/Qualifiers
REGION                     1..10
                           note = Produced from hybridoma cell line
source                     1..10
                           mol_type = protein
                           organism = synthetic construct
SEQUENCE: 90
KSVSTSGYSY                                                                   10
```

```
SEQ ID NO: 91           moltype =    length =
SEQUENCE: 91
000

SEQ ID NO: 92           moltype = AA   length = 7
FEATURE                 Location/Qualifiers
REGION                  1..7
                        note = Produced from hybridoma cell line
source                  1..7
                        mol_type = protein
                        organism = synthetic construct
SEQUENCE: 92
STLGSLH                                                                    7

SEQ ID NO: 93           moltype =    length =
SEQUENCE: 93
000

SEQ ID NO: 94           moltype =    length =
SEQUENCE: 94
000

SEQ ID NO: 95           moltype =    length =
SEQUENCE: 95
000

SEQ ID NO: 96           moltype =    length =
SEQUENCE: 96
000

SEQ ID NO: 97           moltype = AA   length = 110
FEATURE                 Location/Qualifiers
REGION                  1..110
                        note = Produced from hybridoma cell line
VARIANT                 86
                        note = misc_feature - X can be any naturally occurring
                         amino acid
VARIANT                 109
                        note = misc_feature - X can be any naturally occurring
                         amino acid
source                  1..110
                        mol_type = protein
                        organism = synthetic construct
SEQUENCE: 97
DIVLTQSPAS LAVSLGQRAT ISCRASKSVS TSGYSYMHWY QQKPGQPPKL LIYLASNLES           60
GVPARFSGSG SGTDFTLNIH PVEEEXAATY YCQHIRELTR SEGGPSWKXN                    110

SEQ ID NO: 98           moltype = AA   length = 10
FEATURE                 Location/Qualifiers
REGION                  1..10
                        note = Produced from hybridoma cell line
source                  1..10
                        mol_type = protein
                        organism = synthetic construct
SEQUENCE: 98
KSVSTSGYSY                                                                10

SEQ ID NO: 99           moltype =    length =
SEQUENCE: 99
000

SEQ ID NO: 100          moltype = AA   length = 7
FEATURE                 Location/Qualifiers
REGION                  1..7
                        note = Produced from hybridoma cell line
source                  1..7
                        mol_type = protein
                        organism = synthetic construct
SEQUENCE: 100
QHIRELT                                                                    7

SEQ ID NO: 101          moltype =    length =
SEQUENCE: 101
000

SEQ ID NO: 102          moltype =    length =
SEQUENCE: 102
000
```

```
SEQ ID NO: 103         moltype =    length =
SEQUENCE: 103
000

SEQ ID NO: 104         moltype =    length =
SEQUENCE: 104
000

SEQ ID NO: 105         moltype = AA  length = 108
FEATURE                Location/Qualifiers
REGION                 1..108
                       note = Produced from hybridoma cell line
source                 1..108
                       mol_type = protein
                       organism = synthetic construct
SEQUENCE: 105
DIVLTQSPAS LAVSLGQRAT ISCRASKSVS TSGYSYMHWY QQKPGQPPKL LIYLASNLES    60
GVPARFSGSG SGTDFTLNIH PVEEEDAATY YCQHIRELTR SEGGPSWK                108

SEQ ID NO: 106         moltype = AA  length = 10
FEATURE                Location/Qualifiers
REGION                 1..10
                       note = Produced from hybridoma cell line
source                 1..10
                       mol_type = protein
                       organism = synthetic construct
SEQUENCE: 106
KSVSTSGYSY                                                          10

SEQ ID NO: 107         moltype =    length =
SEQUENCE: 107
000

SEQ ID NO: 108         moltype = AA  length = 9
FEATURE                Location/Qualifiers
REGION                 1..9
                       note = Produced from hybridoma cell line
source                 1..9
                       mol_type = protein
                       organism = synthetic construct
SEQUENCE: 108
CQHIRELTR                                                           9
```

The invention claimed is:

1. An isolated antibody, or antigen-binding fragment thereof, which binds to an alpha I subunit of an L-type voltage-gated calcium channel, wherein the antibody or antigen-binding fragment thereof, specifically binds to an amino acid sequence of an extracellular domain selected from SEQ ID NO:2 and which comprises: a heavy chain variable region ($V_H$) having the $V_H$ sequence of SEQ ID NO:37; and a light chain variable region ($V_L$) having the $V_L$ sequence of SEQ ID NO:41, wherein (i) $V_H$ comprises $V_H$CDR1 and $V_H$CDR2 amino acid sequences of SEQ ID NOS:38-39; and (ii) $V_L$ comprises $V_L$CDR1, $V_L$CDR2 and $V_L$CDR3 amino acid sequences of SEQ ID NO: 42, LAS, and SEQ ID NO: 44.

* * * * *